US012751995B2

(12) United States Patent
Lipshutz

(10) Patent No.: US 12,751,995 B2
(45) Date of Patent: Oct. 6, 2026

(54) METHODS AND MATERIALS FOR AMELIORATING CREATINE DEFICIENCY DISORDERS

(71) Applicant: The Regents of the University of California, Oakland, CA (US)

(72) Inventor: Gerald Lipshutz, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 686 days.

(21) Appl. No.: 18/311,469

(22) Filed: May 3, 2023

(65) Prior Publication Data

US 2024/0016894 A1 Jan. 18, 2024

Related U.S. Application Data

(60) Provisional application No. 63/337,786, filed on May 3, 2022.

(51) Int. Cl.
*A61K 38/19* (2006.01)
*A61K 48/00* (2006.01)
*A61P 3/00* (2006.01)
*C12N 15/86* (2006.01)

(52) U.S. Cl.
CPC .......... *A61K 38/19* (2013.01); *A61K 48/0041* (2013.01); *A61K 48/0066* (2013.01); *A61P 3/00* (2018.01); *C12N 15/86* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

2014/0010861 A1* 1/2014 Bancel ............... A61K 48/0066 536/23.4
2019/0241633 A1* 8/2019 Fotin-Mleczek .. A61K 31/7105

FOREIGN PATENT DOCUMENTS

WO WO-2014071067 A2 * 5/2014 ............. A61P 35/00

OTHER PUBLICATIONS

Stockler-Ipsiroglu, et al. Molecular Genetics and Metabolism 111.1 (2014): 16-25 (Year: 2014).*
Suhail, et al. Molecular Therapy Methods & Clinical Development 25 (2022): 278-296 (Year: 2022).*

* cited by examiner

*Primary Examiner* — Maria G Leavitt
*Assistant Examiner* — Brendan Thomas Tinsley
(74) *Attorney, Agent, or Firm* — Gates & Cooper LLP

(57) ABSTRACT

The invention disclosed herein provides methods and materials useful in gene therapy regimens designed to treat creatine deficiency disorders. Creatine deficiency disorders are inborn errors of creatine metabolism, an energy homeostasis molecule. One of these, guanidinoacetate N-methyltransferase (GAMT) deficiency, has clinical characteristics that include features of autism, self-mutilation, intellectual disability and seizures with approximately 40% having a disorder of movement; failure to thrive can also be a component. As disclosed herein, a gene therapy approach can result in long-term normalization of GAA with increased creatine in guanidinoacetate N-methyltransferase deficiency and at the same time resolves the behavioral phenotype in a murine model of the disorder. These findings have important implications for the development of a new therapy for this abnormality of creatine metabolism.

14 Claims, 7 Drawing Sheets

Specification includes a Sequence Listing.

In Vitro Studies

FIG. 6

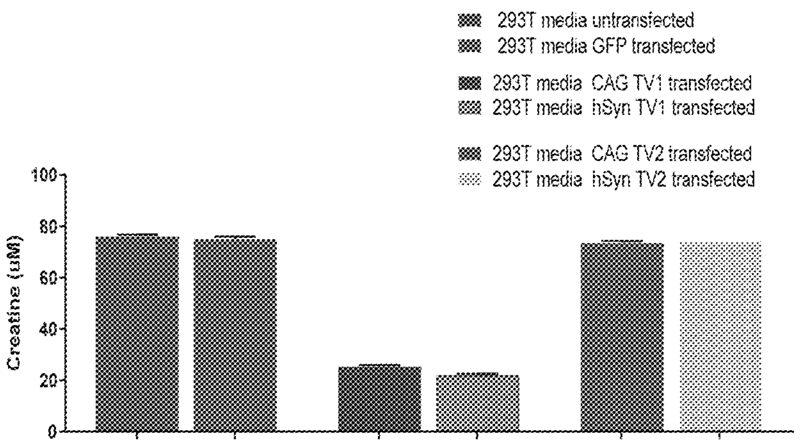

SLC6A8 TV1-expressing AAV vectors reduce creatine in media. Creatine reduction in media of 293 cells with AAV plasmids expressing SLC6A8 transcript variant 1 (TV1) (blues), not transcript variant 2 (TV2) (purple, pink) with both the hSynapsin and CBA/CMV enhancer (CAG) promoters.

Conclusion: Plasmid vectors with SLC6A8 TV1 cause uptake of creatine into cells demonstrating effective establishment of SLC6A8 transporter function.

In Vivo Studies

FIG. 7

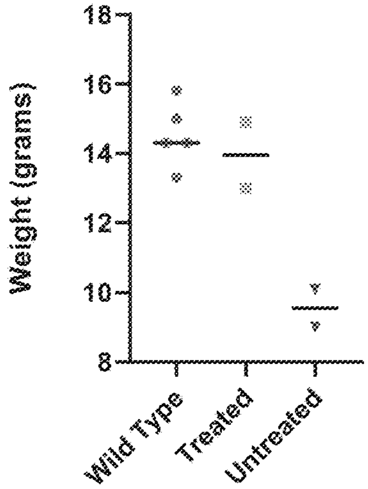

With IV AAV9 CBA-SLC6A8 at Postnatal day 2, marked improvement in animal weight (at day 30) is detected.

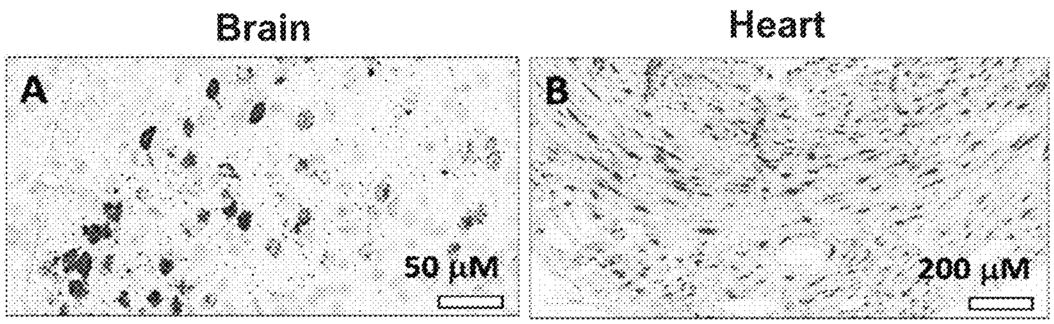

After AAV9 CBA promoter-SLC6A8 as a postnatal day 2 IV injection in Slc6a8 mutated mice, codon-optimized SLC6A8 transcript variant 1 RNA expression is detected (*in situ* hybridization) in these representative images when examined at 6 weeks after administration of viral vector. A) Brain demonstrates codon-optimized AAV-mediated human SLC6A8 in regions. B) Myocardium also demonstrates human SLC6A8 RNA expression in myocytes. RNA is labelled by the red precipitate.

METHODS AND MATERIALS FOR AMELIORATING CREATINE DEFICIENCY DISORDERS

CROSS-REFERENCE TO RELATED APPLICATIONS

This application claims the benefit under 35 U.S.C. Section 119(e) of and U.S. Provisional Patent Application Ser. No. 63/337,786, filed on May 3, 2022 and entitled "METHODS AND MATERIALS FOR AMELIORATING CREATINE DEFICIENCY DISORDERS" which application is incorporated by reference herein.

SEQUENCE LISTING

The instant application contains a Sequence Listing which has been submitted electronically in XML format and is hereby incorporated by reference in its entirety. Said XML copy, created on May 25, 2023, is named 30435_0447USU1_SL.xml and is 44,957 bytes in size.

TECHNICAL FIELD

The invention relates to methods and materials useful in treating creatine deficiency disorders.

BACKGROUND OF THE INVENTION

Creatine has an essential role in energy homeostasis, being particularly important in muscle and the brain due to their fluctuating energy demands. Outside of the buffering and transport function of high-energy phosphates, creatine is important for neurite growth cone migration, dendritic and axonal elongation, co-transmission on GABA postsynaptic receptors in the central nervous system (CNS) (1-4) and neurotransmitter release (5). Most cells do not rely on ATP/ADP free diffusion; instead creatine kinase/phosphocreatine (CK/PCr) serve as energy storage for the immediate regeneration of ATP as a shuttle of high-energy phosphates between sites of ATP production and energy consumption (6).

Parallel to dietary consumption, creatine biosynthesis occurs in two enzymatic steps primarily in the liver, kidneys, and pancreas. In the first, L-arginine:glycine amidinotransferase (AGAT) catalyzes the formation of guanidinoacetate (GAA) from arginine and glycine; guanidinoacetate N-methyltransferase (GAMT; EC 2.1.1.2) subsequently catalyzes the formation of creatine by GAA methylation from S-adenosylmethionine (7). Once synthesized, creatine is distributed through the bloodstream and is taken up through the cellular creatine transporter solute carrier family 6 member 8 (SLC6A8), a sodium and chloride-dependent symporter, against a large concentration gradient (8). Phosphocreatine reversibly transfers its N-phosphoryl group to ADP to regenerate ATP to prevent tissues from running out of energy. As at least half of creatine is synthesized endogenously, deficits in synthesis or transport result in cerebral creatine deficiency syndromes.

The cerebral creatine deficiency syndromes include the two autosomal recessive creatine biosynthetic disorders GAMT deficiency (8, 9) (MIM 601240) and AGAT deficiency (8) (MIM 602360). Mutations of SLC6A8 (MIM 300352) affect creatine transport into cells. The hallmark of this family of disorders is the near-complete absence of creatine in the brain (10) and the associated, predominantly neurological, disease. While signs and symptoms can range from mild to severe, intellectual disability, global developmental delay, speech impairment, extrapyramidal movement disorders, autism spectrum disorder, and seizures are common in all three (8, 11, 12). Together, the creatine deficiency disorders may represent one of the most frequent metabolic disorders with a primarily neurological phenotype (7).

Of the creatine deficiency disorders, GAMT loss of function mutations tend to result in the most severe phenotype. While likely underdiagnosed (5), the prevalence is estimated to range from 1 in 114,072 (13) to 1 in 250,000 births (14) with a carrier frequency from 1 in 1475 (15) to 1 in 812 (16); numerous different mutations (missense being the most common) have been reported (15) scattered throughout the gene with no hotspot or predominant mutation. The alteration of the Cr/PCr/CK system appears to be of particular importance during early brain development (7). Developmental delay is typically detected at three to twelve months (8); muscular hypotonia, involuntary movements, ataxia and autistic or self-aggressive behavior are common (8, 17, 18). Severe expressive language delay is an almost constant feature (19); most patients have no speech or language and, if present, is extremely limited with marked intellectual disability. Extrapyramidal movements and seizures are characteristic and often refractory to antiepileptics. With deficiency of GAMT, creatine synthesis is markedly impaired while GAA, accumulating in the plasma, CSF, urine, brain and other tissues, is thought to be the cause of the severe phenotype (8, 17) with the associated neurocognitive dysfunction likely due to both the deficiency of creatine and the accumulation of guanidinoacetate (5).

In GAMT deficiency, treatment requires life-long high dose creatine due to the low blood brain barrier permeability (18, 20) as endogenous synthesis is not possible. Oral creatine has an unpleasant taste making it at times difficult to administer to children. In addition, high-dose creatine administration is not always benign, having resulted in nephrolithiasis in some creatine deficient patients (21). With creatine supplementation, however, GAA still accumulates from peripheral excess (5, 20) and while GAA-lowering strategies (e.g. ornithine supplementation, arginine restriction (17), which can be difficult to maintain (15)) can greatly decrease plasma and cerebrospinal fluid GAA, brain levels can remain 10 times above normal levels (18). This leaves children at risk for seizures and progressive CNS injury due to the neurotoxicity of GAA (22).

In view of the issues noted above, there is a need for new methods and materials useful to address creatine deficiency disorders.

SUMMARY OF THE INVENTION

Herein, we describe studies developing gene therapy approaches for GAMT as well as SLC6A8 genetic deficiencies in order to overcome the limitations of oral creatine therapy. As discussed below, illustrative working embodiments of the invention restored hepatic gene expression, led to weight gain, normalization of plasma and urine GAA levels, restoration of brain and plasma creatine, and resolution of behavioral abnormalities when administered to a murine model of the GAMT disorder. These findings have implications for development of new therapeutic approaches for GAMT and SLC6A8 creatine deficiencies.

The invention disclosed herein has a number of embodiments. Embodiments of the invention include methods of making a composition comprising combining together in an aqueous formulation a GAMT polynucleotide comprising SEQ ID NO: 1 or a SLC6A8 polynucleotide comprising SEQ ID NO: 2; and optionally a pharmaceutical excipient selected from the group consisting of: a preservative, a tonicity adjusting agent, a detergent, a viscosity adjusting agent, a sugar or a pH adjusting agent. In typical embodiments of the invention, the polynucleotide comprising SEQ ID NO: 1 or the polynucleotide comprising SEQ ID NO: 2 is disposed in an adeno-associated viral vector such that when the adeno-associated viral vector infects a human cell, a functional GAMT protein or a functional SLC6A8 protein is expressed. In illustrative embodiments of the invention, the adeno-associated viral vector construct also comprises: a polynucleotide comprising a terminal repeat sequence; a polynucleotide comprising a promoter sequence; and/or a polynucleotide comprising a polyA tail sequence.

Embodiments of the invention also include compositions of matter such as those comprising a polynucleotide comprising SEQ ID NO: 1; or a polynucleotide comprising SEQ ID NO: 2. In certain embodiments, the composition comprises: an adeno-associated viral vector comprising: a polynucleotide sequence comprising a terminal repeat sequence; a polynucleotide sequence comprising a tissue specific (e.g. liver specific, brain specific) or ubiquitous expressing promoter; the polynucleotide comprising SEQ ID NO: 1 or the polynucleotide comprising SEQ ID NO: 2 (as codon optimized and/or CpG-deleted); and a polynucleotide sequence comprising a polyA tail signal; and a pharmaceutical excipient. In some embodiments of the invention, the composition comprises an adeno-associated viral vector encoding the polynucleotide comprising SEQ ID NO: 1 which, when transduced into a human liver cell expresses functional GAMT protein. In other embodiments of the invention, the composition comprises an adeno-associated viral vector encoding the polynucleotide comprising SEQ ID NO: 2 which, which, when transduced into a human cell expresses SLC6A8 protein. Typically, the adeno-associated viral vector construct comprises: a polynucleotide comprising a terminal repeat sequence; a polynucleotide comprising a promoter sequence; or a polynucleotide comprising a polyA tail sequence.

Embodiments of the invention also include methods of delivering a polynucleotide encoding a GAMT protein polypeptide or a polynucleotide encoding a SLC6A8 protein polypeptide into human cells, the methods comprising: contacting a composition comprising SEQ ID NO: 1 or SEQ ID NO: 2 with the human cells so that adeno associated vector(s) infect the human cells, thereby delivering the polynucleotides into the human cells (e.g., in vivo liver cells). Typically in these methods, the cells are in vivo cells present in an individual diagnosed with a creatine deficiency. In typical embodiments of the invention, the adeno associated viral vector comprising these genes is delivered intravenously.

Embodiments of the invention also include kits comprising a polynucleotide comprising SEQ ID NO: 1 or a polynucleotide comprising SEQ ID NO: 2 disposed in one or more containers. Optionally, the kit comprises: an adeno-associated viral vector comprising: a polynucleotide sequence comprising a terminal repeat sequence; a polynucleotide sequence comprising a tissue specific promoter; the polynucleotide comprising SEQ ID NO: 1 or the polynucleotide comprising SEQ ID NO: 2; and a polynucleotide sequence comprising a polyA tail signal. In certain embodiments, the kit comprises an adeno-associated viral vector encoding the polynucleotide comprising SEQ ID NO: 1 which, when transduced into a human liver cell expresses functional GAMT protein. In certain embodiments, the kit comprises an adeno-associated viral vector encoding the polynucleotide comprising SEQ ID NO: 2 which, when transduced into a human cell expresses SLC6A8 protein.

Related embodiments of the invention include using the compositions disclosed herein in gene therapy methods to treat s creatine deficiency. Such methods include, for example methods of delivering codon optimized polynucleotides encoding a GAMT protein or a SLC6A8 protein into human cells comprising contacting a composition disclosed herein (e.g. a composition comprising a adeno-associated viral vector comprising a codon optimized GAMT or SLC6A8 polynucleotide sequence) with human cells so that adeno-associated vector(s) infect the cells, thereby delivering the polynucleotides into the cells. In certain embodiments of the invention, the cells are in vivo liver cells, for example in vivo liver cells present in an individual diagnosed with creatine deficiency disorders. Related embodiments of the invention include methods of treating a subject diagnosed with a creatine deficiency, comprising selecting a subject with a creatine deficiency and administering to the subject a therapeutically effective amount of a pharmaceutical composition disclosed herein.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

FIG. 6 provides data from in vitro studies on SLC6A8 therapeutic AAV Vectors showing that they can reduce creatine in media. In particular data from creatine reduction studies in media of 293 cells with AAV plasmids expressing SLC6A8 transcript variant 1 (TV1) (blues), not transcript variant 2 (TV2) (purple, pink) with both the hSynapsin and CBA/CMV enhancer (CAG) promoters. This data shows that plasmid vectors with SLC6A8 TV1 cause uptake of creatine into cells demonstrating effective establishment of SLC6A8 transporter function.

FIG. 7. provides data from in vitro studies on SLC6A8 therapeutic AAV Vectors showing that when, as shown in the left panel, Slc6a8 mutated mice are administered IV AAV9 CBA-SLC6A8 at postnatal day 2, a marked improvement in animal weight (at day 30) is detected; and as shown in the right panel, after AAV9 CBA promoter-SLC6A8 is administered as a postnatal day 2 IV injection in S1c6a8 mutated mice, codon-optimized SLC6A8 transcript variant 1 RNA expression is detected (in situ hybridization) in these representative images when examined at 6 weeks after administration of viral vector. A) Brain demonstrates codon-optimized AAV-mediated human SLC6A8 in regions. B) Myocardium also demonstrates human SLC6A8 RNA expression in myocytes.

DETAILED DESCRIPTION OF THE INVENTION

Figure 1:
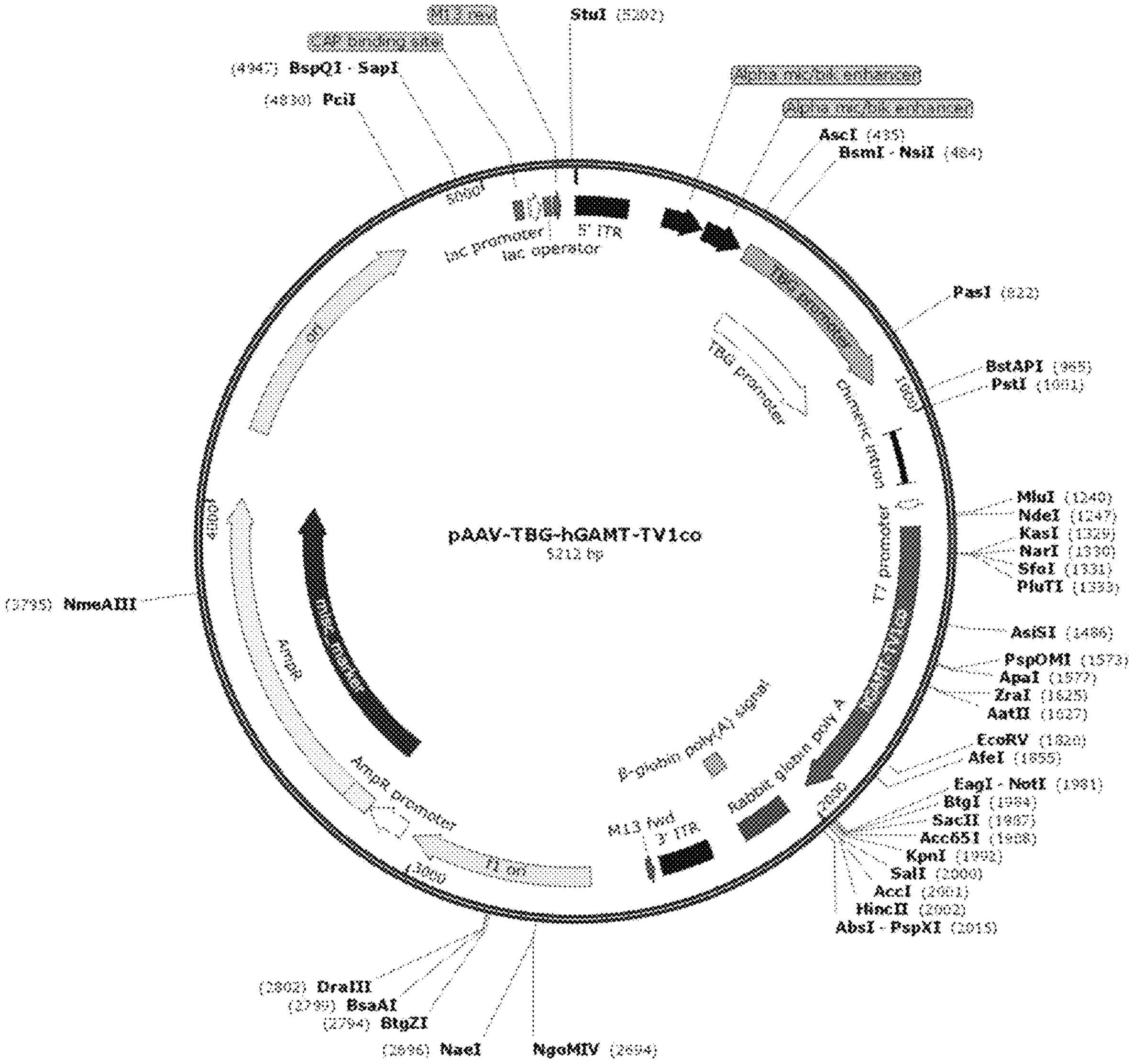
FIG. 1 provides a schematic of a map of the vector "pAAV-TBG-hGAMT-TV1co" including certain restriction endonuclease cleavage sites and vector elements.

In the description of embodiments, reference may be made to the accompanying figures which form a part hereof, and in which is shown by way of illustration a specific embodiment in which the invention may be practiced. It is to be understood that other embodiments may be utilized, and structural changes may be made without departing from the scope of the present invention. Many of the techniques and procedures described or referenced herein are well understood and commonly employed by those skilled in the art. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

All publications mentioned herein are incorporated herein by reference to disclose and describe aspects, methods and/or materials in connection with the cited publications (e.g. U.S. Patent Application Publication Numbers 20060115869, 20080176259, 20090311719, 20100183704 and 20190017069, and Diez-Fernandez C et al. Expert Opin Ther Targets, 2017 April; 21(4):391-399, doi: 10.1080/14728222.2017.1294685, Zhang G et al. J Clin Lab Anal. 2018 February; 32(2), doi: 10.1002/jcla.22241, Choi R et al. Ann Lab Med. 2017 January; 37(1):58-62, doi: 10.3343/alm.2017.37.1.58, Naso et al., BioDrugs (2017) 31:317-334, and Srinivasan et al., J Inherit Metab Dis. 2019 Mar. 6, doi: 10.1002/jimd.12067).

Creatine deficiency disorders are inborn errors of creatine metabolism, an energy homeostasis molecule. One of these, guanidinoacetate N-methyltransferase (GAMT) deficiency, has clinical characteristics that include features of autism, self-mutilation, intellectual disability and seizures with approximately 40% having a disorder of movement; failure to thrive can also be a component. Along with low creatine levels, guanidinoacetic acid (GAA) toxicity has been implicated in the pathophysiology of the disorder. Present-day therapy with oral creatine to control GAA lacks efficacy; seizures can persist. Dietary management and pharmacological ornithine treatment are challenging. Utilizing an AAV-based gene therapy approach to express human codon-optimized GAMT in hepatocytes, in situ hybridization and immunostaining demonstrated pan-hepatic GAMT expression. Serial collection of blood demonstrated a marked early and sustained reduction of GAA with normalization of plasma creatine; urinary GAA levels also markedly declined. The terminal time point demonstrated marked improvement in cerebral and myocardial creatine levels. In conjunction with the biochemical findings, treated mice gained weight to nearly match their wild type littermates, while behavioral studies demonstrated resolution of abnormalities; PET-CT imaging demonstrated improvement in brain metabolism. In conclusion, a gene therapy approach can result in long-term normalization of GAA with increased creatine in guanidinoacetate N-methyltransferase deficiency and at the same time resolves the behavioral phenotype in a murine model of the disorder. These findings have important implications for the development of a new therapy for this abnormality of creatine metabolism.

As noted above, embodiments of the invention include gene therapy methods that utilize adeno-associated virus (AAV). AAV is a non-enveloped virus that can be engineered to deliver DNA to target cells, which has attracted a significant amount of attention in the field, especially in clinical-stage experimental therapeutic strategies. The ability to generate recombinant AAV particles lacking any viral genes and containing DNA sequences of interest for various therapeutic applications has thus far proven to be one of the safest strategies for gene therapies. The review in Naso et al., BioDrugs (2017) 31:317-334 provides an overview of factors considered in the use of AAV as a vector for gene therapy. U.S. Patent Application Publication Numbers 20190017069 20180163227 20180104289 20170362670 20170348435 20170211095 20170304466 and 20170096682 disclose illustrative AAV methods and materials.

In certain embodiments, the composition comprises an adeno-associated viral vector that includes such a polynucleotide sequence operatively linked to a promoter. In this context, a wide variety of promoters can be used with embodiments of the invention including constitutive promoters that are expressed in a wide variety of cell types, as well as cell lineage specific promoters such as the thyroxine binding globulin (TBG promoter) which is liver-specific. Certain illustrative promoters are described, for example in Damdindorj, et al. (2014) A Comparative Analysis of Constitutive Promoters Located in Adeno-Associated Viral Vectors. PLoS ONE 9(8): e106472; as well as Pacak et al., (2008) Tissue specific promoters improve specificity of AAV9 mediated transgene expression following intra-vascular gene delivery in neonatal mice, Genet Vaccines Ther. 2008; 6: 13. Typically the compositions also includes a polynucleotide a polynucleotide sequence comprising a polyA tail signal; as well as a pharmaceutical excipient selected from the group consisting of a preservative, a tonicity adjusting agent, a detergent, a viscosity adjusting agent, a sugar or a pH adjusting agent.

Embodiments of the invention include compositions of matter such as those comprising a polynucleotide encoding a polypeptide that is encoded by SEQ ID NO: 1 (i.e., a GAMT protein); or a polynucleotide encoding a polypeptide that is encoded by SEQ ID NO: 2 (i.e., a SLC6A8 protein). In certain embodiments, the composition comprises: an adeno-associated viral vector comprising: a polynucleotide sequence comprising a terminal repeat sequence; a polynucleotide sequence comprising a tissue specific (e.g. liver specific) promoter; a polynucleotide encoding a polypeptide that is encoded by SEQ ID NO: 1; or a polynucleotide encoding a polypeptide that is encoded by SEQ ID NO: 2; and a polynucleotide sequence comprising a polyA tail signal; and a pharmaceutical excipient. In some embodiments of the invention, the composition comprises an adeno-associated viral vector including a polynucleotide encoding a GAMT polypeptide which, when transduced into a human liver cell expresses functional GAMT protein. In other embodiments of the invention, the composition comprises an adeno-associated viral vector including a polynucleotide encoding a SLC6A8 protein which, which, when transduced into a human cell expresses SLC6A8 protein. Typically, the adeno-associated viral vector construct comprises: a polynucleotide comprising a terminal repeat sequence; a polynucleotide comprising a promoter sequence; or a polynucleotide comprising a polyA tail sequence.

Other embodiments of the invention include kits such as a kit comprising a composition that includes a polynucleotide disclosed herein disposed in one or more containers. In certain embodiments of the invention, the kit comprises an adeno-associated viral vector comprising a polynucleotide sequence having a constellation of elements designed to facilitate GAMT or SLC6A8 protein expression in human cells, for example a sequence comprising a terminal repeat sequence, a polynucleotide sequence comprising a tissue (e.g., liver) specific promoter, a polynucleotide disclosed herein, a polynucleotide sequence comprising a polyA tail signal. The one or more containers can further comprise a pharmaceutical excipient selected from the group consisting of a preservative, a tonicity adjusting agent, a detergent, a viscosity adjusting agent, a sugar or a pH adjusting agent.

Compositions comprising AAV constructs (e.g. the AAV constructs disclosed herein) of the invention can be formulated as pharmaceutical compositions in a variety of forms adapted to the chosen route of administration. The compounds of the invention are typically administered in combination with a pharmaceutically acceptable vehicle such as an inert diluent. For compositions suitable for administration to humans, the term "excipient" is meant to include, but is not limited to, those ingredients described in Remington: The Science and Practice of Pharmacy, Lippincott Williams & Wilkins, 21st ed. (2006) the contents of which are incorporated by reference herein.

The compounds may also be administered in a variety of ways, for example intravenously. Solutions of the compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof.

Useful liquid carriers include water, alcohols or glycols or water/alcohol/glycol blends, in which the compounds can be dissolved or dispersed at effective levels, optionally with the aid of non-toxic surfactants. Adjuvants such as additional antimicrobial agents can be added to optimize the properties for a given use.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months.

In certain embodiments of the invention, AAV constructs disclosed herein may be used for the preparation of a pharmaceutical composition for the treatment of disease. Such disease may comprise a disease treatable by gene therapy, including creatine deficiency. The term "pharmaceutical composition", as used herein, refers to a composition comprising a therapeutically effective amount of active agents of the present invention and at least one non-naturally occurring pharmaceutically acceptable excipient. Embodiments of the invention relate to pharmaceutical compositions comprising one or more AAV constructs disclosed herein in combination with a pharmaceutically acceptable excipient.

The terms "pharmaceutically acceptable excipient", or "pharmaceutically acceptable carrier," "pharmaceutically acceptable diluent,", or "pharmaceutically acceptable vehicle," used interchangeably herein, refer to a non-toxic solid, semisolid or liquid filler, diluent, encapsulating material or formulation auxiliary of any conventional type. A pharmaceutically acceptable carrier is essentially non-toxic to recipients at the dosages and concentrations employed and is compatible with other ingredients of the formulation. Suitable carriers include, but are not limited to, water, dextrose, glycerol, saline, ethanol, and combinations thereof. The carrier can contain additional agents such as wetting or emulsifying agents, pH buffering agents, or adjuvants which enhance the effectiveness of the formulation.

The person skilled in the art will appreciate that the nature of the excipient in the pharmaceutical composition of the invention will depend to a great extent on the administration route. In the case of the pharmaceutical compositions formulated for use in gene therapy regimens, a pharmaceutical composition according to the invention normally contains the pharmaceutical composition of the invention mixed with one or more pharmaceutically acceptable excipients. These excipients can be, for example, inert fillers or diluents, such as sucrose, sorbitol, sugar, mannitol, microcrystalline cellulose, starches, including potato starch, calcium carbonate, sodium chloride, lactose, calcium phosphate, calcium sulfate or sodium phosphate; crumbling agents and disintegrants, for example cellulose derivatives, including microcrystalline cellulose, starches, including potato starch, sodium croscarmellose, alginates or alginic acid and chitosans; binding agents, for example sucrose, glucose, sorbitol, acacia, alginic acid, sodium alginate, gelatin, starch, pregelatinized starch, microcrystalline cellulose, aluminum magnesium silicate, sodium carboxymethylcellulose, methylcellulose, hydroxypropyl methylcellulose, ethylcellulose, polyvinylpyrrolidone, polyvinyl acetate or polyethylene glycol, and chitosans; lubricating agents, including glidants and antiadhesive agents, for example magnesium stearate, zinc stearate, stearic acid, silicas, hydrogenated vegetable oils or talc.

The present invention further provides methods associated with gene therapy regimens such as methods of delivering a nucleic acid encoding a codon optimized GAMT or SLC6A8 polynucleotide sequence into a cell so that the cell expresses GAMT or SLC6A8 protein. In such methods, the virus may be administered to the cell by standard viral transduction methods, as are known in the art. Preferably, the virus particles are added to the cells at the appropriate multiplicity of infection according to standard transduction methods appropriate for the particular target cells. Titers of virus to administer can vary, depending upon the target cell type and the particular virus vector, and may be determined by those of skill in the art without undue experimentation. Alternatively, administration of an AAV vector(s) of the present invention (e.g. the AAV constructs disclosed herein) can be accomplished by any other means known in the art.

Recombinant AAV virus vectors are preferably administered to the cell in a biologically-effective amount. A "biologically-effective" amount of the virus vector is an amount that is sufficient to result in infection (or transduction) and expression of the heterologous nucleic acid sequence in the cell. If the virus is administered to a cell in vivo (e.g., the virus is administered to a subject as described below), a "biologically-effective" amount of the virus vector is an amount that is sufficient to result in transduction and expression of the heterologous nucleic acid sequence in a target cell. The cell to be administered the inventive virus vector may be of any type, including but not limited to hepatic cells.

A "therapeutically-effective" amount as used herein is an amount that is sufficient to alleviate (e.g., mitigate, decrease, reduce) at least one of the symptoms associated with a disease state (e.g. one caused by GAMT or SLC6A8 deficiency). Alternatively stated, a "therapeutically-effective" amount is an amount that is sufficient to provide some improvement in the condition of the subject.

A further aspect of the invention is a method of treating subjects in vivo with the inventive viral constructs. Administration of the AAV constructs of the present invention to a human subject or an animal in need thereof can be by any means known in the art for administering virus vectors.

Exemplary modes of administration include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspensions in liquid prior to injection, or as emulsions. Alternatively, one may administer the virus in a local rather than systemic manner, for example in a depot or sustained-release formulation.

In particularly preformed embodiments of the invention, the nucleotide sequence(s) of interest is/are delivered to the liver of the subject. Administration to the liver may be achieved by any method known in art, including, but not limited to intravenous administration, intraportal administration, intrabilary administration, intra-arterial administration, and direct injection into the liver parenchyma.

Further aspects and embodiments of the invention are shown in the following examples.

Example 1: Studies on Ameliorating Guanidinoacetate Methyltransferase (GAMT) Creatine Deficiency Disorder Certain disclosure discussed in this Example is found in Khoja et al., Mol Ther Methods Clin Dev. 2022 Mar. 28; 25:278-296. doi: 10.1016/j.omtm.2022.03.015. eCollection 2022 Jun. 9 (hereinafter "Khoja et al.").

As disclosed herein, we have developed a gene therapy approach for one of the creatine deficiency disorders called guanidonoacetate methyltransferase (GAMT) deficiency, an autosomal recessive disorder that causes of an array of symptoms or signs including hypotonia, involuntary extrapyramidal movements, seizures, slurred speech, and in some cases autism. Patients typically have elevated plasma guanidinoacetate (GAA) and reduced creatine, a high energy molecule needed for normal brain development and neuronal activity. We have taken two approaches and have tested these AAV vectors in a transgenic GAMT-deficient murine model. We have synthesized a codon-optimized cDNA of transcript variant 1 of GAMT for development of our viral vector approach. 1) We have developed an adeno-associated viral vector that expresses a codon-optimized human cDNA of GAMT under the control of a liver-specific promoter. When administered by intravenous route to GAMT deficient mice, plasma creatine increases and GAA declines, both to near normal values. Affected male and female mice, while reduced in size compared to littermates, after gene therapy increase in weight to match that of their GAMT wild type siblings. 2) We have developed an adeno-associated viral vector that expressed codon-optimized human cDNA of GAMT under a muscle-specific promoter. This has been administered intravenously and results in reduction of plasma GAA and a marked increase in creatine.

Aspects of these studies are discussed below.

AAV-GAMT is Useful to Control GAA and in the Restoration of Creatine with a Dose-Dependent Effect in a Transgenic Animal Model Transgenic mice deficient in Gamt were developed as a knockout model and biochemically replicate GAMT deficiency in patients with markedly elevated guanidinoacetic acid and markedly reduced creatine in plasma and tissues (23). While they are biochemically similar to human patients, few behavioral deficits have been found (24). Gamt-deficient mice (8 weeks of age, C57Bl/6 background) were administered one of four escalating doses of AAV expressing human codon-optimized GAMT (hcoGAMT) under a liver-specific (thyroxine binding globulin (TBG)) promoter to determine the optimal dose for long-term testing (n=5 per group). Doses of $5\times10^{12}$, $1\times10^{13}$, $5\times10^{13}$, and $1\times10^{14}$ genome copies per kilogram (GC/kg) were intravenously administered after baseline blood sampling. Mice were euthanized 30 days after administration to assess dose and effect by multiple parameters.

AAV vector copy number per diploid hepatic genome in these Gamt−/− mice was determined at each dose (FIG. 1A of Khoja et al.). As expected, AAV copy numbers increased with increasing dose (mean copies per diploid hepatic genome±standard deviation (SD)): $5\times10^{12}$ GC/kg: 0.37±0.35; $1\times10^{13}$ GC/kg: 1.58±1.2; $5\times10^{13}$ GC/kg: 33.98±18.28; $1\times10^{14}$ GC/kg: 75.32±28.60 copy numbers per diploid hepatic genome (n=5 for $5\times10^{12}$, n=4 for $1\times10^{13}$, n=4 for $5\times10^{13}$, and n=3 for $1\times10^{14}$). Human codon-optimized GAMT RNA was quantified as fold-change in gene expression by real-time PCR (n=5 per dose) (FIG. 1B of Khoja et al.). AAV-mediated hepatocyte GAMT RNA increased with increasing dose (mean±SD): $5\times10^{12}$ GC/kg: 6,818±4,018; $1\times10^{13}$ GC/kg: 12,058±8,259; $5\times10^{13}$ GC/kg: 41,428±11,590; $1\times10^{14}$ GC/kg: 69,709±27,152. GAMT protein was examined by Western blot with β-actin as an internal housekeeping protein to evaluate loading. Incremental increases in band density for GAMT were detected with increasing dose (FIG. 1C of Khoja et al.). With quantitation (n=3 per group), increased protein expression was objectively determined relative to β-actin: $5\times10^{12}$: ±0.17; $1\times10^{13}$: 0.56±0.46; $5\times10^{13}$: 1.11±0.08; $1\times10^{14}$: 1.63±0.24 (FIG. 1D of Khoja et al.).

AAV-mediated liver-specific GAMT expression was also evaluated by in situ hybridization with a codon-optimized human GAMT-specific probe in Gamt−/− mice. With increasing administered AAV dose, hepatic codon-optimized GAMT RNA expression increases as demonstrated by greater density of probe-specific chromogenic deposition (red; representative images in FIG. 2 of Khoja et al.): A) wild type Gamt+/+; B) $5\times10^{12}$ GC/kg; C) $1\times10^{13}$ GC/kg; D) $5\times10^{13}$ GC/kg; E) $1\times10^{14}$ GC/kg. Similarly, hepatic GAMT protein expression (in these Gamt−/− mice) increased with escalating doses as demonstrated by human GAMT-specific immunohistochemistry (representative images in FIG. 2 of Khoja et al.: F) wild type Gamt+/+; G) $5\times10^{12}$ GC/kg; H) $1\times10^{13}$ GC/kg; I) $5\times10^{13}$ GC/kg; J) $1\times10^{14}$ GC/kg).

With the marked increase in GAMT hepatic protein there is an improvement of the metabolic response. While plasma creatine (FIG. 2K of Khoja et al.) did increase (96.38±84.8 nmol/ml) with the lowest dose of vector ($5\times10^{12}$ GC/kg) from the pretreatment level (35.53±13.75 nmol/ml (p=0.013 vs. Gamt+/+)), plasma creatine continued to rise sequentially with each dose escalation, becoming equivalent (p=0.997) to wild type plasma creatine levels (249.39±37.6 nmol/ml) at the highest dose ($1\times10^{14}$ GC/kg: 237.57±37.4 nmol/ml). Lower doses of vector also resulted in improved plasma creatine levels ($1\times10^{13}$ GC/kg: 148.54±96.60, p=0.13 vs. Gamt+/+; $5\times10^{13}$ GC/kg: 196.13±62.10, p=0.60 vs. Gamt+/+) (FIG. 2K, n=5 per group). High-level antibodies to AAV serotype rh10 were present as expected when plasma was tested at 4 months after vector administration (data not shown).

Simultaneous with increases in creatine, plasma GAA levels declined. While markedly elevated pretreatment (red data points), a steady decline was detected with incremental dose increases (blue data points) ($5\times10^{12}$ GC/kg: 101.55±13.70 vs. 128.36±22.00 nmol/ml pretreatment, p<0.0001 vs. wild type; $1\times10^{13}$ GC/kg: 82.83±29.00 vs. 128.69±30.10 nmol/ml pretreatment, p<0.0001 vs. wild type; $5\times10^{13}$ GC/kg: 19.512±7.90 vs. 119.45±19.00 nmol/ml pretreatment, p=0.43 vs. wild type; $1\times10^{14}$ GC/kg: 11.37±0.97 vs. 126.37±5.8 nmol/ml pretreatment, expressed as treated vs. untreated, n=5 per group) (FIG. 2L of Khoja et al.). With a dose of $1\times10^{14}$ GC/kg, near equivalency (p=0.92) to wild type (Gamt+/+) mouse plasma levels of GAA (5.17±0.52 nmol/ml) was achieved. As the dose of $1\times10^{14}$ GC/kg achieved restoration of plasma creatine levels and amelioration of elevated plasma GAA, this dose was chosen for administration and assessment in long-term studies.

A single intravenous dose of AAV expressing human codon-optimized GAMT results in improved weight gain.

With the optimal intravenous dose now determined, equal numbers of genders and groups (Gamt+/+, Gamt−/−, treated Gamt−/−) of 2-month-old mice were analyzed (n=8 per genotype group with 4 males and 4 females included in each group) in a twelve-month study. Gamt+/+ and untreated Gamt−/− mice received vehicle alone while the experimental Gamt−/− group received $1\times10^{14}$ GC/kg of AAV-TBG-hcoGAMT intravenously after baseline blood sampling. Mice were followed for 1 year with all groups having 100% survival (data not shown). While all male groups started with similar weights (Time 0: Gamt+/+26.18±1.10 g; Gamt−/− 24.85±1.03 g; treated Gamt−/− 24.53±0.75 g; WT vs. treated mutant p=0.091, WT vs. untreated mutant p=0.214) (FIG. 3A of Khoja et al.), male mice demonstrated a dichotomy in response: untreated Gamt−/− mice (red data points) had little change in weight after week 10 while wild type mice (black data points) continually gained weight throughout the period of study (week 54: untreated Gamt−/− 26.80±1.02 g; Gamt+/+38.23±4.53; treated Gamt−/− 32.83±0.83). Overall, by 1 year AAV-TBG-treated Gamt−/− male mice also demonstrated substantial weight gain (blue data points; 32.83±0.83 grams; p=0.16 vs. Gamt+/+) when compared with untreated Gamt−/− mice (26.80±1.02 grams; p=0.02 vs. wild type) but not to the same extent of the wild type controls (38.23±4.53 grams).

Female AAV-TBG-treated Gamt−/− mice fared even better. Female mice were of similar weight at the beginning of the study (WT vs treated mutant p=0.603; WT vs untreated mutant p=0.338). Similar to the male cohort, untreated Gamt−/− mice (red data points) had little weight gain after week 10 (weight at beginning of study: untreated Gamt−/− 19.08±1.25 grams vs. 20.23±1.24 grams at week 54). AAV-TBG-treated Gamt−/− mice (blue data points) were near equivalent in their course of weight gain and weights at 1 year as wild type controls (black data points) (at week 54, Gamt+/+25.70±1.45 vs. 24.95±0.58 gram in treated Gamt−/−) (FIG. 3B, C of Khoja et al.). Overall, by 1 year AAV-treated Gamt−/− female mice had substantial weight gain and were comparable to wild type mice (p=0.58) unlike untreated Gamt−/− mice (p=0.002 vs. Gamt+/+).

Untreated Gamt−/− mice of both genders were visibly thinner and, when handled, demonstrated less subcutaneous adipose tissue. To better understand the recovery in weight with gene therapy, mice were imaged with whole-body microCT at 8 months of age, and the adipose tissues were quantified by AMIDE software and visualized in the 3D mode by ORS Dragonfly software. With this imaging, the adipose tissue is easily identified as the visualization demonstrates. Comparing the three groups, there is a relative restoration of the adipose tissue in the treated Gamt−/− mice such that they resemble that of the Gamt wild type in both genders. microCT imaging of all groups (FIG. 3D of Khoja et al.) was performed and representative images of body fat (brown) in wild type mice (Gamt+/+, left), untreated Gamt−/− mice (center), and Gamt−/− mice treated with gene therapy (right) are presented. Visibly, the untreated female Gamt−/− mice demonstrate reduced fat when compared with Gamt+/+ and treated Gamt−/− mice. Quantification of body weight (FIG. 3E of Khoja et al., left) (wild type 23.8±1.3 g, untreated Gamt−/− 18.75±0.13 g, treated Gamt−/− 22.78±2.24 g; p=0.610 Gamt+/+vs. treated Gamt−/−) and body fat (FIG. 3F of Khoja et al., left) by microCT at 8 months (Gamt+/+3510±516, untreated Gamt−/− 2347±363, treated Gamt−/− 2774.5±971.5 g, p=0.313 comparing treated Gamt−/− and Gamt+/+) in female mice demonstrates the marked improvement of body weight and some, non-statistically significant, improvement in adipose tissue deposition 8 months after AAV was administered.

Male mice demonstrate similar physical findings subjectively when handled, and microCT imaging also demonstrates reduced adipose tissue in untreated Gamt-deficient mice; similarly, some restoration of adipose tissue deposition was achieved with AAV-liver-specific-based gene therapy. Quantification of body weight (FIG. 3E of Khoja et al., right) in male mice (wild type 36.70±4.73 g, untreated Gamt−/− 27.90±0.92 g, treated Gamt−/− 31.25±1.28 g; p=0.08 wild type vs. treated Gamt−/−) and body fat (FIG. 3F of Khoja et al.) by microCT (wild type 6046.2±4280.7 mm3, untreated Gamt−/− 2680.6±347 mm3, treated Gamt−/− 4089.4±1226.5 mm3, p=0.590 comparing treated Gamt−/− and wild type) also demonstrates the marked improvement in body weight and fat 8 months after AAV administration. There is a correlation between body weight and body fat in in both female (FIG. 3G of Khoja et al.) and male (FIG. 3H of Khoja et al.) mice, and mice of both genders (FIG. 3I of Khoja et al.) when analyzed together, indicating that the body weight changes are, at least partially, contributed by the amount of adipose tissue present.

AAV Administration Results in Long-Term Hepatic GAMT Expression with Control of GAA and Restoration of Creatine Levels in Plasma, Urine, and Tissues.

AAV viral genomes (FIG. 4A of Khoja et al.) are maintained in hepatocytes to at least 1 year (length of study), albeit reduced when compared to the 30 day data, when administered in adult mice. Copy number variability per hepatocyte diploid genome when comparing male (66.44±23.04 vector copies per diploid genome) and female mice (29.85±14.90 vector copies per diploid genome) is detected as had been previously described (25) (n=8 for wild type, n=4 for Gamt−/−, and n=8 for treated Gamt−/−). Human liver demonstrates pan-hepatic expression of GAMT (FIG. 4B of Khoja et al.); the antibody employed in these studies is specific for the human enzyme and does not cross-react with murine Gamt (FIG. 4C of Khoja et al. is Gamt+/+). Transgene-encoded expression of GAMT from AAV is detected in the murine liver of both genders (representative images, FIG. 4D of Khoja et al. (female), E (male); Western blot in F). Immunohistochemistry demonstrates greater density of expression around vascular structures with more sparse expression with distance from vasculature. Plasma alanine aminotransferase (ALT) and aspartate aminotransferase (AST) were compared between Gamt+/+, untreated Gamt−/−, and treated Gamt−/− (4 mice per group); no statistically significant differences were found between Gamt wild type and AAV-treated Gamt−/− mice (FIG. 4G, H of Khoja et al.).

Figure 5:
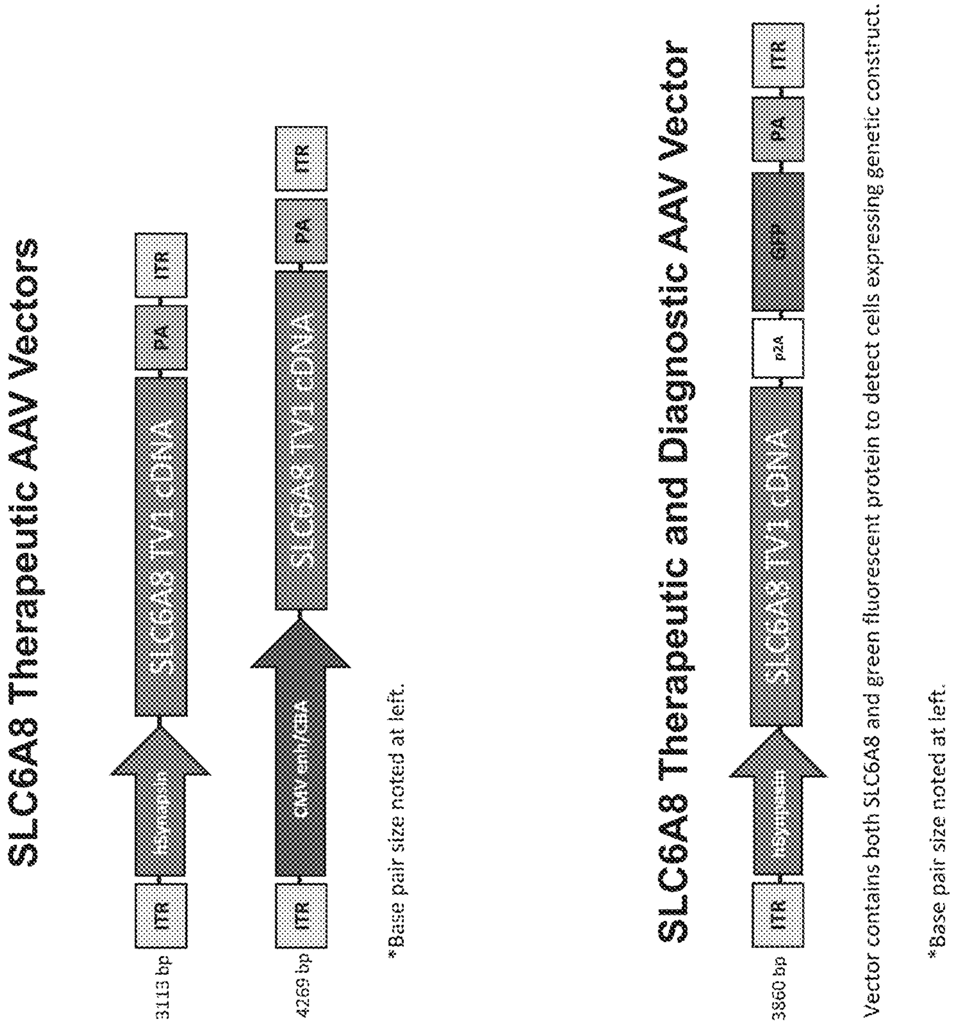
FIG. 5 provides cartoon schematics showing elements of SLC6A8 Therapeutic AAV Vectors (upper panel) and SLC6A8 Therapeutic and Diagnostic AAV Vectors (lower panel).

Pathognomonic to GAMT deficiency is markedly reduced plasma creatine with elevated GAA levels. GAA in Gamt−/− mice (FIG. 5A, B of Khoja et al.) was markedly elevated prior to vector administration in both male (Time 0: 154.93±26.00 in Gamt−/− (red) vs. 5.17±0.52 nmol/ml in Gamt+/+ (black), p<0.01) and female (Time 0: 140.84±15.38 in Gamt−/− (red) vs. 8.64±5.53 nmol/ml in Gamt+/+ (black), p<0.01) mice. Plasma GAA levels were markedly reduced with hepatic based gene therapy in treated males (A) (blue data points: plasma GAA at 12 months: Gamt+/+4.90±1.67 vs. treated Gamt−/− 7.33±0.70 nmol/ml (p=0.115); untreated vs. treated Gamt−/− and Gamt+/+ both p=0.001 (n=4 per group)) and females (B) (plasma GAA at 12 months: Gamt+/+6.49±5.63 vs. treated Gamt−/− 11.67±4.41 nmol/ml (p=0.379); untreated vs. treated Gamt−/− and Gamt+/+, both p<0.002 (n=4 per group)). The therapeutic response in plasma creatine was similar (FIG. 5 C, D of Khoja et al.). Creatine in untreated Gamt−/− mice is markedly reduced in both males (Gamt+/+ (black) 249.39±37.60 vs. 30.10±7.80 nmol/ml in Gamt−/− (red), p<0.01) and females (Gamt+/+275.39±55.36 vs. 26.72±6.77 nmol/ml in Gamt−/−, p<0.01 (n=4 per group)). Plasma creatine levels were normalized in treated males (blue data points) (at 12 months: Gamt+/+313.08±97.04 vs. treated Gamt−/− 294.13±41.04 nmol/ml (p=0.95); untreated vs. treated Gamt−/− p<0.01) and treated females (plasma creatine 12 months: Gamt+/+286.74±109.99 vs. treated Gamt−/− 277.45±102.15 nmol/ml (p=0.992); untreated vs. treated Gamt−/− and Gamt+/+ both p<0.03).

In GAMT deficiency, urinary GAA (FIG. 5E of Khoja et al.) is markedly elevated (Gamt+/+ (black) 0.87±0.52 nmol/ml vs. Gamt−/− (red) 10.34±3.18 nmol/ml, p<0.001) while creatine (FIG. 5F of Khoja et al.) is reduced (Gamt+/+ (black) 2.12±1.90 nmol/ml vs. Gamt−/− (red) 0.04±0.02 nmol/ml, p=0.04). These are both normalized (blue data points) with hepatic-based gene therapy (GAA at 12 months: Gamt+/+1.67±0.65 nmol/ml vs. treated Gamt−/− 2.20±1.08 nmol/ml (p=0.49); untreated Gamt−/− is 11.26±2.19 nmol/ml (p=0.005 compared to both); creatine at 12 months: Gamt+/+4.06±1.51 nmol/ml vs. treated Gamt−/− 1.93±1.42 nmol/ml (p=0.054); untreated Gamt−/− is 0.06±0.01 nmol/ml (p<0.01 compared to both)). (Urine samples, n=4-8 samples per time point).

Tissue levels of GAA are markedly elevated in Gamt−/− mice; these declined substantially with AAV-mediated restoration of hepatic expression of enzyme (FIG. 6 of Khoja et al.): Brain (A) 1283.08±474.46 nmol/g in Gamt−/− to 601.12±231.37 nmol/g in treated Gamt−/− (12.38±10.41 in Gamt+/+); Heart (B) 5933.20±1920.99 nmol/g in Gamt−/− to 14.49±5.82 nmol/g in treated Gamt−/− (7.38±3.73 in Gamt+/+); Kidney (C) 896.74±141.99 nmol/g in Gamt−/− to 285.22±110.62 nmol/g in treated Gamt−/− (135.03±18.31 in Gamt+/+); Liver (D) 1735.30±477.71 nmol/g in Gamt−/− to 47.56±43.72 nmol/g in treated Gamt−/− (13.47±4.89 in Gamt+/+); Muscle (E) 9915.83±3502.52 nmol/g in Gamt−/− to 16.50±5.47 nmol/g in treated Gamt−/− (4.77±2.71 in Gamt+/+) (all p<0.001 comparing untreated Gamt−/− with treated).

Mice also demonstrated a marked improvement in creatine levels in tissues: Brain (F) 12.21 nmol/g in Gamt−/− to 7923.47±1601.89 nmol/g in treated Gamt−/− (8510.81±1373.37 in Gamt+/+), p=0.683 to Gamt+/+; Heart (G) 41.92±13.58 nmol/g in Gamt−/− to 8203.54±2356.80 nmol/g in treated Gamt−/− (8225.95±2160.20 in Gamt+/+), p>0.999 to Gamt+/+; Kidney (H) 0.00±0.00 nmol/g in Gamt−/− to 612.16±132.63 nmol/g in treated Gamt−/− (868.65±117.10 in Gamt+/+), p=0.003 to Gamt+/+; Liver (I) 0.00±0.00 nmol/g in Gamt−/− to 175.10±37.40 nmol/g in treated Gamt−/− (195.18±33.10 in Gamt+/+), p=0.485 to Gamt+/+; Muscle (J) 180.18±30.23 nmol/g in Gamt−/− to 17519.90±890.08 nmol/g in treated Gamt−/− (18681.10±2661.17 in Gamt+/+), p=0.442 to Gamt+/+.

CNS Metabolism and Behavioral Studies Show Resolution of Deficits with Gene Therapy.

Considering the importance of the creatine/phosphocreatine shuttle to cells with high-energy expenditures, we examined the uptake of glucose to the brain in Gamt-deficient mice. Fluorodeoxyglucose (18(F)-FDG)-positron-emission tomography (PET) is a well-established non-invasive imaging tool for monitoring changes in cerebral brain glucose metabolism in vivo. To examine restoration of hepatic Gamt and its effect as a treatment strategy in GAMT deficiency, we sought to examine the brain of this preclinical model. By measuring cerebral glucose metabolism with (18F)-FDG-PET we can detect neuronal dysfunction in vivo as brain glucose metabolism is determined by synaptic activity mainly in order to restore membrane potentials (26). To semi-quantitate tissue activity, we determined the activity divided by the decay-corrected activity injected into the mouse; this ratio is defined as the percent-injected dose per cubic centimeter in tissue (% ID/cc). Gamt-deficient mice showed decreased glucose uptake (FIG. 7A of Khoja et al.) (red data points, 5.52±1.23% ID/cc) compared to Gamt+/+ littermate controls (black data points, 8.84±0.90% ID/cc, p=0.024). With restoration of hepatic GAMT enzymatic activity, normalization of GAA levels and restoration of creatine in plasma, uptake improves to 7.55±1.17% ID/cc (blue data points) (p=0.389 compared to wild type; n=3 per group). This improved glucose uptake is visualized in the representative images of FIG. 7B of Khoja et al.

We similarly analyzed areas of the brain regarding the effect of GAMT deficiency and potential resolution with AAV-based hepatic gene therapy (FIG. 7C of Khoja et al.). Almost all 20 brain areas examined demonstrated similar changes in (18F)-FDG uptake compared to the whole brain data. In the whole brain data as above, (18F)-FDG uptake by the untreated Gamt-deficient brain was reduced by 37.6% compared to the wild type brain. Among the 20 brain areas, the most affected area was the thalamus with a 43.8% decrease; the least affected area was the brain stem (29% decrease). While most areas were sufficiently rescued by gene therapy (to erase the statistical difference between wild type and untreated Gamt−/−), the areas that were not include globus pallidus, internal capsule, rest of midbrain, superior colliculus, amygdala, and basal forebrain.

We evaluated if there was a substantial improvement in brain metabolism with restoration of GAMT activity in hepatocytes with a gene therapy approach and compared this to present day therapy with oral creatine supplementation. Regular chow was provided, followed by oral creatine supplementation, and later with AAV based hepatic gene therapy (regular chow only) where each mouse served as its own control (FIG. 7E, D of Khoja et al.). In these studies we did not detect a significant difference in brain metabolism with regular mouse chow followed by supplementation with oral creatine (5.24±0.76% ID/cc vs. 5.26±1.10% ID/cc, respectively; p>0.05, ns). However, with AAV administration imaging demonstrated a 40.1% increase over regular chow with creatine supplementation (7.37±0.92% ID/cc; p<0.05).

Behavioral testing was performed at 8 months of age (FIG. 8 of Khoja et al.) to analyze for abnormalities in learning and motor activity. While the murine biochemical abnormalities are comparable to humans with the disorder (9), there is only one previous study reporting behavioral data (24), and therein mice did not display severe neurological abnormalities. To further explore for behavioral abnormalities and their potential resolution with liver-specific gene therapy, male and female wild type, untreated Gamt−/− and AAV-hcoGAMT treated mice were subjected to testing in both learning and motor-based assessments.

The Barnes maze is a hippocampus-dependent learning and memory task, similar to the Morris water maze, where mice learn the relationship between distal spatial cues and a fixed escape location (27). During the acquisition phase, mice undergo four daily training trials. After 4 days, the escape tunnel is removed, and a probe trial is conducted to assess reference memory 24 hours after the final training session (short-term memory), and 7 days after the final training session (long-term memory).

Untreated Gamt−/− mice showed deficits in learning, with an increase in primary latency to the escape hole, demonstrated by increased area under the curve (AUC) of the learning curve (see red data points in FIG. 8A and red bar in B of Khoja et al.) (p=0.038 compared to wild type mice). This was resolved with AAV-based liver-specific gene therapy (p=0.916 compared to wild type (blue data points)). There were also differences in distance travelled by mice during the acquisition phase (FIG. 8C, D of Khoja et al.). Untreated Gamt−/− mice (red data points) travel a longer distance to reach the escape location compared to wild type mice (black data points) (p=0.024). Distance traveled is reduced in Gamt−/− mice treated with gene therapy (blue data points) and was not statistically different from wild type controls (p=0.119).

Examination of short-term reference memory during the probe trial at 24 hours showed no statistically significant difference in latency or distance travelled between the groups (FIG. 8E, F of Khoja et al.). However, at 1 week, again a test of longer term memory, the primary latency for the untreated Gamt−/− mice was prolonged (G, red data points) when compared, approaching statistical significance (p=0.074) to treated Gamt−/− mice. However, there was no difference in distance traveled (H).

Mice are known to utilize one of three search strategies when looking for the escape hole: a direct strategy using extra-maze spatial cues, a serial strategy around the perimeter of the maze, or a random strategy (Fig I). As learning progresses, Gamt+/+ and the treated Gamt−/− mice switch from using primarily non-hippocampal random (gray) and serial (orange) strategies, to a more hippocampal based direct strategy. (Note increase in size of blue proportion of activity from Day 1 to Day 4 in Gamt+/+ and treated Gamt−/− mice (from J to M).). In contrast, untreated GAMT−/− mice rely primarily on the serial search strategy, with reduced spatial pathway activity by day four compared to both the Gamt+/+ mice. In the probe trial at 24 hours (0), untreated Gamt-deficient mice (middle bar) have reduced direct pathway activity compared to the treated-Gamt−/− mice and Gamt wild types; by 1 week (P), a test of longer-term memory, the direct strategy is absent in untreated Gamt−/− mice (see middle bar), here mice rely primarily on the serial pathway and some random searching, the latter completely absent from wild type or treated Gamt−/− mice (see P, left and right bars).

Evaluation of muscle strength is an essential component of behavioral testing particularly with concern for a neuromuscular disorder or to evaluate treatments on motor performance. Grip strength was studied to measure the neuromuscular function as maximal muscle strength of forelimbs and hind limbs. The mice were assessed by gently grasping of the mouse on a grid connected to a sensor. All values obtained were normalized against mouse body weight (FIG. 9 of Khoja et al.). For both forepaw (A) and backpaw (B) grip strength was reduced in untreated Gamt−/− mice (forepaws: 2.83±0.25, backpaws: 3.40±0.56 N/g) compared to Gamt+/+ wild type controls (forepaws: 3.54±0.49, (p=0.002 compared to Gamt−/−), backpaws: 4.08±0.51 N/g, (p=0.045 compared to Gamt−/−)). There was marked recovery with AAV-based liver-specific gene therapy (forepaws: 3.20±0.34, backpaws: 4.07±0.61 N/g) with no statistically detectable difference between treated Gamt knockout and wild type mice (forepaws p=0.171, backpaws p=0.999) (n=4 per group).

Discussion

GAMT deficiency (OMIM 601240) is one of the more common creatine deficiency disorders. Creatine has a critical role in energy metabolism of muscle and neurons, both tissues with high-energy demand, and serves as a phosphate energy buffer recycling ATP by the creatine-phosphocreatine system. Despite optimal present-day medical therapy including protein restriction and ornithine supplementation, chronically elevated GAA levels have plagued some children and are likely responsible for persistent seizures, autistic features, and other cognitive abnormalities (5, 18). While it has been hypothesized that GAA interacts with GABAA receptors (4, 28), the exact mechanism of brain injury has not been completely elucidated; both diminished creatine and elevated GAA likely contribute to the neurological phenotype (9, 29). Herein, we sought to explore, and have demonstrated, a gene therapy approach for GAMT deficiency allowing for normal and stable plasma creatine levels with control of plasma GAA.

The main findings of these studies demonstrate that expression of human codon-optimized guanidinoacetate N-methyltransferase in hepatocytes of affected mice results in sustained expression of hepatic GAMT with restoration of plasma creatine levels and resolution of hyperguanidinoacetic acidemia. Urinary GAA was normalized, and creatine levels were similar to wild type controls. While brain creatine levels were restored, cerebral GAA was not completely normalized; this is likely due to lack of restoration of brain GAMT expression as the AAV vector is tissue limited to hepatocytes by the TBG promoter. The dose of vector administered is substantial and while the TBG promoter has been associated with hepatocellular carcinoma at times when used in vectors administered to neonatal mice, we did not detect any tumors or other liver abnormalities in the mice of this study (when euthanized 12 months after vector administration at ~14 months of age). While AAV8 may be the prototypical murine hepatotropic AAV, multiple other natural AAV serotypes are effective in transducing murine hepatocytes. These include AAV7, AAV9, and rh10, the latter being in the same Clade (Clade E) as serotype 8. We have successfully utilized serotype rh10 previously in murine hemophilia studies (30), murine arginase studies (31-33) and employed here for hepatocyte transduction in Gamt deficiency. Nevertheless, animals thrived with overall weight gain being similar to wild type littermate controls, including improvement in adipose deposition. Glucose consumption in the brain, while reduced in Gamt-deficient mice, was normalized with hepatic-based gene therapy. Motor and learning abnormalities present in mice with marked hyperguanidinoacetic acidemia and low creatine levels, as detected in behavioral testing, were largely resolved.

While GAMT in humans is expressed in high amounts in skeletal muscle, liver, heart and kidney, it is also expressed in the brain, albeit perhaps at lower levels (23); brain expression appears to be predominantly found in oligodendrocytes (34). The gene therapy approach employed in these studies utilized an adeno-associated viral vector expressing human GAMT under a liver-specific promoter, thus restricting expression to hepatocytes. It is evident from the data that this results in markedly improved and normalized creatine levels in the plasma, which is AAV dose-dependent. In addition, hepatocytes in male mice express GAMT from AAV at higher levels than from hepatocytes in female mice, consistent with the androgen-dependency of AAV transduction that has been previously demonstrated (25). There is some reduction in AAV genomes per hepatocyte from one month after administration to over 12 months at study completion. Hepatocyte turnover in the normal adult murine liver is slow overall as the life span of a hepatocyte is from 200 to 400 days; this may in part be the cause of this reduction (35). Levels of creatine are also normalized in the brain, heart, kidney, liver, and skeletal muscle. While GAA levels are simultaneously controlled in the plasma, heart, liver, and skeletal muscle, the brain and kidney, while markedly reduced, have persistent GAA levels. Unlike the heart and skeletal muscle where reduction in tissue GAA is likely from metabolic network flux through the plasma from reduction by the liver with restoration of GAMT enzymatic activity, this is less effective in the brain and kidney where endogenous enzymatic activity may be necessary for metabolic flux to be optimal. Both of these tissues normally possess endogenous Gamt expression, which is not restored with an AAV vector limited by a liver-specific promoter. Altering the vector to express in more tissues may address mildly persistent levels in these two organs.

While these studies demonstrate that despite the comparable mouse weights when these investigations began at 2 months of age, Gamt−/− mice gain less with time than Gamt+/+ controls and, as the PET-CT images demonstrate, do not appear to be due to mouse length or skeletal differences. While a marked reduction in adipose tissue mass has been previously described in murine Gamt deficiency (23), the studies conducted herein demonstrate that with restoration of GAMT expression there is improvement in the absolute fat mass as compared to both untreated Gamt−/− and Gamt+/+ controls. As has been previously demonstrated (23), the reduction in fat mass does not appear to be related to changes in levels of leptin, insulin, or adiponectin levels. It is not known if such reduced adiposity is present in GAMT-deficient patients.

Gamt-deficient mice in our studies demonstrated reduced brain glucose consumption; this was nearly resolved with hepatic-based GAMT gene therapy and was superior to mouse chow with creatine supplementation. In fact, the improvement in brain metabolism may be underestimated by the PET-CT studies. FDG uptake in the mouse brain decreases with age (36, 37) and this may have off-set the signal increase that creatine supplementation may have provided and reduced the signal intensity with the gene therapy approach.

In GAMT deficient patients, free ATP molecules and thus ATP levels in the brain are reported to be increased (38). High ATP levels inhibit glucose/fluorodeoxyglucose uptake and glycolysis through allosteric inhibition of phosphofructokinase (39, 40), consistent with the observation in our data. Thus, it is not unexpected that some behavioral findings would be present in affected mice. While the murine biochemical abnormalities of high plasma and urinary GAA along with low creatine are comparable to humans with the disorder (9), there is only one previous study reporting behavioral data in the murine Gamt-deficient model (24). In that report, Gamt−/− mice did not display severe neurological abnormalities: there was no gross ataxia or seizures (23). With more detailed investigation, the authors found that Gamt-deficient mice did show an inconspicuous finding of impaired retrieval of learned information (24); overall, this identified a subtle cognitive deficit. In the behavioral assays performed as part of this investigation, we found several previously undescribed abnormalities. Utilizing the Barnes maze, a hippocampal-dependent task similar to the Morris water maze, allowed for testing the ability of mice to learn the relationship between distal cues and a fixed escape location (27). In these studies, we detected evidence of a learning deficit during the acquisition phase. Compared to the Gamt+/+ mice, the untreated Gamt−/− mice acquire more slowly, having an abnormality in primary latency; untreated Gamt−/− mice also travel a longer distance to reach the escape location. These abnormalities in primary latency and distance traveled are resolved with AAV-based gene therapy. While examination of short-term memory lacked a statistically significant difference in latency, distance travelled or search strategy in Gamt-deficient mice, in tests of longer-term memory, the primary latency for the untreated Gamt−/− mice was prolonged approaching statistical significance. In addition, untreated Gamt−/− mice utilized a search strategy relying exclusively on serial and random methods while Gamt+/+ mice and treated Gamt−/− mice utilized a direct or spatial method as a much larger component of their search strategy. Together these findings suggest an abnormality in long-term memory that is largely resolved with AAV-based hepatic gene therapy even with incomplete resolution of brain GAA levels.

While gross ataxia was not detected in Gamt-deficient mice, motor abnormalities were present. While our studies were likely underpowered to detect statistically significant abnormalities in cerebellar function by rotarod testing (data not shown), Gamt-deficient mice did demonstrate a reduction in grip strength of the fore- and hind-paws; these motor performance issues were resolved with the gene therapy approach.

In conclusion, these studies developing a gene therapy method for GAMT deficiency led to the resolution of the majority of biochemical abnormalities in plasma, tissues and urine. Behavioral abnormalities in learning and motor activities, not previously reported in a murine model of the disorder, and abnormal brain metabolism were resolved with a gene therapy approach. GAA levels did not completely normalize in the brain; a more effective approach may include a ubiquitous promoter and a serotype that has increased ability cross the blood brain barrier. Additional alterations in the vector construct may also allow for decreased dose of administration. However, this first successful application of AAV-based gene therapy to GAMT deficiency suggests a path forward for clinical development of a gene therapy vector.

Materials and Methods

Molecular Cloning

Full length codon-optimized sequence of human GAMT (hcoGAMT) transcript variant 1 was synthesized and subcloned into pUC57-Simple vector by GenScript Biotech (Piscataway, NJ). The transgene containing 711 bp of hcoGAMT preceded by the Kozak sequence (GCCACC) was excised and subcloned into the pENN-AAV-TBG vector (provided by Julie Johnston PhD, University of Pennsylvania Vector Core) using MluI and KpnI restriction sites by standard molecular biology techniques. After confirmation of the transgene cloning using restriction digestion and Sanger sequencing, plasmid DNA (AAVrh10.TBG.PI.hGAMT-TV1co.rBG) was prepared using an EndoFree Plasmid Mega Kit (Qiagen, cat. 12381, Hilden, Germany).

The following is the complete hcoGAMT polynucleotide sequence:

(SEQ ID NO: 1)

```
ATGTCCGCCCCTTCAGCCACCCCCATCTTCGCCCCCGGGG
AAAACTGTAGTCCAGCATGGGGCGCCGCACCAGCCGCCTA
CGATGCCGCCGACACACACCTTAGGATTCTGGGTAAACCT
GTAATGGAACGATGGGAGACCCCCTATATGCACGCACTCG
CAGCCGCCGCCTCTTCCAAAGGAGGGCGCGTTCTTGAAGT
CGGCTTTGGAATGGCGATCGCAGCTTCAAAGGTTCAGGAG
GCCCCTATTGATGAGCATTGGATAATTGAATGTAATGATG
```

-continued

```
GTGTGTTTCAGAGATTGCGGGATTGGGCCCCAAGACAAAC
ACACAAGGTTATACCTCTTAAAGGACTGTGGGAAGACGTC
GCGCCAACTCTCCCTGATGGACACTTTGACGGCATTTTGT
ATGACACCTACCCCCTCTCCGAAGAAACATGGCACACGCA
TCAGTTCAACTTTATTAAAAATCACGCTTTTCGACTCCTC
AAACCGGGTGGAGTCCTCACATACTGCAACTTGACATCTT
GGGGTGAACTTATGAAATCTAAATATTCCGATATCACCAT
AATGTTCGAGGAGACCCAAGTGCCAGCGCTCCTTGAGGCC
GGTTTTAGACGCGAAAACATCAGAACTGAAGTCATGGCGC
TTGTGCCCCCCGCCGATTGCCGCTATTATGCCTTTCCTCA
AATGATTACCCCACTTGTGACAAAAGGTTAG.
```

The following is the complete hcoGAMT polypeptide sequence:

(SEQ ID NO: 13)

```
MSAPSATPIFAPGENCSPAWGAAPAAYDAADTHLRILGKP
VMERWETPYMHALAAAASSKGGRVLEVGFGMAIAASKVQE
APIDEHWIIECNDGVFQRLRDWAPRQTHKVIPLKGLWEDV
APTLPDGHFDGILYDTNIRTEVMALVPPADCRYYAFPQMI
TPLVTKGMSAPSATPIFAPGENCSPAWGAAPAAYDAADTH
LRILGKPVMERWETPYMHALAAAASSKGGRVLEVYPLSEE
TWHTHQFNFIKNHAFRLLKPGGVLTYCNLTSWGELMKSKY
SDITIMFEETQVPALLEAGFRRE.
```

AAV Vector Development

Recombinant serotype rh10 adeno-associated viral vectors were produced at the University of Pennsylvania Vector Core (Philadelphia, PA) as previously described (41). In brief, polyethylenimine as a transfection agent was used to transfect AAV cis, AAV trans, and adenovirus helper plasmids into HEK 293 cells. Three days post-transfection, culture supernatants were collected and AAV particles were then purified by ultracentrifugation iodixanol step gradient. Viral titering by genome copy number was performed by digital droplet PCR using a sequence from the polyadenylation signal. In this context, a variety of AAV vector serotypes can be used (e.g., serotypes 8 and 9).

Mouse Procedures

The constitutive guanidinoacetate methyltransferase knockout mouse (Gamt−/−, B6.Cg-Gamttm1Isb) (23) was obtained as a kind gift from Jeff Huang PhD (Department of Biology, Georgetown University) (MTA obtained from Dr Dirk Isbrandt, University of Cologne) that had been maintained on the C57BL/6 background and was used for these studies. These mice were housed at UCLA under specific pathogen-free conditions; food and water were provided ad libitum and there were no periods of fasting. Mice were fed mouse chow free of animal fat or protein sources (Labdiet/PMI Nutrition International, St. Louis, MO, USA, (Picolab Selected Mouse 30 IF/9F, 5V5M)). Mice underwent genotyping by collecting a small ear clip and performing PCR. All attempts were made to include equal numbers of male and female mice with littermate controls. At 8-12 weeks of age, mice were administered $1\times10^{14}$ genome copies (GC)/kg AAVrh10-TBG-hcoGAMT by intravenous injection; AAV was diluted in sterile pharmaceutical grade normal saline for injection. Mice were weighed weekly, blood was sampled by retroorbital collection under isoflurane anesthesia monthly, and urine was collected each 3 months. Mice were euthanized at 12 months by isoflurane overdose; tissues were collected and snap frozen with liquid nitrogen. Creatine (Sigma-Aldrich) was supplemented by oral gavage, dissolved in water Genotyping PCR Ear tissue snip was obtained and genomic DNA isolated and purified (Extracta DNA Prep for PCR-Tissue, cat #95091, Quantabio, Beverly, MA). PCR was performed using AccuStart™ II GelTrack PCR SuperMix (QuantaBio #89235). PCR conditions were performed for 35 cycles: 94° C.×30 sec, 63° C.×30 sec, 72° C. for 30 sec. Wild type amplicon is 265 bp and mutant amplicon is 430 bp.

Anti-AAV ELISA 96 well plates were coated overnight at 4° C. with 1×109 gc of AAVrh10 vector preparations per well in PBS. Ultraviolet light was used for 30 minutes to inactivate the AAV. Plates were then washed with 1×PBS+5% Tween four times followed by the addition of 200 □l blocking buffer (1×PBS+5% FCS) per well and incubated at 37° C. for 2 h. Plates were then washed with 1×PBS+5% Tween four times followed by the addition of 100 ul diluted plasma sample per well with incubation at 37° C. for 2 h. Plates were washed with 1×PBS+5% Tween four times followed by the addition of 50 μl 1:1000 diluted HRP-conjugated anti-mouse IgG (Thermo Fisher, Waltham, MA) to each well and were incubated at 37° C. for 1 h. Wells were washed with 1×PBS+5% Tween six times. Color development was then performed with the addition of 50 μl of OPD substrate followed by incubation at RT for 4 minutes. The reaction was then stopped by adding 50 μl of 2.5M H2SO4 and the plate was read at 492 nm wavelength. Positive control sera were obtained from serum samples of adult mice that had been injected with AAV and had previously anti-AAV antibody levels. AAV-treated animals (n=5) and uninjected controls (n=5) were tested four months after administration, four months after administration.

Analysis of Metabolic Profile from Urine and Plasma

The concentrations of guanidino compounds, including creatine, creatinine and guanidinoacetic acid, were determined in plasma or urine samples using Agilent 1260 Liquid Chromatography (LC) combined with triple-quad 6410B Mass Spectrometry (MS) (Santa Clara, CA). Briefly, 10 ul of 1 mM internal standard (IS) epsilon amino caproic acid (EACA) was added to 10 uL of plasma or urine sample. For measuring creatinine, samples were deproteinized, dried down and reconstituted in 0.1% formate in $H_2O$ (Solution A) and used for analysis by LC-MS. For measuring creatine and GAA, plasma or urine sample was derivatized with 3N HCL-Butanol, heated for 15 min. at 60° C., then dried and reconstituted with 100 ul of solution A for LC-MS analysis. Separation was performed with Agilent Poroshell 120 EC-C18 column with mobile phase consistent of solution A and solution B (0.1% formate in acetonitrile and 0.005% TFA). For underivatized samples, we used the MRM, 114-44 and 132-41 for creatinine and internal standard, respectively. For derivatized samples we used the MRM, 188-44, 188-69 and 174-101 for creatinine, GAA and internal standard, respectively.

ALT and AST were determined at CHOP Metabolomic Core using kits from BioVision (Milpitas, CA). (ALT Catalog #K752-100, AST kit Catalog #753-100). Analyses were performed per the manufacturer's instructions with the final measurement with a PerkinElmer spectrometer.

Analysis of Metabolic Profile from Tissues

1. Reagents

Formic acid LC/MS grade and Methanol HPLC grade were purchased from Fisher Scientific (Ottawa, ON). Trichloroacetic acid (TCA) was supplied by VWR International (Radnor, PA) and buthanol·HCL (3M) was from Regis (Morton Grove, IL). Chemicals for calibrators and internal standards, guanidinoacetic acid (GAA), L-arginine (Arg), creatine (CT), creatinine (CTN), ornithine-d6, arginine-d7, creatine-d3, and creatinine-d3 were purchased from Sigma-Aldrich Canada Co. (Oakville, ON). Tubes for tissue homogenisation, VWR 2 mL×2.8 mm Ceramic Hard tissue Homogenizing Mix and VWR 2 mL×1.4 mm Ceramic Soft Tissue Homogenizing Mix were purchased from VWR (VWR International, Radnor, PA).

2. Tissue Metabolites Preparation 30-60 mg of flash frozen kidney, heart or muscle were placed in a 2 mL tube containing 2.8 mm ceramic beads; liver or brain into a 2 mL tube containing 1.4 mm ceramic beads. Tubes were filled with 1 mL of cold water and processed on Omni Bead Raptor Elite at 5.65 m/s for 2 cycles of 1 min with a 10 second dwell time for kidney, heart and muscle and 4.85 m/s for 1 cycle of 20 seconds for liver and brain. Tissue homogenates, 300 μL were mixed with 75 30% TCA, vortexed and spun down at 13,000×rpm for 5 min to precipitate proteins. The cleared tissue homogenates were transferred into Eppendorf tubes and store at −80° C. or processed immediately for metabolites extraction. To extract metabolites for LC-MS/MS, 10 μL of the cleared tissue homogenate was mix with 10 μL of the internal standard and 500 μL methanol. All tubes were vortexed and spun down at 13,000×rpm for 5 min. The supernatant was transferred into a clean glass test tube and loaded onto the Microvap (Organomation, Berlin, MA) at 37° C. to evaporate the excess solvent. Dry residue was dissolved in 100 buthanol·HCL (3M) by vortexing and incubated at 60° C. for 30 min. After cooling to room temperature, derivatized samples were transferred onto the Microvap at 37° C. to evaporate the excess solvent. Dry residue was resuspended in 700 μL methanol and transferred into a 2 mL glass vial.

3. Liquid-Chromatography Tandem Mass Spectrometry (LC-MS/MS)

The method for CT metabolites analysis on LC-MS/MS was adapted with slight modifications from Tran at el. (42). The LC-MS/MS system consisted of an ExionLC AD UHPLC system coupled with QTRAP 6500plus (AB Sciex LLC, Framingham, MA). The metabolites separation was achieved using gradient binary elution at a flow rate of 0.7 mL/min and a temperature at 45° C. on a Kinetex C18 100 Å, 5 μm, 100×4.6 mm LC column (Phenomenex Inc., Torrance, CA). Solvent A consisted of 0.5 mmol/l ammonium formate, 0.1% (v/v) formic acid in water and solvent B consisted of 0.5 mmol/l ammonium formate, 0.1% (v/v) formic acid in methanol. The mobile phase was used at 100% A at 0 min; 100% B at 5.0 min; 100% B at 7.5 min; 100% A at 7.55 min; 100% A at 10 min. The injection volume was 1 μL. The mass spectrometry was performed at the positive ionization and multiple reaction monitoring (MRM) scan mode. The optimal ion transitions were as follows: CT—188.2→90.0, CTN—114.2→44.0, GAA—174.2→101.1, ARG—231.2→172.2, ORN—189.2→70.1, creatine-d3—191.2→93.0, creatinine-d3—117.2→47.0, guanidinoacetate-d2—176.2→103.1, arginine-d7—238.2→179.2, ornithine-d6—195.2→76.1. The ion source parameters were set at TEM—600° C., de-clustering potential—60.0, capillary voltage—5500 V, curtain gas—30, GS1—30, and GS2—20. Data processing and quantification was performed using Analyst 1.7.0 software (AB Sciex LLC, Framingham, MA).

4. Calibrators and Internal Standard (IS) for LC-MS/MS

Calibrators stock solutions were prepared by individually weighing compounds using an analytical balance and dissolving each in water at concentration of 5 mM for CT, ORN, ARG, CTN and 0.1 mM for GAA. Working solutions of calibrators were prepared from stocks by serial dilution to achieve final concentrations of 500, 250, 100, 50, 25, 10, 5, 2.5, 0 μM for CT, ORN, ARG, CTN and 10, 5, 2, 1, 0.5, 0.25, 0.1, 0.05, 0 μM for GAA. The IS was prepared as a mixture of ornithine-d6, arginine-d7, creatine-d3, and creatinine-d3 at concentration of 100 μM and guanidinoacetate-d2 at concentration of 10 μM in water. Calibrators and the IS were stored at −20° C. until use. Analytes were quantified using the signal intensity ratio of the compound to its IS and related to external calibration using the signal intensity ratio of the calibrator to its IS.

Western Blot

General preparation of the protein samples and Western blotting were carried out as described (43). Briefly, liver specimens were homogenized in RIPA buffer containing Halt™ Protease Inhibitor Cocktail (cat 78430, ThermoFisher, Waltham, MA) to isolate proteins. 50 μg of the total protein extract, quantified with Bio-Rad Protein Assay Dye (cat 5000006, BioRad, Hercules, CA), were separated by SDS-PAGE and probed with human GAMT antibody (Abcam, Catalog #ab126736; 1:1000 dilution). HRP-conjugated β-actin antibody (Santa Cruz Biotechnology, Dallas, TX, Catalog #sc-47778; 1:5000) was utilized as loading control. hGAMT was labeled by HRP-conjugated goat anti-rabbit IgG (Santa Cruz Biotechnology, Catalog #sc-2004; 1:5000), and targeted proteins were detected using SuperSignal™ West Pico PLUS Chemiluminescent Substrate (cat PI34579, ThermoFisher).

In Situ Hybridization

RNAscope in situ hybridization was performed using the Bond RX platform (Leica Biosystems) and the RNAscope 2.5 L reagent kit (Advanced Cell Diagnostics (ACD)) according to the manufacturer's protocol (Document Number: 322750-USM). Briefly, freshly cut 4 μm thick paraffin sections were stained. Following heat-induced epitope retrieval (HIER) (ACD HIER 15 min with ER2 at 95° C.) and proteinase digestion (ACD 15 min Protease), the slides were incubated for 2 hours at 40° C. with hGAMT-codon-No-XMm-C1 (ACD-ref 1003128-C1). Amplification steps were performed according to the ACD protocol. The chromogen was detected with the ACD RNAscope 2.5 LSx Reagent Kit-RED (Advanced Cell Diagnostics (ACD), Cat #: 322750). All stained slides were scanned at high magnification (×400) using a whole-slide scanning microscope (Aperio, Leica Biosystems).

GAMT qRT-PCR

Livers were removed from mice, and specimens were snap frozen in liquid nitrogen after being placed in Eppendorf tubes. RNA was extracted from livers with RNeasy Fibrous Tissue Mini Kit according to manufacturer's instructions (Qiagen, 74704). Briefly, tissue was homogenized in buffer then digested with proteinase K before extracting the supernatant containing unpurified RNA. RNA was then isolated by RNeasy column extraction and pure RNA was eluted with RNase-free water.

Once RNA was extracted, cDNA was synthesized with Applied Biosystems High-Capacity cDNA Reverse Transcription Kit with RNase Inhibitor kit (ThermoFisher, 43-749-66) following the manufacturer's instructions. qRT-PCR was performed using SYBR Green Supermix (BioRad, 17256274) and primers specific for the hcoGAMT, taking advantage of base pair differences in exon 1 between the human and mouse variants of GAMT (MluI 19 F (CACACCTTAGGATTCTGGGT (SEQ ID NO: 3)) and MluI R 3 (CCTCCTGAACCTTTGAAGC (SEQ ID NO: 4)) were synthesized. Primers for β-actin (mBeta-Actin F (CTAAGGCCAACCGTGAAAAG (SEQ ID NO: 5)) and mBeta-Actin R (ACCAGAGGCATACAGGGACA (SEQ ID NO: 6)) were used as a reference gene. qRT-PCR was performed for 40 cycles at a melting temperature of 56° C. Fold changes using the—ΔΔCt method were calculated. Animals as n=5 per group with males and females equally represented overall (20 mice).

AAV Copy Number Determination

Unfixed livers were homogenized, and DNA was extracted according to the manufacturer's instructions (Qiagen, 56605223). Standards were made using serial dilution of the parental viral plasmid. Both standards and extracted DNA were then loaded onto 96-well PCR plates (USA Scientific, 21034). qPCR was then performed according to protocol, detected by SYBR Green (Bio-Rad, 1725174). The vector copy number per diploid genome was calculated from equations obtained from the standards and their Ct values. The average of mice per group was used for comparisons.

Histology and Immunohistochemistry of Liver

Portions of explanted livers from euthanized animals were fixed in 10% neutral buffered formalin (v/v) for 48 hours and subsequently stored in 70% ethanol. Standard procedures were employed for processing and paraffin embedding of the tissues. Paraffin-embedded sections were cut at 4 μm thickness and paraffin removed with xylene and rehydrated through graded ethanol. Endogenous peroxidase activity was blocked with 3% hydrogen peroxide in methanol for 10 min. Heat-induced antigen retrieval (HIER) was carried out for all sections in 0.001 M EDTA buffer, pH=8.00 using a Biocare decloaker at 95° C. for 25 min. The slides were then stained with anti-GAMT antibody (ab 126736, 1-100, Abcam, Cambridge, UK); the signal was detected using the Dakocytomation Envision□ System Labelled Polymer HRP anti rabbit (Agilent K4003, ready to use). All sections were visualized with the diaminobenzidine reaction and counterstained with hematoxylin.

Micro-Positron Emission Tomography (PET)/Micro-Computed Tomography (CT) Imaging

Animals were anesthetized with 1.5% vaporized isoflurane, and injected with (18F)-FDG via tail vein. After 60 min (18F)-FDG uptake under a conscious condition, animals underwent micro-PET imaging (10 min static data acquisition) immediately followed by microCT imaging using the Genisys8 PET/CT scanner (Sofie Biosciences). PET data was decay corrected, and attenuation correction was performed using the CT images. Co-registered PET/CT data were analyzed and quantified using AMIDE software. Fat tissues in the CT scans were visualized in the 3D mode using the ORS Dragonfly software. Quantification of FDG uptake in individual areas of the brain was performed using mouse brain atlas previously developed (44).

Behavioral Testing

All behavioral testing included 8 mice per group (4 male and 4 female).

Grip Strength: Grip strength of the mice was assessed to examine muscle strength and stamina. Fore and hindlimb strength is measured using a customized grip strength meter (Chantillon apparatus, San Diego) mounted on a Plexiglas weighted base. Five trials were completed for the forelimbs and the hind limbs with at least one minute of rest between trials. Mice had at least 30 minutes of rest between the forelimb and hindlimb grip strength tests. For both tests, the maximum force was recorded in Newtons. For the forelimb test, the wire mesh grid grip was attached to the grip meter so that it would be parallel to the table surface. The mouse was lifted by the tail lowered so that the forelimbs were grasping the mesh grid and pulled away from the meter parallel to the table by the base of the tail in a quick manner. The results were then recorded and after one minute the test was repeated until 5 trials were achieved. For the hindlimb test, the mesh grid grip was adjusted to sit at a 45 degree angle from the line of the table. The mouse was again held by the base of the tail and allowed to grip the mesh grid with the hind limbs. The angle prevented it from gripping with the forepaws. The mouse was then pulled parallel to the table in a quick manner. After 1 minute, the test was repeated until five trials were achieved.

Barnes Maze: Mice were trained on the Barnes maze as described previously (45, 46). The maze consisted of a grey, non-reflective circular platform (91 cm diameter; Stoelting) with holes around the perimeter (5 cm diameter). Nineteen holes contained shallow, false-escape bottoms and one hole had the escape box. The arena was located in the center of the room with many extra-maze visual cues, including black and white geometric signs, two large lamps for bright light and a speaker for producing white noise.

Each day, the mice were tested in squads of 4. Mice were placed on the center of the table under a 2 L beaker for 30 s before the start of the trial. The first day consisted of one 5 min habituation trial under low light (<20 lux) with no escape and 2 trials under bright-light, where the mouse was guided to the escape box after 3 min of free exploration. Days 2-4 consisted of four 90 s trials with an inter-trial interval of ~15 min, under bright lighting and white noise. The location of the escape box randomly varied by squad, but remained the same for each squad across training days. If mice did not enter the escape box by the end of the trial, they were guided to the escape box by the experimenter. Once the mouse entered the escape box, they were left for 30 s before being returned to their home cage. On days 6 and 13, mice were given a probe trial to assess short and long-term memory, respectively. For the probe trial, all holes contained the false-escape bottom, and mice were allowed to explore for 90 s.

All videos were recorded and analyzed using AnyMaze software (Stoelting). Because mice are more hesitant to enter the escape box, latency to first head entry (i.e., primary latency) into the escape box was used to assess learning (45). Additionally, each training trial was scored for the approach used to find the hole (e.g., direct, serial, or random). A direct approach was scored when the mouse moved towards the escape (within 2 holes of the escape box), and likely reflects the use of extra-maze cues and spatial memory to find the escape. A serial approach was scored when the mouse approached a hole more than 2 holes from the escape box and continued around the perimeter of the maze to find the escape. A random approach was scored when the mouse was more than 2 holes from the escape box and visited no more than 3 holes in a row to find the escape.

Statistical Evaluation

All collected data was analyzed with the GraphPad Prism v.9.0.1 (GraphPad Software, San Diego, CA) statistical package. All numerical data were expressed as mean±standard deviation (SD) except where noted otherwise, and p values, considered significant when <0.05, were determined using one-way ANOVA with Tukey's multiple comparison's test (i.e. for quantitative real-time PCR), or two-way ANOVA with Dunnett's multiple comparison's test. Error bars represent SD.

FIG. 1 provides a schematic of a map of the vector "pAAV-TBG-hGAMT-TV1co".

```
pAAv Sequence:
                                      (SEQ ID NO: 7)
gctgcgcgctcgctcgctcactgaggccgcccgggcaaag

cccgggcgtcgggcgacctttggtcgcccggcctcagtga

gcgagcgagcgcgcagagagggagtggccaactccatcac

taggggttccttgtagttaatgattaacccgccatgctac

ttatctaccagggtaatggggatcctctagaactatagct

agaattcgcccttaagctagcaggttaatttttaaaaagc

agtcaaaagtccaagtggcccttggcagcatttactctct

ctgtttgctctggttaataatctcaggagcacaaacattc

cagatccaggttaatttttaaaaagcagtcaaaagtccaa

gtggcccttggcagcatttactctctctgtttgctctggt

taataatctcaggagcacaaacattccagatccggcgcgc

cACACCCAAATATGGCTCGCGCTCTAAAAATAACCCTGGG

ACACCCGAGATGCCTGGTTATAATTAACCCAGACATGTGG

CTGCCCCCCCCAACACCTGCTGCCGCTCACAAGTGTTGCA

TTCCTCTCTGCCCGCTCCTTCTTTGGTCACAGAGAGGAAT

GCAACACTTGTGAGCCAGAGAGGAATGCAACACTTGTGAG

CCGCTCTAAAAATAACCCTGAACACCCAAATATGGCTCGG

GCCAGCTGTCCCCCGCATGCGGCCCCTCCCTGGGGAGGGC

CCCTCCTGGCTAGTCACACCCTGTAGGCTCCTCTATATAA

CCCAGGGGCACAGGGGCTGCCCCCGGGTCACCACCACCTC

CACAGCACAGACAGACACTCAGGAGCCAGCCAGCacgcgt

catatgttaattaagccgccaccatgtccgccccttcagc

cacccccatcttcgcccccggggaaaactgtagtccagca

tggggcgccgcaccagccgcctacgatgccgccgacacac

accttaggattctgggtaaacctgtaatggaacgatggga

gacccccctatatgcacgcactcgcagccgccgcctcttcc

aaaggagggcgcgttcttgaagtcggctttggaatggcga

tcgcagcttcaaaggttcaggaggcccctattgatgagca

ttggataattgaatgtaatgatggtgtgtttcagagattg

cgggattgggccccaagacaaacacacaaggttatacctc

ttaaaggactgtgggaagacgtcgcgccaactctccctga

tggacactttgacggcattttgtatgacacctacccccctc

tccgaagaaacatggcacacgcatcagttcaactttatta

aaaatcacgcttttcgactcctcaaaccgggtggagtcct

cacatactgcaacttgacatcttggggtgaacttatgaaa

tctaaatattccgatatcaccataatgttcgaggagaccc
```

-continued aagtgccagcgctccttgaggccggttttagacgcgaaaa catcagaactgaagtcatggcgcttgtgcccccgccgat tgccgctattatgcctttcctcaaatgattaccccacttg tgacaaaaggttaggcggccgcggtacctctagagtcgac ccgggcggcctcgaggacggggtgaactacgcctgaggat ccgatctttttccctctgccaaaaattatggggacatcat gaagccccttgagcatctgacttctggctaataaaggaaa tttattttcattgcaatagtgtgttggaattttttgtgtc tctcactcggaagcaattcgttgatctgaatttcgaccac ccataatacccattaccctggtagataagtagcatggcgg gttaatcattaactacaaggaacccctagtgatggagttg gccactccctctctgcgcgctcgctcgctcactgaggccg ggcgaccaaaggtcgcccgacgcccgggctttgcccgggc ggcctcagtgagcgagcgagcgcgcagccttaattaacct aattcactggccgtcgttttacaacgtcgtgactgggaaa accctggcgttacccaacttaatcgccttgcagcacatcc ccctttcgccagctggcgtaatagcgaagaggcccgcacc gatcgcccttcccaacagttgcgcagcctgaatggcgaat gggacgcgccctgtagcggcgcattaagcgcggcgggtgt ggtggttacgcgcagcgtgaccgctacacttgccagcgcc ctagcgcccgctcctttcgctttcttcccttcctttctcg ccacgttcgccggctttccccgtcaagctctaaatcgggg gctccctttagggttccgatttagtgctttacggcacctc gaccccaaaaaacttgattagggtgatggttcacgtagtg ggccatcgccctgatagacggtttttcgccctttgacgtt ggagtccacgttctttaatagtggactcttgttccaaact ggaacaacactcaaccctatctcggtctattcttttgatt tataagggattttgccgatttcggcctattggttaaaaaa tgagctgatttaacaaaaatttaacgcgaattttaacaaa atattaacgcttacaatttaggtggcacttttcggggaaa tgtgcgcggaacccctatttgtttatttttctaaatacat tcaaatatgtatccgctcatgagacaataaccctgataaa tgcttcaataatattgaaaaaggaagagtatgagtattca acatttccgtgtcgcccttattcccttttttgcggcattt tgccttcctgtttttgctcacccagaaacgctggtgaaag taaaagatgctgaagatcagttgggtgcacgagtgggtta catcgaactggatctcaacagcggtaagatccttgagagt tttcgccccgaagaacgttttccaatgatgagcacttttaaagttctgctatgtggcgcggtattatcccgtattgacgc cgggcaagagcaactcggtcgccgcatacactattctcag aatgacttggttgagtactcaccagtcacagaaaagcatc ttacggatggcatgacagtaagagaattatgcagtgctgc cataaccatgagtgataacactgcggccaacttacttctg acaacgatcggaggaccgaaggagctaaccgcttttttgc acaacatgggggatcatgtaactcgccttgatcgttggga accggagctgaatgaagccataccaaacgacgagcgtgac accacgatgcctgtagcaatggcaacaacgttgcgcaaac tattaactggcgaactacttactctagcttcccggcaaca attaatagactggatggaggcggataaagttgcaggacca cttctgcgctcggcccttccggctggctggtttattgctg ataaatctggagccggtgagcgtgggtctcgcggtatcat tgcagcactggggccagatggtaagccctcccgtatcgta gttatctacacgacggggagtcaggcaactatggatgaac gaaatagacagatcgctgagataggtgcctcactgattaa gcattggtaactgtcagaccaagtttactcatatatactt tagattgatttaaaacttcatttttaatttaaaaggatct aggtgaagatcctttttgataatctcatgaccaaaatccc ttaacgtgagttttcgttccactgagcgtcagaccccgta gaaaagatcaaaggatcttcttgagatcctttttttctgc gcgtaatctgctgcttgcaaacaaaaaaaccaccgctacc agcggtggtttgtttgccggatcaagagctaccaactctt tttccgaaggtaactggcttcagcagagcgcagataccaa atactgttcttctagtgtagccgtagttaggccaccactt caagaactctgtagcaccgcctacatacctcgctctgcta atcctgttaccagtggctgctgccagtggcgataagtcgt gtcttaccgggttggactcaagacgatagttaccggataa ggcgcagcggtcgggctgaacggggggttcgtgcacacag cccagcttggagcgaacgacctacaccgaactgagatacc tacagcgtgagctatgagaaagcgccacgcttcccgaagg gagaaaggcggacaggtatccggtaagcggcagggtcgga acaggagagcgcacgagggagcttccagggggaaacgcct ggtatctttatagtcctgtcgggtttcgccacctctgact tgagcgtcgatttttgtgatgctcgtcaggggggcggagc ctatggaaaaacgccagcaacgcggcctttttacggttcc tggccttttgctggccttttgctcacatgttctttcctgc gttatcccctgattctgtggataaccgtattaccgccttt gagtgagctgataccgctcgccgcagccgaacgaccgagc gcagcgagtcagtgagcgaggaagcggaagagcgcccaat -continued

```
acgcaaaccgcctctccccgcgcgttggccgattcattaa

tgcagctggcacgacaggtttcccgactggaaagcgggca

gtgagcgcaacgcaattaatgtgagttagctcactcatta

ggcaccccaggctttacactttatgcttccggctcgtatg

ttgtgtggaattgtgagcggataacaatttcacacaggaa

acagctatgaccatgattacgccagatttaattaaggcct

taattag
```

Example 2: Materials Methods and Studies on Ameliorating SLC6A8 Creatine Deficiency Disorder We have designed illustrative gene constructs with 1) a constitutive/ubiquitous promoter (chicken b-actin promoter) (named pAAV-CAG SLC6A8TV1 BH) and 2) a neuron-specific promoter (human synapsin) (named pAAV-hSyn SLC6A8TV1 BH).

Figure 2:
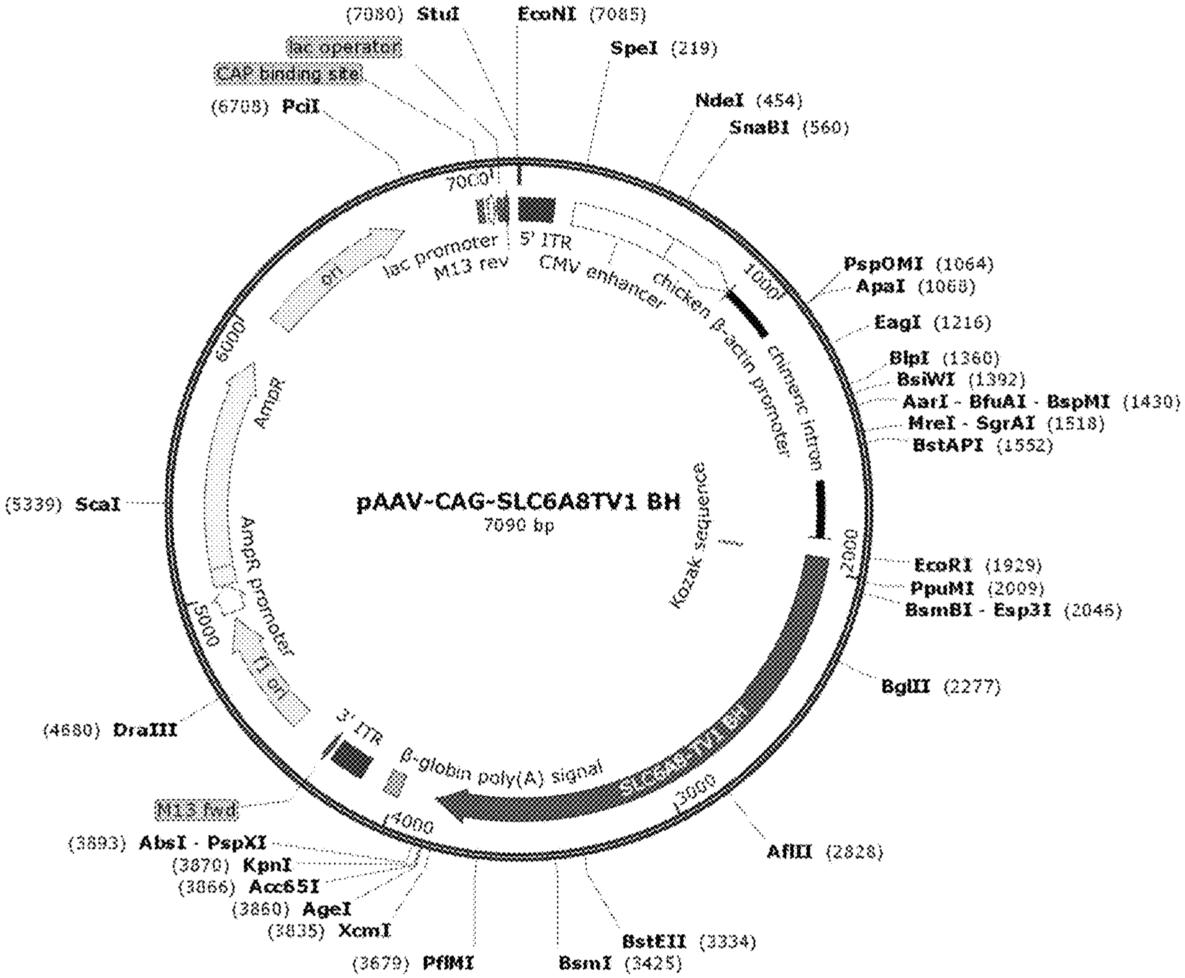
FIG. 2 provides a schematic of a map of the vector "pAAV-CAG-SLC6A8TV1 BH" including certain restriction endonuclease cleavage sites and vector elements.

FIG. 2 provides a schematic of a map of the vector "pAAV-CAG-SLC6A8TV1 BH". Plasmid Length: 7090 bp. Viral Genome Length (including ITRs): 4269 bp. Promoter: CAG. PolyA: Yes, β-globin polyA signal. BH as synthesized by Blue Heron.

Sequence: ITRs highlighted in bold (SEQ ID NO: 8)

GCTGCGCGCTCGCTCGCTCACTGAGGCCGCCCGGGCAAAGCCCGGGCGTCGGGCGACCTT

TGGTCGCCCGGCCTCAGTGAGCGAGCGAGCGCGCAGAGAGGGAGTGGCCAACTCCATCAC

TAGGGGTTCCTTGTAGTTAATGATTAACCCGCCATGCTACTTATCTACCAGGGTAATGGG

GATCCTCTAGAACTATAGCTAGTCGACATTGATTATTGACTAGTTATTAATAGTAATCAA

TTACGGGGTCATTAGTTCATAGCCCATATATGGAGTTCCGCGTTACATAACTTACGGTAA

ATGGCCCGCCTGGCTGACCGCCCAACGACCCCCGCCCATTGACGTCAATAATGACGTATG

TTCCCATAGTAACGCCAATAGGGACTTTCCATTGACGTCAATGGGTGGAGTATTTACGGT

AAACTGCCCACTTGGCAGTACATCAAGTGTATCATATGCCAAGTACGCCCCCTATTGACG

TCAATGACGGTAAATGGCCCGCCTGGCATTATGCCCAGTACATGACCTTATGGGACTTTC

CTACTTGGCAGTACATCTACGTATTAGTCATCGCTATTACCATGGTCGAGGTGAGCCCCA

CGTTCTGCTTCACTCTCCCCATCTCCCCCCCCTCCCCACCCCCAATTTTGTATTTATTTA

TTTTTTAATTATTTTGTGCAGCGATGGGGGCGGGGGGGGGGGGGGGGCGCGCGCCAGGCG

GGGCGGGGCGGGGCGAGGGGCGGGGCGGGGCGAGGCGGAGAGGTGCGGCGGCAGCCAATC

AGAGCGGCGCGCTCCGAAAGTTTCCTTTTATGGCGAGGCGGCGGCGGCGGCGGCCCTATA

AAAAGCGAAGCGCGCGGCGGGCGGGAGTCGCTGCGCGCTGCCTTCGCCCCGTGCCCCGCT

CCGCCGCCGCCTCGCGCCGCCCGCCCCGGCTCTGACTGACCGCGTTACTCCCACAGGTGA

GCGGGCGGGACGGCCCTTCTCCTCCGGGCTGTAATTAGCGCTTGGTTTAATGACGGCTTG

TTTCTTTTCTGTGGCTGCGTGAAAGCCTTGAGGGGCTCCGGGAGGGCCCTTTGTGCGGGG

GGAGCGGCTCGGGGGGTGCGTGCGTGTGTGTGTGCGTGGGGAGCGCCGCGTGCGGCTCCG

CGCTGCCCGGCGGCTGTGAGCGCTGCGGGCGCGGCGCGGGGCTTTGTGCGCTCCGCAGTG

TGCGCGAGGGGAGCGCGGCCGGGGGCGGTGCCCCGCGGTGCGGGGGGGGCTGCGAGGGGA

ACAAAGGCTGCGTGCGGGGTGTGTGCGTGGGGGGGTGAGCAGGGGGTGTGGGCGCGTCGG

TCGGGCTGCAACCCCCCCTGCACCCCCCTCCCCGAGTTGCTGAGCACGGCCCGGCTTCGG

GTGCGGGGCTCCGTACGGGGCGTGGCGCGGGGCTCGCCGTGCCGGGCGGGGGGTGGCGGC

AGGTGGGGGTGCCGGGCGGGGCGGGGCCGCCTCGGGCCGGGGAGGGCTCGGGGGAGGGGC

GCGGCGGCCCCCGGAGCGCCGGCGGCTGTCGAGGCGCGGCGAGCCGCAGCCATTGCCTTT

TATGGTAATCGTGCGAGAGGGCGCAGGGACTTCCTTTGTCCCAAATCTGTGCGGAGCCGA

AATCTGGGAGGCGCCGCCGCACCCCCTCTAGCGGGCGCGGGGCGAAGCGGTGCGGCGCCG

GCAGGAAGGAAATGGGGGGGGAGGGCCTTCGTGCGTCGCCGCGCCGCCGTCCCCTTCTCC

CTCTCCAGCCTCGGGGCTGTCCGCGGGGGGACGGCTGCCTTCGGGGGGGACGGGGCAGGG

CGGGGTTCGGCTTCTGGCGTGTGACCGGCGGCTCTAGAGCCTCTGCTAACCATGTTCATG

-continued

CCTTCTTCTTTTTCCTACAGCTCCTGGGCAACGTGCTGGTTATTGTGCTGTCTCATCATT

TTGGCAAAGAATTCTTAATTAAGCCGCCACCATGGCAAAGAAAAGCGCTGAAAATGGTAT

CTACAGCGTCAGTGGGGATGAGAAGAAAGGACCTTTGATCGCACCTGGACCAGACGGAGC

ACCCGCCAAGGGAGACGGGCCTGTGGGCCTTGGGACACCAGGGGGTCGCCTTGCGGTGCC

ACCTCGAGAGACCTGGACCCGGCAAATGGATTTCATAATGAGTTGCGTAGGTTTTGCTGT

GGGACTCGGTAACGTGTGGCGGTTCCCCTATCTGTGCTACAAAAACGGGGGAGGCGTTTT

CCTCATACCCTATGTGCTGATCGCCCTCGTCGGAGGTATTCCAATTTTCTTTCTGGAGAT

CTCCCTGGGCCAATTTATGAAAGCTGGAAGCATCAACGTGTGGAACATCTGTCCTCTGTT

TAAAGGTCTGGGTTATGCGTCAATGGTGATTGTGTTTTATTGTAACACCTACTATATCAT

GGTATTGGCGTGGGGATTTTACTATCTGGTGAAGAGTTTCACAACAACCCTCCCCTGGGC

CACATGCGGCCATACATGGAACACACCAGATTGTGTCGAAATCTTTCGGCATGAAGACTG

TGCGAACGCTTCTCTGGCCAATCTGACTTGCGACCAGTTGGCCGATAGAAGGAGTCCTGT

CATCGAATTTTGGGAAAACAAGGTGTTGCGGCTGTCTGGCGGACTGGAGGTTCCGGGGGC

ACTGAACTGGGAGGTTACGTTGTGCCTGCTGGCCTGCTGGGTCTTGGTATACTTCTGTGT

GTGGAAGGGAGTGAAATCTACCGGGAAGATTGTTTATTTTACTGCGACCTTTCCTTACGT

CGTGCTCGTGGTGCTGCTGGTTAGAGGAGTGTTGCTCCCCGGGGCACTGGATGGCATCAT

CTATTATCTTAAGCCCGATTGGAGCAAGCTCGGCTCACCTCAGGTTTGGATTGATGCTGG

CACACAGATTTTCTTTAGTTATGCAATCGGATTGGGCGCATTGACCGCCCTCGGCAGTTA

CAACCGCTTCAACAACAACTGTTACAAAGATGCCATAATACTCGCTCTGATAAATAGTGG

TACTTCCTTTTTTGCGGGTTTTGTTGTTTTTTCAATCCTGGGGTTTATGGCAGCAGAGCA

GGGTGTCCACATTTCCAAAGTGGCGGAGAGCGGTCCCGGACTTGCCTTTATCGCGTACCC

AAGAGCCGTCACACTGATGCCCGTCGCCCCTCTCTGGGCTGCCCTGTTTTTTTTTATGTT

GTTGCTTCTGGGACTCGATTCTCAGTTTGTCGGAGTGGAGGGCTTTATAACCGGACTCCT

TGACTTGCTCCCCGCGTCTTACTACTTCAGATTCCAGCGCGAGATTTCTGTCGCCCTGTG

CTGCGCTCTGTGTTTTGTGATCGACCTCTCAATGGTTACCGACGGCGGGATGTATGTCTT

TCAGCTCTTCGATTACTACTCTGCCTCAGGAACAACTTTGCTCTGGCAGGCTTTCTGGGA

ATGCGTTGTAGTTGCTTGGGTTTATGGCGCTGATAGATTTATGGATGACATCGCGTGTAT

GATAGGCTATCGCCCCTGCCCCTGGATGAAATGGTGTTGGTCATTTTTCACACCCTTGGT

ATGTATGGGTATCTTCATTTTTAACGTTGTATACTACGAACCACTCGTCTACAATAACAC

CTACGTCTACCCATGGTGGGGAGAAGCGATGGGATGGGCCTTTGCCCTGTCTTCTATGTT

GTGTGTGCCACTCCACCTGTTGGGTTGTCTCCTTAGGGCTAAAGGAACCATGGCCGAGCG

CTGGCAGCATCTGACTCAGCCTATATGGGGCTTGCATCATCTGGAATATAGAGCGCAGGA

TGCCGACGTCCGCGGCCTCACTACTCTCACACCTGTTTCTGAGTCCTCCAAAGTAGTTGT

GGTTGAATCAGTAATGTAAACCGGTGGTACCTCTAGAGTCGACCCGGGCGGCCTCGAGGA

CGGGGTGAACTACGCCTGAGGATCCGATCTTTTTCCCTCTGCCAAAAATTATGGGGACAT

CATGAAGCCCCTTGAGCATCTGACTTCTGGCTAATAAAGGAAATTTATTTTCATTGCAAT

AGTGTGTTGGAATTTTTTGTGTCTCTCACTCGGAAGCAATTCGTTGATCTGAATTTCGAC

CACCCATAATACCCATTACCCTGGTAGATAAGTAGCATGGCGGGTTAATCATTAACTACA

AGGAACCCCTAGTGATGGAGTTGGCCACTCCCTCTCTGCGCGCTCGCTCGCTCACTGAGG

CCGGGCGACCAAAGGTCGCCCGACGCCCGGGCTTTGCCCGGGCGGCCTCAGTGAGCGAGC

-continued

GAGCGCGCAGCCTTAATTAACCTAATTCACTGGCCGTCGTTTTACAACGTCGTGACTGGG

AAAACCCTGGCGTTACCCAACTTAATCGCCTTGCAGCACATCCCCCTTTCGCCAGCTGGC

GTAATAGCGAAGAGGCCCGCACCGATCGCCCTTCCCAACAGTTGCGCAGCCTGAATGGCG

AATGGGACGCGCCCTGTAGCGGCGCATTAAGCGCGGCGGGTGTGGTGGTTACGCGCAGCG

TGACCGCTACACTTGCCAGCGCCCTAGCGCCCGCTCCTTTCGCTTTCTTCCCTTCCTTTC

TCGCCACGTTCGCCGGCTTTCCCCGTCAAGCTCTAAATCGGGGGCTCCCTTTAGGGTTCC

GATTTAGTGCTTTACGGCACCTCGACCCCAAAAAACTTGATTAGGGTGATGGTTCACGTA

GTGGGCCATCGCCCTGATAGACGGTTTTTCGCCCTTTGACGTTGGAGTCCACGTTCTTTA

ATAGTGGACTCTTGTTCCAAACTGGAACAACACTCAACCCTATCTCGGTCTATTCTTTTG

ATTTATAAGGGATTTTGCCGATTTCGGCCTATTGGTTAAAAAATGAGCTGATTTAACAAA

AATTTAACGCGAATTTTAACAAAATATTAACGCTTACAATTTAGGTGGCACTTTTCGGGG

AAATGTGCGCGGAACCCCTATTTGTTTATTTTTCTAAATACATTCAAATATGTATCCGCT

CATGAGACAATAACCCTGATAAATGCTTCAATAATATTGAAAAAGGAAGAGTATGAGTAT

TCAACATTTCCGTGTCGCCCTTATTCCCTTTTTTGCGGCATTTTGCCTTCCTGTTTTTGC

TCACCCAGAAACGCTGGTGAAAGTAAAAGATGCTGAAGATCAGTTGGGTGCACGAGTGGG

TTACATCGAACTGGATCTCAACAGCGGTAAGATCCTTGAGAGTTTTCGCCCCGAAGAACG

TTTTCCAATGATGAGCACTTTTAAAGTTCTGCTATGTGGCGCGGTATTATCCCGTATTGA

CGCCGGGCAAGAGCAACTCGGTCGCCGCATACACTATTCTCAGAATGACTTGGTTGAGTA

CTCACCAGTCACAGAAAAGCATCTTACGGATGGCATGACAGTAAGAGAATTATGCAGTGC

TGCCATAACCATGAGTGATAACACTGCGGCCAACTTACTTCTGACAACGATCGGAGGACC

GAAGGAGCTAACCGCTTTTTTGCACAACATGGGGGATCATGTAACTCGCCTTGATCGTTG

GGAACCGGAGCTGAATGAAGCCATACCAAACGACGAGCGTGACACCACGATGCCTGTAGC

AATGGCAACAACGTTGCGCAAACTATTAACTGGCGAACTACTTACTCTAGCTTCCCGGCA

ACAATTAATAGACTGGATGGAGGCGGATAAAGTTGCAGGACCACTTCTGCGCTCGGCCCT

TCCGGCTGGCTGGTTTATTGCTGATAAATCTGGAGCCGGTGAGCGTGGGTCTCGCGGTAT

CATTGCAGCACTGGGGCCAGATGGTAAGCCCTCCCGTATCGTAGTTATCTACACGACGGG

GAGTCAGGCAACTATGGATGAACGAAATAGACAGATCGCTGAGATAGGTGCCTCACTGAT

TAAGCATTGGTAACTGTCAGACCAAGTTTACTCATATATACTTTAGATTGATTTAAAACT

TCATTTTTAATTTAAAAGGATCTAGGTGAAGATCCTTTTTGATAATCTCATGACCAAAAT

CCCTTAACGTGAGTTTTCGTTCCACTGAGCGTCAGACCCCGTAGAAAAGATCAAAGGATC

TTCTTGAGATCCTTTTTTTCTGCGCGTAATCTGCTGCTTGCAAACAAAAAAACCACCGCT

ACCAGCGGTGGTTTGTTTGCCGGATCAAGAGCTACCAACTCTTTTTCCGAAGGTAACTGG

CTTCAGCAGAGCGCAGATACCAAATACTGTTCTTCTAGTGTAGCCGTAGTTAGGCCACCA

CTTCAAGAACTCTGTAGCACCGCCTACATACCTCGCTCTGCTAATCCTGTTACCAGTGGC

TGCTGCCAGTGGCGATAAGTCGTGTCTTACCGGGTTGGACTCAAGACGATAGTTACCGGA

TAAGGCGCAGCGGTCGGGCTGAACGGGGGGTTCGTGCACACAGCCCAGCTTGGAGCGAAC

GACCTACACCGAACTGAGATACCTACAGCGTGAGCTATGAGAAAGCGCCACGCTTCCCGA

AGGGAGAAAGGCGGACAGGTATCCGGTAAGCGGCAGGGTCGGAACAGGAGAGCGCACGAG

GGAGCTTCCAGGGGGAAACGCCTGGTATCTTTATAGTCCTGTCGGGTTTCGCCACCTCTG

ACTTGAGCGTCGATTTTTGTGATGCTCGTCAGGGGGGCGGAGCCTATGGAAAAACGCCAG

CAACGCGGCCTTTTTACGGTTCCTGGCCTTTTGCTGGCCTTTTGCTCACATGTTCTTTCC

-continued

TGCGTTATCCCCTGATTCTGTGGATAACCGTATTACCGCCTTTGAGTGAGCTGATACCGC

TCGCCGCAGCCGAACGACCGAGCGCAGCGAGTCAGTGAGCGAGGAAGCGGAAGAGCGCCC

AATACGCAAACCGCCTCTCCCCGCGCGTTGGCCGATTCATTAATGCAGCTGGCACGACAG

GTTTCCCGACTGGAAAGCGGGCAGTGAGCGCAACGCAATTAATGTGAGTTAGCTCACTCA

TTAGGCACCCCAGGCTTTACACTTTATGCTTCCGGCTCGTATGTTGTGTGGAATTGTGAG

CGGATAACAATTTCACACAGGAAACAGCTATGACCATGATTACGCCAGATTTAATTAAGG

CCTTAATTAG

Figure 3:
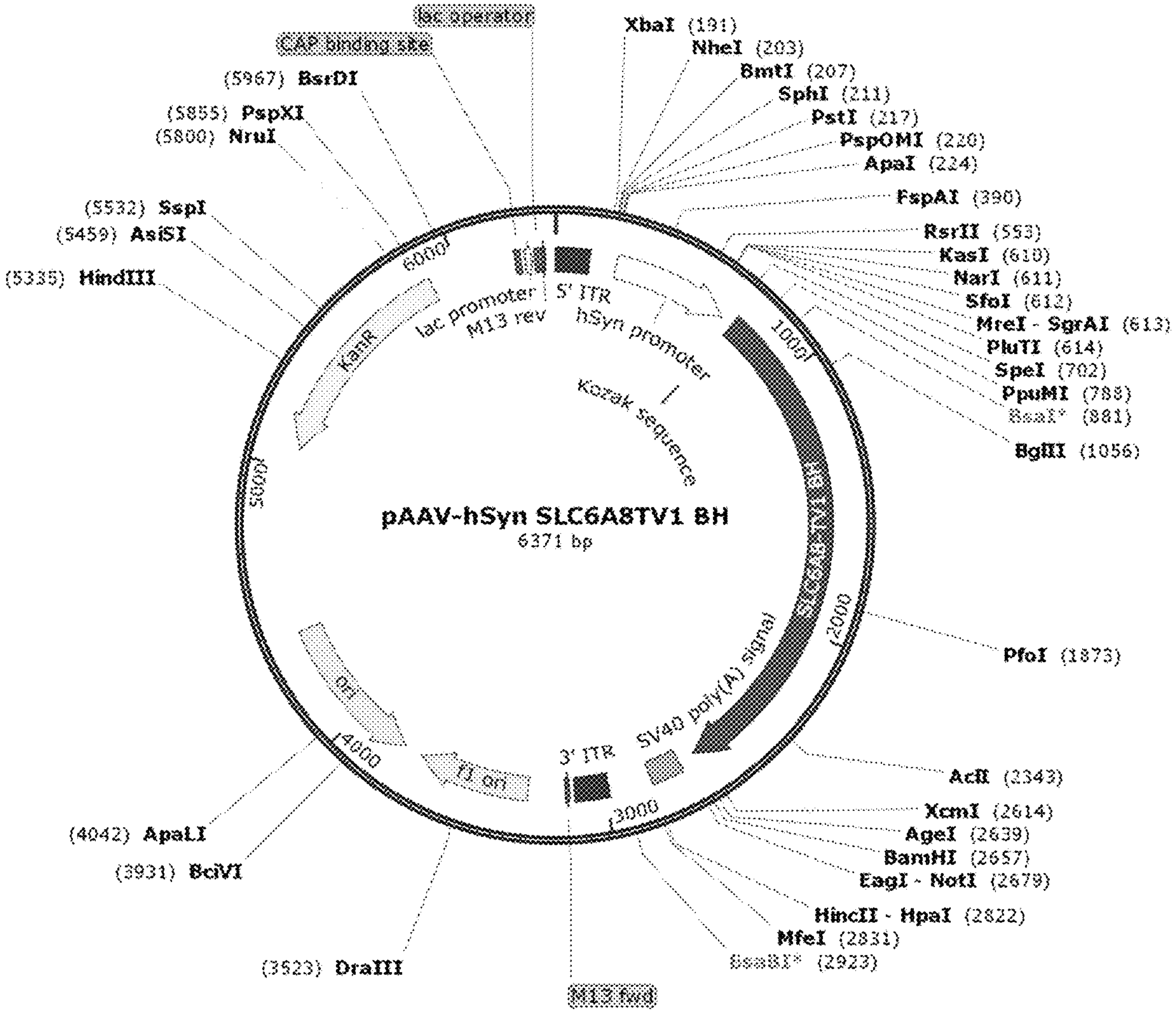
FIG. 3 provides a schematic of a map of the vector "pAAV-hSyn SLC6A8TV1 BH" including certain restriction endonuclease cleavage sites and vector elements.

FIG. 3 provides a schematic of a map of the vector "pAAV-hSyn SLC6A8TV1 BH". Plasmid Length: 6371 bp. Viral Genome Length (including ITRs): 3113 bp. Promoter: hSynapsin PolyA: Yes, SV40 polyA signal. BH=Blue Heron who synthesized this Transcript Variant of SLC6A8.

Sequence: ITRs highlighted in bold (SEQ ID NO: 9)

CTGCGCGCTCGCTCGCTCACTGAGGCCGCCCGGGCAAAGCCCGGGCGTCGGGCGACCTTT

GGTCGCCCGGCCTCAGTGAGCGAGCGAGCGCGCAGAGAGGGAGTGGCCAACTCCATCACT

AGGGGTTCCTTGTAGTTAATGATTAACCCGCCATGCTACTTATCTACGTAGCCATGCTCT

AGGAAGATCCTCTAGAACTATAGCTAGCATGCCTGCAGAGGGCCCTGCGTATGAGTGCAA

GTGGGTTTTAGGACCAGGATGAGGCGGGGTGGGGGTGCCTACCTGACGACCGACCCCGAC

CCACTGGACAAGCACCCAACCCCCATTCCCCAAATTGCGCATCCCCTATCAGAGAGGGGG

AGGGGAAACAGGATGCGGCGAGGCGCGTGCGCACTGCCAGCTTCAGCACCGCGGACAGTG

CCTTCGCCCCCGCCTGGCGGCGCGCGCCACCGCCGCCTCAGCACTGAAGGCGCGCTGACG

TCACTCGCCGGTCCCCCGCAAACTCCCCTTCCCGGCCACCTTGGTCGCGTCCGCGCCGCC

GCCGGCCCAGCCGGACCGCACCACGCGAGGCGCGAGATAGGGGGGCACGGGCGCGACCAT

CTGCGCTGCGGCGCCGGCGACTCAGCGCTGCCTCAGTCTGCGGTGGGCAGCGGAGGAGTC

GTGTCGTGCCTGAGAGCGCAGTCGAATTCGGTACCCTTAAGACTAGTGAATTCTTAATTA

AGCCGCCACCATGGCAAAGAAAAGCGCTGAAAATGGTATCTACAGCGTCAGTGGGGATGA

GAAGAAAGGACCTTTGATCGCACCTGGACCAGACGGAGCACCCGCCAAGGGAGACGGGCC

TGTGGGCCTTGGGACACCAGGGGGTCGCCTTGCGGTGCCACCTCGAGAGACCTGGACCCG

GCAAATGGATTTCATAATGAGTTGCGTAGGTTTTGCTGTGGGACTCGGTAACGTGTGGCG

GTTCCCCTATCTGTGCTACAAAAACGGGGGAGGCGTTTTCCTCATACCCTATGTGCTGAT

CGCCCTCGTCGGAGGTATTCCAATTTTCTTTCTGGAGATCTCCCTGGGCCAATTTATGAA

AGCTGGAAGCATCAACGTGTGGAACATCTGTCCTCTGTTTAAAGGTCTGGGTTATGCGTC

AATGGTGATTGTGTTTTATTGTAACACCTACTATATCATGGTATTGGCGTGGGGATTTTA

CTATCTGGTGAAGAGTTTCACAACAACCCTCCCCTGGGCCACATGCGGCCATACATGGAA

CACACCAGATTGTGTCGAAATCTTTCGGCATGAAGACTGTGCGAACGCTTCTCTGGCCAA

TCTGACTTGCGACCAGTTGGCCGATAGAAGGAGTCCTGTCATCGAATTTTGGGAAAACAA

GGTGTTGCGGCTGTCTGGCGGACTGGAGGTTCCGGGGGCACTGAACTGGGAGGTTACGTT

GTGCCTGCTGGCCTGCTGGGTCTTGGTATACTTCTGTGTGTGGAAGGGAGTGAAATCTAC

CGGGAAGATTGTTTATTTTACTGCGACCTTTCCTTACGTCGTGCTCGTGGTGCTGCTGGT

TAGAGGAGTGTTGCTCCCCGGGGCACTGGATGGCATCATCTATTATCTTAAGCCCGATTG

GAGCAAGCTCGGCTCACCTCAGGTTTGGATTGATGCTGGCACACAGATTTTCTTTAGTTA

-continued

TGCAATCGGATTGGGCGCATTGACCGCCCTCGGCAGTTACAACCGCTTCAACAACAACTG

TTACAAAGATGCCATAATACTCGCTCTGATAAATAGTGGTACTTCCTTTTTTGCGGGTTT

TGTTGTTTTTTCAATCCTGGGGTTTATGGCAGCAGAGCAGGGTGTCCACATTTCCAAAGT

GGCGGAGAGCGGTCCCGGACTTGCCTTTATCGCGTACCCAAGAGCCGTCACACTGATGCC

CGTCGCCCCTCTCTGGGCTGCCCTGTTTTTTTTTATGTTGTTGCTTCTGGGACTCGATTC

TCAGTTTGTCGGAGTGGAGGGCTTTATAACCGGACTCCTTGACTTGCTCCCCGCGTCTTA

CTACTTCAGATTCCAGCGCGAGATTTCTGTCGCCCTGTGCTGCGCTCTGTGTTTTGTGAT

CGACCTCTCAATGGTTACCGACGGCGGGATGTATGTCTTTCAGCTCTTCGATTACTACTC

TGCCTCAGGAACAACTTTGCTCTGGCAGGCTTTCTGGGAATGCGTTGTAGTTGCTTGGGT

TTATGGCGCTGATAGATTTATGGATGACATCGCGTGTATGATAGGCTATCGCCCCTGCCC

CTGGATGAAATGGTGTTGGTCATTTTTCACACCCTTGGTATGTATGGGTATCTTCATTTT

TAACGTTGTATACTACGAACCACTCGTCTACAATAACACCTACGTCTACCCATGGTGGGG

AGAAGCGATGGGATGGGCCTTTGCCCTGTCTTCTATGTTGTGTGTGCCACTCCACCTGTT

GGGTTGTCTCCTTAGGGCTAAAGGAACCATGGCCGAGCGCTGGCAGCATCTGACTCAGCC

TATATGGGGCTTGCATCATCTGGAATATAGAGCGCAGGATGCCGACGTCCGCGGCCTCAC

TACTCTCACACCTGTTTCTGAGTCCTCCAAAGTAGTTGTGGTTGAATCAGTAATGTAAAC

CGGTGGTACCACGCGTGGATCCAACGCGTAGGTACCGGCGGCCGCTTCGAGCAGACATGA

TAAGATACATTGATGAGTTTGGACAAACCACAACTAGAATGCAGTGAAAAAAATGCTTTA

TTTGTGAAATTTGTGATGCTATTGCTTTATTTGTAACCATTATAAGCTGCAATAAACAAG

TTAACAACAACAATTGCATTCATTTTATGTTTCAGGTTCAGGGGGAGATGTGGGAGGTTT

TTTAAAGCAAGTAAAACCTCTACAAATGTGGTAAAATCGATAAGGATCTTCCTAGAGCAT

GGCTACGTAGATAAGTAGCATGGCGGGTTAATCATTAACTACAAGGAACCCCTAGTGATG

GAGTTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGCCTTAAT

TAACCTAATTCACTGGCCGTCGTTTTACAACGTCGTGACTGGGAAAACCCTGGCGTTACC

CAACTTAATCGCCTTGCAGCACATCCCCCTTTCGCCAGCTGGCGTAATAGCGAAGAGGCC

CGCACCGATCGCCCTTCCCAACAGTTGCGCAGCCTGAATGGCGAATGGGACGCGCCCTGT

AGCGGCGCATTAAGCGCGGCGGGTGTGGTGGTTACGCGCAGCGTGACCGCTACACTTGCC

AGCGCCCTAGCGCCCGCTCCTTTCGCTTTCTTCCCTTCCTTTCTCGCCACGTTCGCCGGC

TTTCCCCGTCAAGCTCTAAATCGGGGGCTCCCTTTAGGGTTCCGATTTAGTGCTTTACGG

CACCTCGACCCCAAAAAACTTGATTAGGGTGATGGTTCACGTAGTGGGCCATCGCCCTGA

TAGACGGTTTTTCGCCCTTTGACGTTGGAGTCCACGTTCTTTAATAGTGGACTCTTGTTC

CAAACTGGAACAACACTCAACCCTATCTCGGTCTATTCTTTTGATTTATAAGGGATTTTG

CCGATTTCGGCCTATTGGTTAAAAAATGAGCTGATTTAACAAAAATTTAACGCGAATTTT

AACAAAATCATGTGAGCAAAAGGCCAGCAAAAGGCCAGGAACCGTAAAAAGGCCGCGTTG

CTGGCGTTTTTCCATAGGCTCCGCCCCCCTGACGAGCATCACAAAAATCGACGCTCAAGT

CAGAGGTGGCGAAACCCGACAGGACTATAAAGATACCAGGCGTTTCCCCCTGGAAGCTCC

CTCGTGCGCTCTCCTGTTCCGACCCTGCCGCTTACCGGATACCTGTCCGCCTTTCTCCCT

TCGGGAAGCGTGGCGCTTTCTCATAGCTCACGCTGTAGGTATCTCAGTTCGGTGTAGGTC

GTTCGCTCCAAGCTGGGCTGTGTGCACGAACCCCCCGTTCAGCCCGACCGCTGCGCCTTA

-continued

TCCGGTAACTATCGTCTTGAGTCCAACCCGGTAAGACACGACTTATCGCCACTGGCAGCA

GCCACTGGTAACAGGATTAGCAGAGCGAGGTATGTAGGCGGTGCTACAGAGTTCTTGAAG

TGGTGGCCTAACTACGGCTACACTAGAAGAACAGTATTTGGTATCTGCGCTCTGCTGAAG

CCAGTTACCTTCGGAAAAAGAGTTGGTAGCTCTTGATCCGGCAAACAAACCACCGCTGGT

AGCGGTGGTTTTTTTGTTTGCAAGCAGCAGATTACGCGCAGAAAAAAAGGATCTCAAGAA

GATCCTTTGATCTTTTCTACGGGGTCTGACGCTCAGTGGAACGAAAACTCACGTTAAGGG

ATTTTGGTCATGAGATTATCAAAAAGGATCTTCACCTAGATCCTTTTGATCCTCCGGCGT

TCAGCCTGTGCCACAGCCGACAGGATGGTGACCACCATTTGCCCCATATCACCGTCGGTA

CTGATCCCGTCGTCAATAAACCGAACCGCTACACCCTGAGCATCAAACTCTTTTATCAGT

TGGATCATGTCGGCGGTGTCGCGGCCAAGACGGTCGAGCTTCTTCACCAGAATGACATCA

CCTTCCTCCACCTTCATCCTCAGCAAATCCAGCCCTTCCCGATCTGTTGAACTGCCGGAT

GCCTTGTCGGTAAAGATGCGGTTAGCTTTTACCCCTGCATCTTTGAGCGCTGAGGTCTGC

CTCGTGAAGAAGGTGTTGCTGACTCATACCAGGCCTGAATCGCCCCATCATCCAGCCAGA

AAGTGAGGGAGCCACGGTTGATGAGAGCTTTGTTGTAGGTGGACCAGTTGGTGATTTTGA

ACTTTTGCTTTGCCACGGAACGGTCTGCGTTGTCGGGAAGATGCGTGATCTGATCCTTCA

ACTCAGCAAAAGTTCGATTTATTCAACAAAGCCGCCGTCCCGTCAAGTCAGCGTAATGCT

CTGCCAGTGTTACAACCAATTAACCAATTCTGATTAGAAAAACTCATCGAGCATCAAATG

AAACTGCAATTTATTCATATCAGGATTATCAATACCATATTTTTGAAAAAGCCGTTTCTG

TAATGAAGGAGAAAACTCACCGAGGCAGTTCCATAGGATGGCAAGATCCTGGTATCGGTC

TGCGATTCCGACTCGTCCAACATCAATACAACCTATTAATTTCCCCTCGTCAAAAATAAG

GTTATCAAGTGAGAAATCACCATGAGTGACGACTGAATCCGGTGAGAATGGCAAAAGCTT

ATGCATTTCTTTCCAGACTTGTTCAACAGGCCAGCCATTACGCTCGTCATCAAAATCACT

CGCATCAACCAAACCGTTATTCATTCGTGATTGCGCCTGAGCGAGACGAAATACGCGATC

GCTGTTAAAAGGACAATTACAAACAGGAATCGAATGCAACCGGCGCAGGAACACTGCCAG

CGCATCAACAATATTTTCACCTGAATCAGGATATTCTTCTAATACCTGGAATGCTGTTTT

CCCGGGGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTAACATC

ATTGGCAACGCTACCTTTGCCATGTTTCAGAAACAACTCTGGCGCATCGGGCTTCCCATA

CAATCGATAGATTGTCGCACCTGATTGCCCGACATTATCGCGAGCCCATTTATACCCATA

TAAATCAGCATCCATGTTGGAATTTAATCGCGGCCTCGAGCAAGACGTTTCCCGTTGAAT

ATGGCTCATAACACCCCTTGTATTACTGTTTATGTAAGCAGACAGTTTTATTGTTCATGA

TGATATATTTTTATCTTGTGCAATGTAACATCAGAGATTTTGAGACACCATGTTCTTTCC

TGCGTTATCCCCTGATTCTGTGGATAACCGTATTACCGCCTTTGAGTGAGCTGATACCGC

TCGCCGCAGCCGAACGACCGAGCGCAGCGAGTCAGTGAGCGAGGAAGCGGAAGAGCGCCC

AATACGCAAACCGCCTCTCCCCGCGCGTTGGCCGATTCATTAATGCAGCTGGCACGACAG

GTTTCCCGACTGGAAAGCGGGCAGTGAGCGCAACGCAATTAATGTGAGTTAGCTCACTCA

TTAGGCACCCCAGGCTTTACACTTTATGCTTCCGGCTCGTATGTTGTGTGGAATTGTGAG

CGGATAACAATTTCACACAGGAAACAGCTATGACCATGATTACGCCAGATTTAATTAAGG

CCTTAATTAGG

Polynucleotide Sequences of the Invention:

1. CODON-OPTIMIZED GAMT POLYNUCLEOTIDE
(SEQ ID NO: 1)

ATGTCCGCCCCTTCAGCCACCCCCATCTTCGCCCCCGGGG

AAAACTGTAGTCCAGCATGGGGCGCCGCACCAGCCGCCTA

CGATGCCGCCGACACACACCTTAGGATTCTGGGTAAACCT

GTAATGGAACGATGGGAGACCCCCTATATGCACGCACTCG

CAGCCGCCGCCTCTTCCAAAGGAGGGCGCGTTCTTGAAGT

CGGCTTTGGAATGGCGATCGCAGCTTCAAAGGTTCAGGAG

GCCCCTATTGATGAGCATTGGATAATTGAATGTAATGATG

GTGTGTTTCAGAGATTGCGGGATTGGGCCCCAAGACAAAC

ACACAAGGTTATACCTCTTAAAGGACTGTGGGAAGACGTC

GCGCCAACTCTCCCTGATGGACACTTTGACGGCATTTTGT

ATGACACCTACCCCCTCTCCGAAGAAACATGGCACACGCA

TCAGTTCAACTTTATTAAAAATCACGCTTTTCGACTCCTC

AAACCGGGTGGAGTCCTCACATACTGCAACTTGACATCTT

GGGGTGAACTTATGAAATCTAAATATTCCGATATCACCAT

AATGTTCGAGGAGACCCAAGTGCCAGCGCTCCTTGAGGCC

GGTTTTAGACGCGAAAACATCAGAACTGAAGTCATGGCGC

TTGTGCCCCCCGCCGATTGCCGCTATTATGCCTTTCCTCA

AATGATTACCCCACTTGTGACAAAAGGTTAG.

2. CODON-OPTIMIZED SLC6A8 POLYNUCLEOTIDE
(SEQ ID NO: 2)

ATGGCAAAGAAAAGCGCTGAAAATGGTATCTACAGCGTCA

GTGGGGATGAGAAGAAAGGACCTTTGATCGCACCTGGACC

AGACGGAGCACCCGCCAAGGGAGACGGGCCTGTGGGCCTT

GGGACACCAGGGGGTCGCCTTGCGGTGCCACCTCGAGAGA

CCTGGACCCGGCAAATGGATTTCATAATGAGTTGCGTAGG

TTTTGCTGTGGGACTCGGTAACGTGTGGCGGTTCCCCTAT

CTGTGCTACAAAAACGGGGGAGGCGTTTTCCTCATACCCT

ATGTGCTGATCGCCCTCGTCGGAGGTATTCCAATTTTCTT

TCTGGAGATCTCCCTGGGCCAATTTATGAAAGCTGGAAGC

ATCAACGTGTGGAACATCTGTCCTCTGTTTAAAGGTCTGG

GTTATGCGTCAATGGTGATTGTGTTTTATTGTAACACCTA

CTATATCATGGTATTGGCGTGGGGATTTTACTATCTGGTG

AAGAGTTTCACAACAACCCTCCCCTGGGCCACATGCGGCC

ATACATGGAACACACCAGATTGTGTCGAAATCTTTCGGCA

TGAAGACTGTGCGAACGCTTCTCTGGCCAATCTGACTTGC

GACCAGTTGGCCGATAGAAGGAGTCCTGTCATCGAATTTT

GGGAAAACAAGGTGTTGCGGCTGTCTGGCGGACTGGAGGT

TCCGGGGGCACTGAACTGGGAGGTTACGTTGTGCCTGCTG

GCCTGCTGGGTCTTGGTATACTTCTGTGTGTGGAAGGGAG

-continued

TGAAATCTACCGGGAAGATTGTTTATTTTACTGCGACCTT

TCCTTACGTCGTGCTCGTGGTGCTGCTGGTTAGAGGAGTG

TTGCTCCCCGGGGCACTGGATGGCATCATCTATTATCTTA

AGCCCGATTGGAGCAAGCTCGGCTCACCTCAGGTTTGGAT

TGATGCTGGCACACAGATTTTCTTTAGTTATGCAATCGGA

TTGGGCGCATTGACCGCCCTCGGCAGTTACAACCGCTTCA

ACAACAACTGTTACAAAGATGCCATAATACTCGCTCTGAT

AAATAGTGGTACTTCCTTTTTTGCGGGTTTTGTTGTTTTT

TCAATCCTGGGGTTTATGGCAGCAGAGCAGGGTGTCCACA

TTTCCAAAGTGGCGGAGAGCGGTCCCGGACTTGCCTTTAT

CGCGTACCCAAGAGCCGTCACACTGATGCCCGTCGCCCCT

CTCTGGGCTGCCCTGTTTTTTTTTATGTTGTTGCTTCTGG

GACTCGATTCTCAGTTTGTCGGAGTGGAGGGCTTTATAAC

CGGACTCCTTGACTTGCTCCCCGCGTCTTACTACTTCAGA

TTCCAGCGCGAGATTTCTGTCGCCCTGTGCTGCGCTCTGT

GTTTTGTGATCGACCTCTCAATGGTTACCGACGGCGGGAT

GTATGTCTTTCAGCTCTTCGATTACTACTCTGCCTCAGGA

ACAACTTTGCTCTGGCAGGCTTTCTGGGAATGCGTTGTAG

TTGCTTGGGTTTATGGCGCTGATAGATTTATGGATGACAT

CGCGTGTATGATAGGCTATCGCCCCTGCCCCTGGATGAAA

TGGTGTTGGTCATTTTTCACACCCTTGGTATGTATGGGTA

TCTTCATTTTTAACGTTGTATACTACGAACCACTCGTCTA

CAATAACACCTACGTCTACCCATGGTGGGGAGAAGCGATG

GGATGGGCCTTTGCCCTGTCTTCTATGTTGTGTGTGCCAC

TCCACCTGTTGGGTTGTCTCCTTAGGGCTAAAGGAACCAT

GGCCGAGCGCTGGCAGCATCTGACTCAGCCTATATGGGGC

TTGCATCATCTGGAATATAGAGCGCAGGATGCCGACGTCC

GCGGCCTCACTACTCTCACACCTGTTTCTGAGTCCTCCAA

AGTAGTTGTGGTTGAATCAGTAATGTAA.

3. pscAAV-CMV-CBA-hcoGAMT-isoform1-CpGdel sequence
(SEQ ID NO: 10)

AAAGCTTCCCGGGGGGATCTGGGCCACTCCCTCTCTGCGC

GCTCGCTCGCTCACTGAGGCCGGGCGACCAAAGGTCGCCC

GACGCCCGGGCTTTGCCCGGGCGGCCTCAGTGAGCGAGCG

AGCGCGCAGAGAGGGAGTGGCCAACTCCATCACTAGGGGT

TCCTGGAGGGGTGGAGTCGTGAGAATTCGAGCTCGGCATT

GATTATTGACTAGTTATTAATAGTAATCAATTACGGGGTC

ATTAGTTCATAGCCCATATATGGAGTTCCGCGTTACATAA

CTTACGGTAAATGGCCCGCCTGGCTGACCGCCCAACGACC

CCCGCCCATTGACGTCAATAATGACGTATGTTCCCATAGT

AACGCCAATAGGGACTTTCCATTGACGTCAATGGGTGGAG

-continued

TATTTACGGTAAACTGCCCACTTGGCAGTACATCAAGTGT

ATCATATGCCAAGTCCGCCCCCTATTGACGTCAATGACGG

TAAATGGCCCGCCTGGCATTATGCCCAGTACATGACCTTA

CGGGACTTTCCTACTTGGCAGTACATCTACGTATTAGTCA

TCGCTATTACCATGGAGCTCTCGAGGTGAGCCCCACGTTC

TGCTTCACTCTCCCCATCTCCCCCCCCTCCCCACCCCCAA

TTTTGTATTTATTTATTTITTAATTATTTTGTGCAGCGAT

GGGGGCGGGGGGGGGGGGGGGCGCGCGCCAGGCGGGGCG

GGGGGGGCGAGGGGGGGGGGGGGCGAGGCGGAGAGGTGCG

GCGGCAGCCAATCAGAGCGGCGCGCTCCGAAAGTTTCCTT

TTATGGCGAGGCGGCGGCGGCGGCGGCCCTATAAAAAGCG

AAGCGCGCGGCGGGCGGTAAGTATCAAGGTTACAAGACAG

GTTTAAGGAGACCAATAGAAACTGGGCTTGTCGAGACAGA

GAAGACTCTTGCGTTTCTGATAGGCACCTATTGGTCTTAC

TGACATCCACTTTGCCTTTCTCTCCACAGGGATCCGCCGC

CACCATGAGTGCTCCAAGTGCCACACCCATTTTTGCACCA

GGAGAGAATTGTTCACCTGCTTGGGGAGCTGCACCTGCAG

CCTATGATGCTGCTGATACACACCTGAGAATCTTGGGCAA

GCCTGTGATGGAAAGGTGGGAAACACCCTACATGCATGCT

CTGGCTGCTGCTGCAAGCAGCAAAGGGGGCAGAGTCCTGG

AGGTGGGATTTGGCATGGCCATTGCTGCTTCAAAGGTGCA

GGAGGCACCTATTGATGAACATTGGATAATTGAGTGTAAT

GATGGAGTGTTTCAGAGGCTCAGAGACTGGGCCCCCAGAC

AGACTCATAAGGTCATCCCCCTGAAAGGTCTGTGGGAAGA

TGTGGCACCTACCCTCCCAGATGGCCATTTTGATGGGATT

CTTTATGATACATACCCTTTGTCAGAAGAAACATGGCACA

CACATCAGTTTAACTTCATCAAGAACCATGCATTTAGACT

GCTTAAACCTGGGGGGGTGCTTACTTATTGCAACCTGACA

TCTTGGGGGGAGCTGATGAAGAGCAAGTATTCAGACATTA

CCATCATGTTTGAAGAGACTCAGGTTCCTGCACTGCTGGA

AGCTGGGTTCAGAAGGGAGAACATCAGAACTGAGGTGATG

GCCCTGGTGCCCCCTGCTGACTGTAGATACTATGCCTTCC

CTCAGATGATCACCCCTCTGGTGACCAAAGGCTAAGGATC

CGAATTCTGCTTTATTTGTGAAATTTGTGATGCTATTGCT

TTATTTGTAACCATTATAAGCTGCAATAAACAAGTTAACA

ACAACAATTGCATTCATTTTATGTTTCAGGTTCAGGGGGA

GGTGTGGGAGGTTTTTTAAACTAGTCCACTCCCTCTCTGC

GCGCTCGCTCGCTCACTGAGGCCGGGCGACCAAAGGTCGC

CCGACGCCCGGGCTTTGCCCGGGCGGCCTCAGTGAGCGAG

CGAGCGCGCAGAGAGGGACAGATCCGGGCCCGCATGCGTC

GACAATTCACTGGCCGTCGTTTTACAACGTCGTGACTGGG

-continued

AAAACCCTGGCGTTACCCAACTTAATCGCCTTGCAGCACA

TCCCCCTTTCGCCAGCTGGCGTAATAGCGAAGAGGCCCGC

ACCGATCGCCCTTCCCAACAGTTGCGCAGCCTGAATGGCG

AATGGCGCCTGATGCGGTATTTTCTCCTTACGCATCTGTG

CGGTATTTCACACCGCATATGGTGCACTCTCAGTACAATC

TGCTCTGATGCCGCATAGTTAAGCCAGCCCCGACACCCGC

CAACACCCGCTGACGCGCCCTGACGGGCTTGTCTGCTCCC

GGCATCCGCTTACAGACAAGCTGTGACCGTCTCCGGGAGC

TGCATGTGTCAGAGGTTTTCACCGTCATCACCGAAACGCG

CGAGACGAAAGGGCCTCGTGATACGCCTATTTTTATAGGT

TAATGTCATGATAATAATGGTTTCTTAGACGTCAGGTGGC

ACTTTTCGGGGAAATGTGCGCGGAACCCCTATTTGTTTAT

TTTTCTAAATACATTCAAATATGTATCCGCTCATGAGACA

ATAACCCTGATAAATGCTTCAATAATATTGAAAAAGGAAG

AGTATGAGTATTCAACATTTCCGTGTCGCCCTTATTCCCT

TTTTTGCGGCATTTTGCCTTCCTGTTTTTGCTCACCCAGA

AACGCTGGTGAAAGTAAAAGATGCTGAAGATCAGTTGGGT

GCACGAGTGGGTTACATCGAACTGGATCTCAACAGCGGTA

AGATCCTTGAGAGTTTTCGCCCCGAAGAACGTTTTCCAAT

GATGAGCACTTTTAAAGTTCTGCTATGTGGCGCGGTATTA

TCCCGTATTGACGCCGGGCAAGAGCAACTCGGTCGCCGCA

TACACTATTCTCAGAATGACTTGGTTGAGTACTCACCAGT

CACAGAAAAGCATCTTACGGATGGCATGACAGTAAGAGAA

TTATGCAGTGCTGCCATAACCATGAGTGATAACACTGCGG

CCAACTTACTTCTGACAACGATCGGAGGACCGAAGGAGCT

AACCGCTTTTTTGCACAACATGGGGGATCATGTAACTCGC

CTTGATCGTTGGGAACCGGAGCTGAATGAAGCCATACCAA

ACGACGAGCGTGACACCACGATGCCTGTAGCAATGGCAAC

AACGTTGCGCAAACTATTAACTGGCGAACTACTTACTCTA

GCTTCCCGGCAACAATTAATAGACTGGATGGAGGCGGATA

AAGTTGCAGGACCACTTCTGCGCTCGGCCCTTCCGGCTGG

CTGGTTTATTGCTGATAAATCTGGAGCCGGTGAGCGTGGG

TCTCGCGGTATCATTGCAGCACTGGGGCCAGATGGTAAGC

CCTCCCGTATCGTAGTTATCTACACGACGGGGAGTCAGGC

AACTATGGATGAACGAAATAGACAGATCGCTGAGATAGGT

GCCTCACTGATTAAGCATTGGTAACTGTCAGACCAAGTTT

ACTCATATATACTTTAGATTGATTTAAAACTTCATTTTTA

ATTTAAAAGGATCTAGGTGAAGATCCTTTTTGATAATCTC

ATGACCAAAATCCCTTAACGTGAGTTTTCGTTCCACTGAG

CGTCAGACCCCGTAGAAAAGATCAAAGGATCTTCTTGAGA

-continued

TCCTTTTTTTCTGCGCGTAATCTGCTGCTTGCAAACAAAA

AAACCACCGCTACCAGCGGTGGTTTGTTTGCCGGATCAAG

AGCTACCAACTCTTTTTCCGAAGGTAACTGGCTTCAGCAG

AGCGCAGATACCAAATACTGTTCTTCTAGTGTAGCCGTAG

TTAGGCCACCACTTCAAGAACTCTGTAGCACCGCCTACAT

ACCTCGCTCTGCTAATCCTGTTACCAGTGGCTGCTGCCAG

TGGCGATAAGTCGTGTCTTACCGGGTTGGACTCAAGACGA

TAGTTACCGGATAAGGCGCAGCGGTCGGGCTGAACGGGGG

GTTCGTGCACACAGCCCAGCTTGGAGCGAACGACCTACAC

CGAACTGAGATACCTACAGCGTGAGCTATGAGAAAGCGCC

ACGCTTCCCGAAGGGAGAAAGGCGGACAGGTATCCGGTAA

GCGGCAGGGTCGGAACAGGAGAGCGCACGAGGGAGCTTCC

AGGGGGAAACGCCTGGTATCTTTATAGTCCTGTCGGGTTT

CGCCACCTCTGACTTGAGCGTCGATTTTTGTGATGCTCGT

CAGGGGGGCGGAGCCTATGGAAAAACGCCAGCAACGCGGC

CTTTTTACGGTTCCTGGCCTTTTGCTGGCCTTTTGCTCAC

ATGTTCTTTCCTGCGTTATCCCCTGATTCTGTGGATAACC

GTATTACCGCCTTTGAGTGAGCTGATACCGCTCGCCGCAG

CCGAACGACCGAGCGCAGCGAGTCAGTGAGCGAGGAAGCG

GAAGAGCGCCCAATACGCAAACCGCCTCTCCCCGCGCGTT

GGCCGATTCATTAATGCAGCTGGCACGACAGGTTTCCCGA

CTGGAAAGCGGGCAGTGAGCGCAACGCAATTAATGTGAGT

TAGCTCACTCATTAGGCACCCCAGGCTTTACACTTTATGC

TTCCGGCTCGTATGTTGTGTGGAATTGTGAGCGGATAACA

ATTTCACACAGGAAACAGCTATGACCATGATTACGCCAAG

CTCTCGAGATCTAG

4. GAMT transgene w-CpGdel sequence (SEQ ID NO: 11)

GAATTCGAGCTCGGCATTGATTATTGACTAGTTATTAATA

GTAATCAATTACGGGGTCATTAGTTCATAGCCCATATATG

GAGTTCCGCGTTACATAACTTACGGTAAATGGCCCGCCTG

GCTGACCGCCCAACGACCCCCGCCCATTGACGTCAATAAT

GACGTATGTTCCCATAGTAACGCCAATAGGGACTTTCCAT

TGACGTCAATGGGTGGAGTATTTACGGTAAACTGCCCACT

TGGCAGTACATCAAGTGTATCATATGCCAAGTCCGCCCCC

TATTGACGTCAATGACGGTAAATGGCCCGCCTGGCATTAT

GCCCAGTACATGACCTTACGGGACTTTCCTACTTGGCAGT

ACATCTACGTATTAGTCATCGCTATTACCATGGAGCTCTC

GAGGTGAGCCCCACGTTCTGCTTCACTCTCCCCATCTCCC

CCCCCTCCCCACCCCCAATTTTGTATTTATTTATTTTTTA

ATTATTTTGTGCAGCGATGGGGGCGGGGGGGGGGGGGGGG

CGCGCGCCAGGCGGGGCGGGGCGGGGCGAGGGGCGGGGCGGG

-continued

GCGAGGCGGAGAGGTGCGGCGGCAGCCAATCAGAGCGGCG

CGCTCCGAAAGTTTCCTTTTATGGCGAGGCGGCGGCGGCG

GCGGCCCTATAAAAAGCGAAGCGCGCGGCGGGCGGTAAGT

ATCAAGGTTACAAGACAGGTTTAAGGAGACCAATAGAAAC

TGGGCTTGTCGAGACAGAGAAGACTCTTGCGTTTCTGATA

GGCACCTATTGGTCTTACTGACATCCACTTTGCCTTTCTC

TCCACAGGGATCCGCCGCCACCATGAGTGCTCCAAGTGCC

ACACCCATTTTTGCACCAGGAGAGAATTGTTCACCTGCTT

GGGGAGCTGCACCTGCAGCCTATGATGCTGCTGATACACA

CCTGAGAATCTTGGGCAAGCCTGTGATGGAAAGGTGGGAA

ACACCCTACATGCATGCTCTGGCTGCTGCTGCAAGCAGCA

AAGGGGGCAGAGTCCTGGAGGTGGGATTTGGCATGGCCAT

TGCTGCTTCAAAGGTGCAGGAGGCACCTATTGATGAACAT

TGGATAATTGAGTGTAATGATGGAGTGTTTCAGAGGCTCA

GAGACTGGGCCCCCAGACAGACTCATAAGGTCATCCCCCT

GAAAGGTCTGTGGGAAGATGTGGCACCTACCCTCCCAGAT

GGCCATTTTGATGGGATTCTTTATGATACATACCCTTTGT

CAGAAGAAACATGGCACACACATCAGTTTAACTTCATCAA

GAACCATGCATTTAGACTGCTTAAACCTGGGGGGGTGCTT

ACTTATTGCAACCTGACATCTTGGGGGGAGCTGATGAAGA

GCAAGTATTCAGACATTACCATCATGTTTGAAGAGACTCA

GGTTCCTGCACTGCTGGAAGCTGGGTTCAGAAGGGAGAAC

ATCAGAACTGAGGTGATGGCCCTGGTGCCCCCTGCTGACT

GTAGATACTATGCCTTCCCTCAGATGATCACCCCTCTGGT

GACCAAAGGCTAAGGATCCGAATTC

GAMT CpGdel CodonOpt transgene

5. Liver-specific GAMT TVI Vector

Sequence: ITRs highlighted in bold (SEQ ID NO: 12)

gctgcgcgctcgctcgctcactgaggccgcccgggcaaag cccgggcgtcgggcgacctttggtcgcccggcctcagtga gcgagcgagcgcgcagagagggagtggccaactccatcac taggggttccttgtagttaatgattaacccgccatgctac ttatctaccagggtaatggggatcctctagaactatagct agaattcgcccttaagctagcaggttaatttttaaaaagc agtcaaaagtccaagtggcccttggcagcatttactctct ctgtttgctctggttaataatctcaggagcacaaacattc cagatccaggttaatttttaaaaagcagtcaaaagtccaa gtggcccttggcagcatttactctctctgtttgctctggt taataatctcaggagcacaaacattccagatccggcgcgc cagggctggaagctacctttgacatcatttcctctgcgaa tgcatgtataatttctacagaacctattagaaaggatcac -continued ccagcctctgcttttgtacaactttcccttaaaaaactgc caattccactgctgtttggcccaatagtgagaactttttc ctgctgcctcttggtgcttttgcctatggcccctattctg cctgctgaagacactcttgccagcatggacttaaacccct ccagctctgacaatcctctttctcttttgttttacatgaa gggtctggcagccaaagcaatcactcaaagttcaaacctt atcatttttgctttgttcctcttggccttggttttgtac atcagctttgaaaataccatcccagggttaatgctggggt taatttataactaagagtgctctagttttgcaatacagga catgctataaaaatggaaagatgttgctttctgagagaca gctttattgcggtagtttatcacagttaaattgctaacgc agtcagtgcttctgacacaacagtctcgaacttaagctgc agaagttggtcgtgaggcactgggcaggtaagtatcaagg ttacaagacaggtttaaggagaccaatagaaactgggctt gtcgagacagagaagactcttgcgtttctgataggcacct attggtcttactgacatccactttgcctttctctccacag gtgtccactcccagttcaattacagctcttaaggctagag tacttaatacgactcactataggctagcctcgagaattca cgcgtcatatgttaattaagccgccaccatgtccgcccct tcagccacccccatcttcgcccccggggaaaactgtagtc cagcatggggcgccgcaccagccgcctacgatgccgccga cacacaccttaggattctgggtaaacctgtaatggaacga tgggagacccccctatatgcacgcactcgcagccgccgcct cttccaaaggagggcgcgttcttgaagtcggctttggaat ggcgatcgcagcttcaaaggttcaggaggcccctattgat gagcattggataattgaatgtaatgatggtgtgtttcaga gattgcgggattgggccccaagacaaacacacaaggttat acctcttaaaggactgtgggaagacgtcgcgccaactctc cctgatggacactttgacggcattttgtatgacacctacc ccctctccgaagaaacatggcacacgcatcagttcaactt tattaaaaatcacgcttttcgactcctcaaaccgggtgga gtcctcacatactgcaacttgacatcttggggtgaactta tgaaatctaaatattccgatatcaccataatgttcgagga gacccaagtgccagcgctccttgaggccggttttagacgc gaaaacatcagaactgaagtcatggcgcttgtgcccccg ccgattgccgctattatgcctttcctcaaatgattacccc acttgtgacaaaaggttaggcggccgcggtacctctagag tcgacccgggcggcctcgaggacggggtgaactacgcctg aggatccgatctttttccctctgccaaaaattatggggac atcatgaagccccttgagcatctgacttctggctaataaa ggaaatttattttcattgcaatagtgtgttggaattttt -continued gtgtctctcactcggaagcaattcgttgatctgaatttcg accacccataatacccattaccctggtagataagtagcat ggcgggttaatcattaactacaaggaacccctagtgatgg agttggccactccctctctgcgcgctcgctcgctcactga ggccgggcgaccaaaggtcgcccgacgcccgggctttgcc cgggcggcctcagtgagcgagcgagcgcgcagccttaatt aacctaattcactggccgtcgttttacaacgtcgtgactg ggaaaaccctggcgttacccaacttaatcgccttgcagca catccccctttcgccagctggcgtaatagcgaagaggccc gcaccgatcgcccttcccaacagttgcgcagcctgaatgg cgaatgggacgcgccctgtagcggcgcattaagcgcggcg ggtgtggtggttacgcgcagcgtgaccgctacacttgcca gcgccctagcgcccgctcctttcgctttcttcccttcctt tctcgccacgttcgccggctttccccgtcaagctctaaat cgggggctccctttagggttccgatttagtgctttacggc acctcgaccccaaaaaacttgattagggtgatggttcacg tagtgggccatcgccctgatagacggtttttcgccctttg acgttggagtccacgttctttaatagtggactcttgttcc aaactggaacaacactcaaccctatctcggtctattcttt tgatttataagggattttgccgatttcggcctattggtta aaaaatgagctgatttaacaaaaatttaacgcgaatttta acaaaatattaacgcttacaatttaggtggcacttttcgg ggaaatgtgcgcggaacccctatttgtttatttttctaaa tacattcaaatatgtatccgctcatgagacaataaccctg ataaatgcttcaataatattgaaaaaggaagagtatgagt attcaacatttccgtgtcgcccttattcccttttttgcgg cattttgccttcctgtttttgctcacccagaaacgctggt gaaagtaaaagatgctgaagatcagttgggtgcacgagtg ggttacatcgaactggatctcaacagcggtaagatccttg agagttttcgccccgaagaacgttttccaatgatgagcac ttttaaagttctgctatgtggcgcggtattatcccgtatt gacgccgggcaagagcaactcggtcgccgcatacactatt ctcagaatgacttggttgagtactcaccagtcacagaaaa gcatcttacggatggcatgacagtaagagaattatgcagt gctgccataaccatgagtgataacactgcggccaacttac ttctgacaacgatcggaggaccgaaggagctaaccgcttt tttgcacaacatgggggatcatgtaactcgccttgatcgt tgggaaccggagctgaatgaagccataccaaacgacgagc gtgacaccacgatgcctgtagcaatggcaacaacgttgcg caaactattaactggcgaactacttactctagcttcccgg -continued

```
caacaattaatagactggatggaggcggataaagttgcag

gaccacttctgcgctcggcccttccggctggctggtttat

tgctgataaatctggagccggtgagcgtgggtctcgcggt

atcattgcagcactggggccagatggtaagccctcccgta

tcgtagttatctacacgacggggagtcaggcaactatgga

tgaacgaaatagacagatcgctgagataggtgcctcactg

attaagcattggtaactgtcagaccaagtttactcatata

tactttagattgatttaaaacttcatttttaatttaaaag

gatctaggtgaagatcctttttgataatctcatgaccaaa

atcccttaacgtgagttttcgttccactgagcgtcagacc

ccgtagaaaagatcaaaggatcttcttgagatcctttttt

tctgcgcgtaatctgctgcttgcaaacaaaaaaaccaccg

ctaccagcggtggtttgtttgccggatcaagagctaccaa

ctctttttccgaaggtaactggcttcagcagagcgcagat

accaaatactgttcttctagtgtagccgtagttaggccac

cacttcaagaactctgtagcaccgcctacatacctcgctc

tgctaatcctgttaccagtggctgctgccagtggcgataa

gtcgtgtcttaccgggttggactcaagacgatagttaccg

gataaggcgcagcggtcgggctgaacggggggttcgtgca

cacagcccagcttggagcgaacgacctacaccgaactgag

atacctacagcgtgagctatgagaaagcgccacgcttccc

gaagggagaaaggcggacaggtatccggtaagcggcaggg

tcggaacaggagagcgcacgagggagcttccagggggaaa

cgcctggtatctttatagtcctgtcgggtttcgccacctc

tgacttgagcgtcgatttttgtgatgctcgtcaggggggg

gagcctatggaaaaacgccagcaacgcggcctttttacgg

ttcctggccttttgctggccttttgctcacatgttctttc

ctgcgttatcccctgattctgtggataaccgtattaccgc

ctttgagtgagctgataccgctcgccgcagccgaacgacc

gagcgcagcgagtcagtgagcgaggaagcggaagagcgcc

caatacgcaaaccgcctctccccgcgcgttggccgattca

ttaatgcagctggcacgacaggtttcccgactggaaagcg

ggcagtgagcgcaacgcaattaatgtgagttagctcactc

attaggcaccccaggctttacactttatgcttccggctcg

tatgttgtgtggaattgtgagcggataacaatttcacaca

ggaaacagctatgaccatgattacgccagatttaattaag

gccttaattag
```

Figure 4:
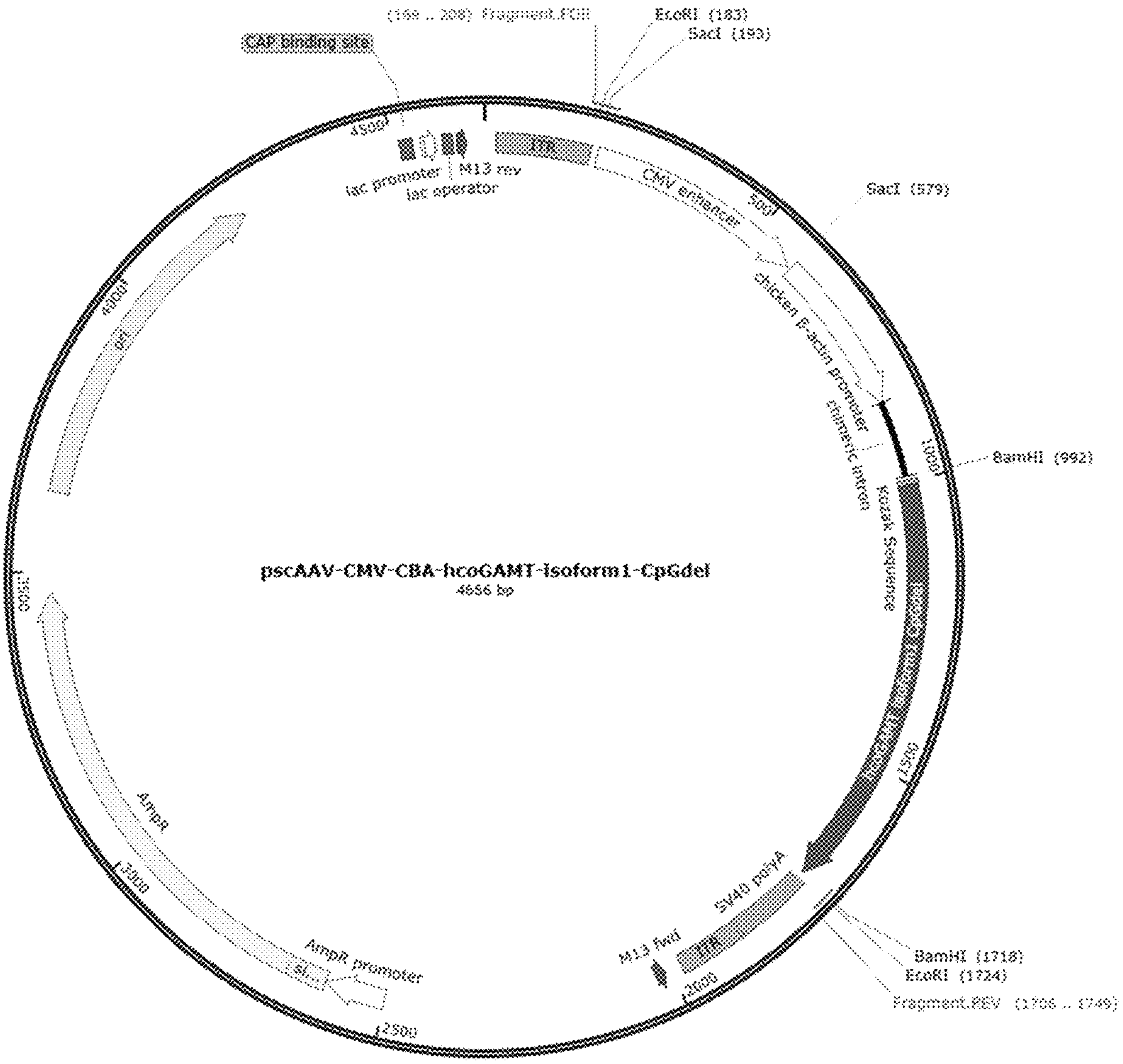
FIG. 4 provides a schematic of a map of the vector "pscAAV-CMV-CBA-hcoGAMT-isoform 1-CpGdel" including certain restriction endonuclease cleavage sites and vector elements.

FIG. 4 provides a schematic of a map of the vector "pscAAV-CMV-CBA-hcoGAMT-isoform 1-CpGdel".

REFERENCES

1. Wallimann, T, Wyss, M, Brdiczka, D, Nicolay, K, and Eppenberger, H M (1992). Intracellular compartmentation, structure and function of creatine kinase isoenzymes in tissues with high and fluctuating energy demands: the 'phosphocreatine circuit' for cellular energy homeostasis. Biochem J 281 (Pt 1): 21-40.
2. Wyss, M, and Kaddurah-Daouk, R (2000). Creatine and creatinine metabolism. Physiol Rev 80: 1107-1213.
3. Almeida, L S, Salomons, G S, Hogenboom, F, Jakobs, C, and Schoffelmeer, A N (2006). Exocytotic release of creatine in rat brain. Synapse 60: 118-123.
4. Neu, A, Neuhoff, H, Trube, G, Fehr, S, Ullrich, K, Roeper, J, Isbrandt, D. (2002). Activation of GABA(A) receptors by guanidinoacetate: a novel pathophysiological mechanism. Neurobiol Dis 11: 298-307.
5. Hanna-El-Daher, L, Beard, E, Henry, H, Tenenbaum, L, and Braissant, O (2015). Mild guanidinoacetate increase under partial guanidinoacetate methyltransferase deficiency strongly affects brain cell development. Neurobiol Dis 79: 14-27.
6. Wallimann, T, Tokarska-Schlattner, M, and Schlattner, U (2011). The creatine kinase system and pleiotropic effects of creatine. Amino Acids 40: 1271-1296.
7. Sinha, A, Ahmed, S, George, C, Tsagaris, M, Naufer, A, von Both, I, Tkachyova, I, van Eede, M, Henkelman, M, Schulze, A. (2020). Magnetic resonance imaging reveals specific anatomical changes in the brain of Agat- and Gamt-mice attributed to creatine depletion and guanidinoacetate alteration. J Inherit Metab Dis 43: 827-842.
8. Schulze, A (2003). Creatine deficiency syndromes. Mol Cell Biochem 244: 143-150.
9. Stockler, S, Marescau, B, De Deyn, PP, Trijbels, J M, and Hanefeld, F (1997). Guanidino compounds in guanidinoacetate methyltransferase deficiency, a new inborn error of creatine synthesis. Metabolism 46: 1189-1193.
10. Schulze, A, Bachert, P, Schlemmer, H, Harting, I, Polster, T, Salomons, G S, Verhoeven, N M, Jakobs, C, Fowler, B, Hoffman, G F et al. (2003). Lack of creatine in muscle and brain in an adult with GAMT deficiency. Ann Neurol 53: 248-251.
11. Arias, A, Corbella, M, Fons, C, Sempere, A, Garcia-Villoria, J, Ormazabal, A, Poo, P, Pineda, M, Vilaseca, M A, Campistol, J, et al. (2007). Creatine transporter deficiency: prevalence among patients with mental retardation and pitfalls in metabolite screening. Clin Biochem 40: 1328-1331.
12. Braissant, O, Henry, H, Beard, E, and Uldry, J (2011). Creatine deficiency syndromes and the importance of creatine synthesis in the brain. Amino Acids 40: 1315-1324.
13. Viau, K S, Ernst, S L, Pasquali, M, Botto, L D, Hedlund, G, and Longo, N (2013). Evidence-based treatment of guanidinoacetate methyltransferase (GAMT) deficiency. Mol Genet Metab 110: 255-262.
14. Mercimek-Mahmutoglu, S, Pop, A, Kanhai, W, Fernandez Ojeda, M, Holwerda, U, Smith, D, Loeber, J, Schielen, P C, Salomons (2016). A pilot study to estimate incidence of guanidinoacetate methyltransferase deficiency in newborns by direct sequencing of the GAMT gene. Gene 575: 127-131.
15. Mercimek-Mahmutoglu, S, Ndika, J, Kanhai, W, de Villemeur, T B, Cheillan, D, Christensen, E, Dorison, N, Hannig, Y, Hofstede, F C, Lion-Francois, L, et al. (2014). Thirteen new patients with guanidinoacetate methyltransferase deficiency and functional characterization of nineteen novel missense variants in the GAMT gene. Hum Mutat 35: 462-469.
16. Desroches, C L, Patel, J, Wang, P, Minassian, B, Marshall, C R, Salomons, G S, Mercimek-Mahmutoglu, S (2015). Carrier frequency of guanidinoacetate methyltransferase deficiency in the general population by functional characterization of missense variants in the GAMT gene. Mol Genet Genomics 290: 2163-2171.

17. Schulze, A, Ebinger, F, Rating, D, and Mayatepek, E (2001). Improving treatment of guanidinoacetate methyltransferase deficiency: reduction of guanidinoacetic acid in body fluids by arginine restriction and ornithine supplementation. Mol Genet Metab 74: 413-419.

18. Stockler-Ipsiroglu, S, van Karnebeek, C, Longo, N, Korenke, G C, Mercimek-Mahmutoglu, S, Marquart, I, Barshop, B, Grolik, C, Schlune, A, Angle, B et al. (2014). Guanidinoacetate methyltransferase (GAMT) deficiency: outcomes in 48 individuals and recommendations for diagnosis, treatment and monitoring. Mol Genet Metab 111: 16-25.

19. Vodopiutz, J, Item, C B, Hausler, M, Korall, H, and Bodamer, O A (2007). Severe speech delay as the presenting symptom of guanidinoacetate methyltransferase deficiency. J Child Neurol 22: 773-774.

20. Braissant, O (2012). Creatine and guanidinoacetate transport at blood-brain and blood-cerebrospinal fluid barriers. J Inherit Metab Dis 35: 655-664.

21. Battini, R, Alessandri, M G, Casalini, C, Casarano, M, Tosetti, M, and Cioni, G (2017). Fifteen-year follow-up of Italian families affected by arginine glycine amidinotransferase deficiency. Orphanet J Rare Dis 12: 21.

22. Hirayasu, Y, Morimoto, K, and Otsuki, S (1991). Increase of methylguanidine and guanidinoacetic acid in the brain of amygdala-kindled rats. Epilepsia 32: 761-766.

23. Schmidt, A, Marescau, B, Boehm, E A, Renema, W K, Peco, R, Das, A, Steinfeld, R, Chas, S, Wallis, J, Davidoff, M, et al. (2004). Severely altered guanidino compound levels, disturbed body weight homeostasis and impaired fertility in a mouse model of guanidinoacetate N-methyltransferase (GAMT) deficiency. Hum Mol Genet 13: 905-921.

24. Torremans, A, Marescau, B, Possemiers, I, Van Dam, D, D'Hooge, R, Isbrandt, D, De Deyn, P P (2005). Biochemical and behavioural phenotyping of a mouse model for GAMT deficiency. J Neurol Sci 231: 49-55.

25. Davidoff, A M, Ng, C Y, Zhou, J, Spence, Y, and Nathwani, A C (2003). Sex significantly influences transduction of murine liver by recombinant adeno-associated viral vectors through an androgen-dependent pathway. Blood 102: 480-488.

26. Kadekaro, M, Crane, A M, and Sokoloff, L (1985). Differential effects of electrical stimulation of sciatic nerve on metabolic activity in spinal cord and dorsal root ganglion in the rat. Proc Natl Acad Sci USA 82: 6010-6013.

27. Pitts, M W (2018). Barnes Maze Procedure for Spatial Learning and Memory in Mice. Bio Protoc 8.

28. Schulze, A, Tran, C, Levandovskiy, V, Patel, V, and Cortez, M A (2016). Systemic availability of guanidinoacetate affects GABAA receptor function and seizure threshold in GAMT deficient mice. Amino Acids 48: 2041-2047.

29. Schulze, A, Mayatepek, E, Bachert, P, Marescau, B, De Deyn, P P, and Rating, D (1998). Therapeutic trial of arginine restriction in creatine deficiency syndrome. Eur J Pediatr 157: 606-607.

30. Hu, C, and Lipshutz, G S (2012). AAV-based neonatal gene therapy for hemophilia A: long-term correction and avoidance of immune responses in mice. Gene Ther 19: 1166-1176.

31. Hu, C, Kasten, J, Park, H, Bhargava, R, Tai, D S, Grody, W W, Nguyen, Q G, Hauschka, S D, Cederbaum S D, Lipshutz G S (2014). Myocyte-mediated arginase expression controls hyperargininemia but not hyperammonemia in arginase-deficient mice. Mol Ther 22: 1792-1802.

32. Lee, E K, Hu, C, Bhargava, R, Ponnusamy, R, Park, H, Novicoff, S, Rozengurt, N, Marescau, B, De Deyn, P, Stout, D et al. (2013). AAV-based gene therapy prevents neuropathology and results in normal cognitive development in the hyperargininemic mouse. Gene Ther 20: 785-796.

33. Lee, E K, Hu, C, Bhargava, R, Rozengurt, N, Stout, D, Grody, W W, et al. (2012). Long-term survival of the juvenile lethal arginase-deficient mouse with AAV gene therapy. Mol Ther 20: 1844-1851.

34. Baker, S A, Gajera, C R, Wawro, A M, Corces, M R, and Montine, T J (2021). GATM and GAMT synthesize creatine locally throughout the mammalian body and within oligodendrocytes of the brain. Brain Res 1770: 147627.

35. Magami, Y, Azuma, T, Inokuchi, H, Kokuno, S, Moriyasu, F, Kawai, K, Hattori, T. (2002). Cell proliferation and renewal of normal hepatocytes and bile duct cells in adult mouse liver. Liver 22: 419-425.

36. Ishibashi, K, Onishi, A, Fujiwara, Y, Oda, K, Ishiwata, K, and Ishii, K (2018). Longitudinal effects of aging on (18)F-FDG distribution in cognitively normal elderly individuals. Sci Rep 8: 11557.

37. Seifer, F, Hajibonabi, F, Parnianfard, N, Ranjkesh, M, Valikhani, E, and Yazdchi, M (2018). Age-Related Glucose Metabolism in FDG-PET Brain Studies. Transl Neurosci Res Rev 1: 5-9.

38. Bianchi, M C, Tosetti, M, Battini, R, Leuzzi, V, Alessandri, M G, Carducci, C, Antonozzi, I, Cioni, G (2007). Treatment monitoring of brain creatine deficiency syndromes: a 1H- and 31P-MR spectroscopy study. AJNR Am J Neuroradiol 28: 548-554.

39. Depre, C, Rider, M H, and Hue, L (1998). Mechanisms of control of heart glycolysis. Eur J Biochem 258: 277-290.

40. Berg, J M, Tymoczko, J L, and Stryer, L (2002). Biochemistry, W H Freeman: New York.

41. Lock, M, Alvira, M, Vandenberghe, L H, Samanta, A, Toelen, J, Debyser, Z, Wilson, J M (2010). Rapid, simple, and versatile manufacturing of recombinant adeno-associated viral vectors at scale. Hum Gene Ther 21: 1259-1271.

42. Tran, C, Yazdanpanah, M, Kyriakopoulou, L, Levandovskiy, V, Zahid, H, Naufer, A, Isbrandt, D, Schulze, A (2014). Stable isotope dilution microquantification of creatine metabolites in plasma, whole blood and dried blood spots for pharmacological studies in mouse models of creatine deficiency. Clin Chim Acta 436: 160-168.

43. Khoja, S, Nitzahn, M, Hermann, K, Truong, B, Borzone, R, Willis, B, Rudd, M, Palmer, DJ, Ng, P, Brunetti-Pieri, N et al. (2018). Conditional disruption of hepatic carbamoyl phosphate synthetase 1 in mice results in hyperammonemia without orotic aciduria and can be corrected by liver-directed gene therapy. Mol Genet Metab 124: 243-253.

44. Ma, Y, Smith, D, Hof, P R, Foerster, B, Hamilton, S, Blackband, S J, Yu M, Benveniste, H (2008). In Vivo 3D Digital Atlas Database of the Adult C57BL/6J Mouse Brain by Magnetic Resonance Microscopy. Front Neuroanat 2: 1.

45. Patil, S S, Sunyer, B, Hoger, H, and Lubec, G (2009). Evaluation of spatial memory of C57BL/6J and CD1 mice in the Barnes maze, the Multiple T-maze and in the Morris water maze. Behav Brain Res 198: 58-68.

46. Gawel, K, Gibula, E, Marszalek-Grabska, M, Filarowska, J, and Kotlinska, J H (2019). Assessment of spatial learning and memory in the Barnes maze task in rodents-methodological consideration. Naunyn Schmiedebergs Arch Pharmacol 392: 1-18.

CONCLUSION

This concludes the description of embodiments of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

SEQUENCE LISTING

```
Sequence total quantity: 13
SEQ ID NO: 1            moltype = DNA  length = 711
FEATURE                 Location/Qualifiers
source                  1..711
                        mol_type = other DNA
                        organism = synthetic construct
SEQUENCE: 1
atgtccgccc cttcagccac ccccatcttc gcccccgggg aaaactgtag tccagcatgg  60
ggcgccgcac cagccgccta cgatgccgcc gacacacacc ttaggattct gggtaaacct  120
gtaatggaac gatgggagac cccctatatg cacgcactcg cagccgccgc ctcttccaaa  180
ggagggcgcg ttcttgaagt cggctttgga atggcgatcg cagcttcaaa ggttcaggag  240
gcccctattg atgagcattg gataattgaa tgtaatgatg gtgtgtttca gagattgcgg  300
gattgggccc caagacaaac acacaaggtt atacctctta aaggactgtg ggaagacgtc  360
gcgccaactc tccctgatgg acactttgac ggcattttgt atgacaccta ccccctctcc  420
gaagaaacat ggcacacgca tcagttcaac tttattaaaa atcacgcttt tcgactcctc  480
aaaccgggtg gagtcctcac atactgcaac ttgacatctt ggggtgaact tatgaaatct  540
aaatattccg atatcaccat aatgttcgag gagacccaag tgccagcgct ccttgaggcc  600
ggttttagac gcgaaaacat cagaactgaa gtcatggcgc ttgtgccccc cgccgattgc  660
cgctattatg cctttcctca aatgattacc ccacttgtga caaaaggtta g           711

SEQ ID NO: 2            moltype = DNA  length = 1908
FEATURE                 Location/Qualifiers
source                  1..1908
                        mol_type = other DNA
                        organism = synthetic construct
SEQUENCE: 2
atggcaaaga aaagcgctga aaatggtatc tacagcgtca gtggggatga gaagaaagga  60
cctttgatcg cacctggacc agacggagca cccgccaagg gagacgggcc tgtgggcctt  120
gggacaccag ggggtcgcct tgcggtgcca cctcgagaga cctggacccg gcaaatggat  180
ttcataatga gttgcgtagg ttttgctgtg ggactcggta acgtgtggcg gttcccctat  240
ctgtgctaca aaaacggggg aggcgttttc ctcataccct atgtgctgat cgccctcgtc  300
ggaggtattc caattttctt tctggagatc tccctgggcc aatttatgaa agctggaagc  360
atcaacgtgt ggaacatctg tcctctgttt aaaggtctgg gttatgcgtc aatggtgatt  420
gtgttttatt gtaacaccta ctatatcatg gtattggcgt ggggatttta ctatctggtg  480
aagagtttca caacaaccct cccctgggcc acatgcggcc atacatggaa cacaccagat  540
tgtgtcgaaa tctttcggca tgaagactgt gcgaacgctt ctctggccaa tctgacttgc  600
gaccagttgg ccgatagaag gagtcctgtc atcgaatttt gggaaaacaa ggtgttgcgg  660
ctgtctggcg gactggaggt tccgggggca ctgaactggg aggttacgtt gtgcctgctg  720
gcctgctggg tcttggtata cttctgtgtg tggaagggag tgaaatctac cgggaagatt  780
gtttatttta ctgcgacctt tccttacgtc gtgctcgtgg tgctgctggt tagaggagtg  840
ttgctccccg gggcactgga tggcatcatc tattatctta agcccgattg gagcaagctc  900
ggctcacctc aggtttggat tgatgctggc acacagattt tctttagtta tgcaatcgga  960
ttgggcgcat tgaccgccct cggcagttac aaccgcttca acaacaactg ttacaaagat  1020
gccataatac tcgctctgat aaatagtggt acttcctttt ttgcgggttt tgttgttttt  1080
tcaatcctgg ggtttatggc agcagagcag ggtgtccaca tttccaaagt ggcggagagc  1140
ggtcccggac ttgcctttat cgcgtaccca agagccgtca cactgatgcc cgtcgcccct  1200
ctctgggctg ccctgttttt ttttatgttg ttgcttctgg gactcgattc tcagtttgtc  1260
ggagtggagg gctttataac cggactcctt gacttgctcc ccgcgtctta ctacttcaga  1320
ttccagcgcg agatttctgt cgccctgtgc tgcgctctgt gttttgtgat cgacctctca  1380
atggttaccg acggcgggat gtatgtcttt cagctcttcg attactactc tgcctcagga  1440
acaactttgc tctggcaggc tttctgggaa tgcgttgtag ttgcttgggt ttatggcgct  1500
gatagattta tggatgacat cgcgtgtatg ataggctatc gcccctgccc ctggatgaaa  1560
tggtgttggt catttttcac accettggta tgtatgggta tcttcatttt taacgttgta  1620
tactacgaac cactcgtcta caataacacc tacgtctacc catggtgggg agaagcgatg  1680
ggatgggcct ttgccctgtc ttctatgttg tgtgtgccac tccacctgtt gggttgtctc  1740
cttagggcta aaggaaccat ggccgagcgc tggcagcatc tgactcagcc tatatggggc  1800
ttgcatcatc tggaatatag agcgcaggat gccgacgtcc gcggcctcac tactctcaca  1860
cctgtttctg agtcctccaa agtagttgtg gttgaatcag taatgtaa              1908

SEQ ID NO: 3            moltype = DNA  length = 20
FEATURE                 Location/Qualifiers
source                  1..20
                        mol_type = other DNA
                        organism = synthetic construct
SEQUENCE: 3
cacaccttag gattctgggt                                              20
```

```
SEQ ID NO: 4            moltype = DNA  length = 19
FEATURE                 Location/Qualifiers
source                  1..19
                        mol_type = other DNA
                        organism = synthetic construct
SEQUENCE: 4
cctcctgaac ctttgaagc                                              19

SEQ ID NO: 5            moltype = DNA  length = 20
FEATURE                 Location/Qualifiers
source                  1..20
                        mol_type = other DNA
                        organism = synthetic construct
SEQUENCE: 5
ctaaggccaa ccgtgaaaag                                             20

SEQ ID NO: 6            moltype = DNA  length = 20
FEATURE                 Location/Qualifiers
source                  1..20
                        mol_type = other DNA
                        organism = synthetic construct
SEQUENCE: 6
accagaggca tacagggaca                                             20

SEQ ID NO: 7            moltype = DNA  length = 4807
FEATURE                 Location/Qualifiers
source                  1..4807
                        mol_type = other DNA
                        organism = synthetic construct
SEQUENCE: 7
gctgcgcgct cgctcgctca ctgaggccgc ccgggcaaag cccgggcgtc gggcgacctt  60
tggtcgcccg gcctcagtga gcgagcgagc gcgcagagag ggagtggcca actccatcac  120
taggggttcc ttgtagttaa tgattaaccc gccatgctac ttatctacca gggtaatggg  180
gatcctctag aactatagct agaattcgcc cttaagctag caggttaatt tttaaaaagc  240
agtcaaaagt ccaagtggcc cttggcagca tttactctct ctgtttgctc tggttaataa  300
tctcaggagc acaaacattc cagatccagg ttaattttta aaaagcagtc aaaagtccaa  360
gtggcccttg gcagcattta ctctctctgt ttgctctggt taataatctc aggagcacaa  420
acattccaga tccggcgcgc cacacccaaa tatggctcgc gctctaaaaa taaccctggg  480
acacccgaga tgcctggtta taattaaccc agacatgtgg ctgccccccc caacacctgc  540
tgccgctcac aagtgttgca ttcctctctg cccgctcctt ctttggtcac agagaggaat  600
gcaacacttg tgagccagag aggaatgcaa cacttgtgag ccgctctaaa aataaccctg  660
aacacccaaa tatggctcgg gccagctgtc ccccgcatgc ggcccctccc tggggagggc  720
ccctcctggc tagtcacacc ctgtaggctc ctctatataa cccaggggca caggggctgc  780
ccccgggtca ccaccacctc cacagcacag acagacactc aggagccagc cagcacgcgt  840
catatgttaa ttaagccgcc accatgtccg ccccttcagc cacccccatc ttcgcccccg  900
gggaaaactg tagtccagca tggggcgccg caccagccgc ctacgatgcc gccgacacac  960
accttaggat tctgggtaaa cctgtaatgg aacgatggga gaccccctat atgcacgcac  1020
tcgcagccgc cgcctcttcc aaaggagggc gcgttcttga agtcggcttt ggaatggcga  1080
tcgcagcttc aaaggttcag gaggccccta ttgatgagca ttggataatt gaatgtaatg  1140
atggtgtgtt tcagagattg cgggattggg ccccaagaca aacacacaag gttatacctc  1200
ttaaaggact gtgggaagac gtcgcgccaa ctctccctga tggacacttt gacggcattt  1260
tgtatgacac ctacccccctc tccgaagaaa catggcacac gcatcagttc aactttatta  1320
aaaatcacgc ttttcgactc ctcaaaccgg gtggagtcct cacatactgc aacttgacat  1380
cttggggtga acttatgaaa tctaaatatt ccgatatcac cataatgttc gaggagaccc  1440
aagtgccagc gctccttgag gccggtttta gacgcgaaaa catcagaact gaagtcatgg  1500
cgcttgtgcc ccccgccgat tgccgctatt atgcctttcc tcaaatgatt accccacttg  1560
tgacaaaagg ttaggcggcc gcggtacctc tagagtcgac ccgggcggcc tcgaggacgg  1620
ggtgaactac gcctgaggat ccgatctttt tccctctgcc aaaaattatg gggacatcat  1680
gaagcccctt gagcatctga cttctggcta ataaaggaaa tttattttca ttgcaatagt  1740
gtgttggaat tttttgtgtc tctcactcgg aagcaattcg ttgatctgaa tttcgaccac  1800
ccataatacc cattaccctg gtagataagt agcatggcgg gttaatcatt aactacaagg  1860
aacccctagt gatggagttg gccactccct ctctgcgcgc tcgctcgctc actgaggccg  1920
ggcgaccaaa ggtcgcccga cgcccgggct ttgcccgggc ggcctcagtg agcgagcgag  1980
cgcgcagcct taattaacct aattcactgg ccgtcgtttt acaacgtcgt gactgggaaa  2040
accctggcgt tacccaactt aatcgccttg cagcacatcc ccctttcgcc agctggcgta  2100
atagcgaaga ggcccgcacc gatcgccctt cccaacagtt gcgcagcctg aatggcgaat  2160
gggacgcgcc ctgtagcggc gcattaagcg cggcgggtgt ggtggttacg cgcagcgtga  2220
ccgctacact tgccagcgcc ctagcgcccg ctcctttcgc tttcttccct tcctttctcg  2280
ccacgttcgc cggctttccc cgtcaagctc taaatcgggg gctcccttta gggttccgat  2340
ttagtgcttt acggcacctc gaccccaaaa aacttgatta gggtgatggt tcacgtagtg  2400
ggccatcgcc ctgatagacg gtttttcgcc ctttgacgtt ggagtccacg ttctttaata  2460
gtggactctt gttccaaact ggaacaacac tcaaccctat ctcggtctat tcttttgatt  2520
tataagggat tttgccgatt tcggcctatt ggttaaaaaa tgagctgatt taacaaaaat  2580
ttaacgcgaa ttttaacaaa atattaacgc ttacaattta ggtggcactt ttcggggaaa  2640
tgtgcgcgga acccctattt gtttattttt ctaaatacat tcaaatatgt atccgctcat  2700
gagacaataa ccctgataaa tgcttcaata atattgaaaa aggaagagta tgagtattca  2760
acatttccgt gtcgccctta ttcccttttt tgcggcattt tgccttcctg tttttgctca  2820
cccagaaacg ctggtgaaag taaaagatgc tgaagatcag ttgggtgcac gagtgggtta  2880
```

-continued

```
catcgaactg gatctcaaca gcggtaagat ccttgagagt tttcgccccg aagaacgttt  2940
tccaatgatg agcactttta aagttctgct atgtggcgcg gtattatccc gtattgacgc  3000
cgggcaagag caactcggtc gccgcataca ctattctcag aatgacttgg ttgagtactc  3060
accagtcaca gaaaagcatc ttacggatgg catgacagta agagaattat gcagtgctgc  3120
cataaccatg agtgataaca ctgcggccaa cttacttctg acaacgatcg gaggaccgaa  3180
ggagctaacc gcttttttgc acaacatggg ggatcatgta actcgccttg atcgttggga  3240
accggagctg aatgaagcca taccaaacga cgagcgtgac accacgatgc ctgtagcaat  3300
ggcaacaacg ttgcgcaaac tattaactgg cgaactactt actctagctt cccggcaaca  3360
attaatagac tggatggagg cggataaagt tgcaggacca cttctgcgct cggcccttcc  3420
ggctggctgg tttattgctg ataaatctgg agccggtgag cgtgggtctc gcggtatcat  3480
tgcagcactg gggccagatg gtaagccctc ccgtatcgta gttatctaca cgacggggag  3540
tcaggcaact atggatgaac gaaatagaca gatcgctgag ataggtgcct cactgattaa  3600
gcattggtaa ctgtcagacc aagtttactc atatatactt tagattgatt taaaacttca  3660
tttttaattt aaaaggatct aggtgaagat cctttttgat aatctcatga ccaaaatccc  3720
ttaacgtgag ttttcgttcc actgagcgtc agaccccgta gaaaagatca aaggatcttc  3780
ttgagatcct ttttttctgc gcgtaatctg ctgcttgcaa acaaaaaaac caccgctacc  3840
agcggtggtt tgtttgccgg atcaagagct accaactctt tttccgaagg taactggctt  3900
cagcagagcg cagataccaa atactgttct tctagtgtag ccgtagttag gccaccactt  3960
caagaactct gtagcaccgc ctacatacct cgctctgcta atcctgttac cagtggctgc  4020
tgccagtggc gataagtcgt gtcttaccgg gttggactca agacgatagt taccggataa  4080
ggcgcagcgg tcgggctgaa cggggggttc gtgcacacag cccagcttgg agcgaacgac  4140
ctacaccgaa ctgagatacc tacagcgtga gctatgagaa agcgccacgc ttcccgaagg  4200
gagaaaggcg gacaggtatc cggtaagcgg cagggtcgga acaggagagc gcacgaggga  4260
gcttccaggg ggaaacgcct ggtatcttta tagtcctgtc gggtttcgcc acctctgact  4320
tgagcgtcga tttttgtgat gctcgtcagg ggggcggagc ctatggaaaa acgccagcaa  4380
cgcggccttt ttacggttcc tggccttttg ctggcctttt gctcacatgt tctttcctgc  4440
gttatcccct gattctgtgg ataaccgtat taccgccttt gagtgagctg ataccgctcg  4500
ccgcagccga acgaccgagc gcagcgagtc agtgagcgag gaagcggaag agcgcccaat  4560
acgcaaaccg cctctccccg cgcgttggcc gattcattaa tgcagctggc acgacaggtt  4620
tcccgactgg aaagcgggca gtgagcgcaa cgcaattaat gtgagttagc tcactcatta  4680
ggcaccccag gctttacact ttatgcttcc ggctcgtatg ttgtgtggaa ttgtgagcgg  4740
ataacaattt cacacaggaa acagctatga ccatgattac gccagattta attaaggcct  4800
taattag                                                           4807

SEQ ID NO: 8             moltype = DNA  length = 7090
FEATURE                  Location/Qualifiers
source                   1..7090
                         mol_type = other DNA
                         organism = synthetic construct
SEQUENCE: 8
gctgcgcgct cgctcgctca ctgaggccgc ccgggcaaag cccgggcgtc gggcgacctt  60
tggtcgcccg gcctcagtga gcgagcgagc gcgcagagag ggagtggcca actccatcac  120
taggggttcc ttgtagttaa tgattaaccc gccatgctac ttatctacca gggtaatggg  180
gatcctctag aactatagct agtcgacatt gattattgac tagttattaa tagtaatcaa  240
ttacggggtc attagttcat agcccatata tggagttccg cgttacataa cttacggtaa  300
atggcccgcc tggctgaccg cccaacgacc cccgcccatt gacgtcaata atgacgtatg  360
ttcccatagt aacgccaata gggactttcc attgacgtca atgggtggag tatttacggt  420
aaactgccca cttggcagta catcaagtgt atcatatgcc aagtacgccc cctattgacg  480
tcaatgacgg taaatggccc gcctggcatt atgcccagta catgacctta tgggactttc  540
ctacttggca gtacatctac gtattagtca tcgctattac catggtcgag gtgagcccca  600
cgttctgctt cactctcccc atctcccccc cctccccacc cccaattttg tatttattta  660
tttttaatt attttgtgca gcgatggggg cggggggggg ggggggcgc gcgccaggcg  720
gggcggggcg gggcgagggg cggggcgggg cgaggcggag aggtgcggcg gcagccaatc  780
agagcggcgc gctccgaaag tttcctttta tggcgaggcg gcggcggcgg cggccctata  840
aaaagcgaag cgcgcggcgg gcgggagtcg ctgcgcgctg ccttcgcccc gtgccccgct  900
ccgccgccgc ctcgcgccgc ccgccccggc tctgactgac cgcgttactc ccacaggtga  960
gcgggcggga cggcccttct cctccgggct gtaattagcg cttggtttaa tgacggcttg  1020
tttcttttct gtggctgcgt gaaagccttg aggggctccg ggagggccct ttgtgcgggg  1080
ggagcggctc gggggtgcg tgcgtgtgtg tgtgcgtggg gagcgccgcg tgcggctccg  1140
cgctgcccgg cggctgtgag cgctgcgggc gcggcgcggg gctttgtgcg ctccgcagtg  1200
tgcgcgaggg gagcgcggcc gggggcggtg ccccgcggtg cggggggggc tgcgagggga  1260
acaaaggctg cgtgcggggt gtgtgcgtgg gggggtgagc agggggtgtg ggcgcgtcgg  1320
tcgggctgca acccccctg cacccccctc cccgagttgc tgagcacggc ccggcttcgg  1380
gtgcggggct ccgtacgggg cgtggcgcgg ggctcgccgt gccgggcggg gggtggcggc  1440
aggtgggggt gccgggcggg gcggggccgc ctcgggccgg ggagggctcg gggggagggc  1500
gcggcggccc ccggagcgcc ggcggctgtc gaggcgcggc gagccgcagc cattgccttt  1560
tatggtaatc gtgcgagagg gcgcagggac ttcctttgtc ccaaatctgt gcggagccga  1620
aatctgggag gcgccgccgc acccctcta gcgggcgcgg ggcgaagcgg tgcggcgccg  1680
gcaggaagga aatgggcggg gagggccttc gtgcgtcgcc gcgccgccgt ccccttctcc  1740
ctctccagcc tcggggctgt ccgcgggggg acggctgcct tcggggggga cggggcaggg  1800
cggggttcgg cttctggcgt gtgaccggcg gctctagagc ctctgctaac catgttcatg  1860
ccttcttctt tttcctacag ctcctgggca acgtgctggt tattgtgctg tctcatcatt  1920
ttggcaaaga attcttaatt aagccgccac catggcaaag aaaagcgctg aaaatggtat  1980
ctacagcgtc agtggggatg agaagaaagg acctttgatc gcacctggac cagacggagc  2040
acccgccaag ggagacgggc ctgtgggcct tgggacacca gggggtcgcc ttgcggtgcc  2100
acctcgagag acctggaccc ggcaaatgga tttcataatg agttgcgtag gttttgctgt  2160
gggactcggt aacgtgtggc ggttccccta tctgtgctac aaaaacgggg gaggcgtttt  2220
cctcataccc tatgtgctga tcgccctcgt cggaggtatt ccaattttct ttctggagat  2280
ctccctgggc caatttatga aagctggaag catcaacgtg tggaacatct gtcctctgtt  2340
```

```
taaaggtctg ggttatgcgt caatggtgat tgtgttttat tgtaacacct actatatcat  2400
ggtattggcg tggggatttt actatctggt gaagagtttc acaacaaccc tcccctgggc  2460
cacatgcggc catacatgga acacaccaga ttgtgtcgaa atctttcggc atgaagactg  2520
tgcgaacgct tctctggcca atctgacttg cgaccagttg gccgatagaa ggagtcctgt  2580
catcgaattt tgggaaaaca aggtgttgcg gctgtctggc ggactggagg ttccgggggc  2640
actgaactgg gaggttacgt tgtgcctgct ggcctgctgg gtcttggtat acttctgtgt  2700
gtggaaggga gtgaaatcta ccgggaagat tgtttatttt actgcgacct ttccttacgt  2760
cgtgctcgtg gtgctgctgg ttagaggagt gttgctcccc ggggcactgg atggcatcat  2820
ctattatctt aagcccgatt ggagcaagct cggctcacct caggtttgga ttgatgctgg  2880
cacacagatt ttctttagtt atgcaatcgg attgggcgca ttgaccgccc tcggcagtta  2940
caaccgcttc aacaacaact gttacaaaga tgccataata ctcgctctga taaatagtgg  3000
tacttccttt tttgcgggtt ttgttgtttt ttcaatcctg ggtttatgg cagcagagca  3060
gggtgtccac atttccaaag tggcggagag cggtcccgga cttgccttta tcgcgtaccc  3120
aagagccgtc acactgatgc ccgtcgcccc tctctgggct gccctgtttt tttttatgtt  3180
gttgcttctg ggactcgatt ctcagtttgt cggagtggag ggctttataa ccggactcct  3240
tgacttgctc cccgcgtctt actacttcag attccagcgc gagatttctg tcgccctgtg  3300
ctgcgctctg tgttttgtga tcgacctctc aatggttacc gacggcggga tgtatgtctt  3360
tcagctcttc gattactact ctgcctcagg aacaactttg ctctggcagg ctttctggga  3420
atgcgttgta gttgcttggg tttatggcgc tgatagattt atggatgaca tcgcgtgtat  3480
gataggctat cgcccctgcc cctggatgaa atggtgttgg tcatttttca caccccttggt  3540
atgtatgggt atcttcattt ttaacgttgt atactacgaa ccactcgtct acaataacac  3600
ctacgtctac ccatggtggg gagaagcgat gggatgggcc tttgccctgt cttctatgtt  3660
gtgtgtgcca ctccacctgt tgggttgtct ccttagggct aaaggaacca tggccgagcg  3720
ctggcagcat ctgactcagc ctatatgggg cttgcatcat ctggaatata gagcgcagga  3780
tgccgacgtc cgcggcctca ctactctcac acctgtttct gagtcctcca aagtagttgt  3840
ggttgaatca gtaatgtaaa ccggtggtac ctctagagtc gacccgggcg gcctcgagga  3900
cggggtgaac tacgcctgag gatccgatct ttttccctct gccaaaaatt atggggacat  3960
catgaagccc cttgagcatc tgacttctgg ctaataaagg aaatttattt tcattgcaat  4020
agtgtgttgg aattttttgt gtctctcact cggaagcaat tcgttgatct gaatttcgac  4080
cacccataat acccattacc ctggtagata agtagcatgg cgggttaatc attaactaca  4140
aggaacccct agtgatggag ttggccactc cctctctgcg cgctcgctcg ctcactgagg  4200
ccgggcgacc aaaggtcgcc cgacgcccgg gctttgcccg ggcggcctca gtgagcgagc  4260
gagcgcgcag ccttaattaa cctaattcac tggccgtcgt tttacaacgt cgtgactggg  4320
aaaaccctgg cgttacccaa cttaatcgcc ttgcagcaca tccccctttc gccagctggc  4380
gtaatagcga agaggcccgc accgatcgcc cttcccaaca gttgcgcagc ctgaatggcg  4440
aatgggacgc gccctgtagc ggcgcattaa gcgcggcggg tgtggtggtt acgcgcagcg  4500
tgaccgctac acttgccagc gccctagcgc ccgctccttt cgctttcttc ccttcctttc  4560
tcgccacgtt cgccggcttt ccccgtcaag ctctaaatcg ggggctccct ttagggttcc  4620
gatttagtgc tttacggcac ctcgacccca aaaaacttga ttagggtgat ggttcacgta  4680
gtgggccatc gccctgatag acggtttttc gccctttgac gttggagtcc acgttcttta  4740
atagtggact cttgttccaa actggaacaa cactcaaccc tatctcggtc tattcttttg  4800
atttataagg gattttgccg atttcggcct attggttaaa aaatgagctg atttaacaaa  4860
aatttaacgc gaattttaac aaaatattaa cgcttacaat ttaggtggca cttttcgggg  4920
aaatgtgcgc ggaaccccta tttgtttatt tttctaaata cattcaaata tgtatccgct  4980
catgagacaa taaccctgat aaatgcttca ataatattga aaaaggaaga gtatgagtat  5040
tcaacatttc cgtgtcgccc ttattccctt ttttgcggca ttttgccttc ctgtttttgc  5100
tcacccagaa acgctggtga aagtaaaaga tgctgaagat cagttgggtg cacgagtggg  5160
ttacatcgaa ctggatctca acagcggtaa gatccttgag agttttcgcc ccgaagaacg  5220
ttttccaatg atgagcactt ttaaagttct gctatgtggc gcggtattat cccgtattga  5280
cgccgggcaa gagcaactcg gtcgccgcat acactattct cagaatgact tggttgagta  5340
ctcaccagtc acagaaaagc atcttacgga tggcatgaca gtaagagaat tatgcagtgc  5400
tgccataacc atgagtgata acactgcggc caacttactt ctgacaacga tcggaggacc  5460
gaaggagcta accgcttttt tgcacaacat gggggatcat gtaactcgcc ttgatcgttg  5520
ggaaccggag ctgaatgaag ccataccaaa cgacgagcgt gacaccacga tgcctgtagc  5580
aatggcaaca acgttgcgca aactattaac tggcgaacta cttactctag cttcccggca  5640
acaattaata gactggatgg aggcggataa agttgcagga ccacttctgc gctcggccct  5700
tccggctggc tggtttattg ctgataaatc tggagccggt gagcgtgggt ctcgcggtat  5760
cattgcagca ctggggccag atggtaagcc ctcccgtatc gtagttatct acacgacggg  5820
gagtcaggca actatggatg aacgaaatag acagatcgct gagataggtg cctcactgat  5880
taagcattgg taactgtcag accaagttta ctcatatata ctttagattg atttaaaact  5940
tcatttttaa tttaaaagga tctaggtgaa gatccttttt gataatctca tgaccaaaat  6000
cccttaacgt gagttttcgt tccactgagc gtcagacccc gtagaaaaga tcaaaggatc  6060
ttcttgagat cctttttttc tgcgcgtaat ctgctgcttg caaacaaaaa aaccaccgct  6120
accagcggtg gtttgtttgc cggatcaaga gctaccaact ctttttccga aggtaactgg  6180
cttcagcaga gcgcagatac caaatactgt tcttctagtg tagccgtagt taggccacca  6240
cttcaagaac tctgtagcac cgcctacata cctcgctctg ctaatcctgt taccagtggc  6300
tgctgccagt ggcgataagt cgtgtcttac cgggttggac tcaagacgat agttaccgga  6360
taaggcgcag cggtcgggct gaacgggggg ttcgtgcaca cagcccagct tggagcgaac  6420
gacctacacc gaactgagat acctacagcg tgagctatga gaaagcgcca cgcttcccga  6480
agggagaaag gcggacaggt atccggtaag cggcagggtc ggaacaggag agcgcacgag  6540
ggagcttcca gggggaaacg cctggtatct ttatagtcct gtcgggtttc gccacctctg  6600
acttgagcgt cgatttttgt gatgctcgtc aggggggcgg agcctatgga aaaacgccag  6660
caacgcggcc tttttacggt tcctggcctt ttgctggcct tttgctcaca tgttctttcc  6720
tgcgttatcc cctgattctg tggataaccg tattaccgcc tttgagtgag ctgataccgc  6780
tcgccgcagc cgaacgaccg agcgcagcga gtcagtgagc gaggaagcgg aagagcgccc  6840
aatacgcaaa ccgcctctcc ccgcgcgttg gccgattcat taatgcagct ggcacgacag  6900
gtttcccgac tggaaagcgg gcagtgagcg caacgcaatt aatgtgagtt agctcactca  6960
ttaggcaccc caggctttac actttatgct tccggctcgt atgttgtgtg gaattgtgag  7020
cggataacaa tttcacacag gaaacagcta tgaccatgat tacgccagat ttaattaagg  7080
```

```
ccttaattag                                                          7090

SEQ ID NO: 9            moltype = DNA  length = 6371
FEATURE                 Location/Qualifiers
source                  1..6371
                        mol_type = other DNA
                        organism = synthetic construct
SEQUENCE: 9
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcc tctagaacta tagctagcat gcctgcagag ggccctgcgt atgagtgcaa  240
gtgggtttta ggaccaggat gaggcggggt gggggtgcct acctgacgac cgaccccgac  300
ccactggaca agcacccaac ccccattccc caaattgcgc atcccctatc agagaggggg  360
aggggaaaca ggatgcggcg aggcgcgtgc gcactgccag cttcagcacc gcggacagtg  420
ccttcgcccc cgcctggcgg cgcgcgccac cgccgcctca gcactgaagg cgcgctgacg  480
tcactcgccg gtcccccgca aactcccctt cccggccacc ttggtcgcgt ccgcgccgcc  540
gccggcccag ccggaccgca ccacgcgagg cgcgagatag gggggcacgg gcgcgaccat  600
ctgcgctgcg gcgccggcga ctcagcgctg cctcagtctg cggtgggcag cggaggagtc  660
gtgtcgtgcc tgagagcgca gtcgaattcg gtacccttaa gactagtgaa ttcttaatta  720
agccgccacc atggcaaaga aaagcgctga aaatggtatc tacagcgtca gtggggatga  780
gaagaaagga cctttgatcg cacctggacc agacggagca cccgccaagg gagacgggcc  840
tgtgggcctt gggacaccag ggggtcgcct tgcggtgcca cctcgagaga cctggacccg  900
gcaaatggat ttcataatga gttgcgtagg ttttgctgtg ggactcggta acgtgtggcg  960
gttcccctat ctgtgctaca aaaacggggg aggcgttttc ctcataccct atgtgctgat  1020
cgccctcgtc ggaggtattc caattttctt tctggagatc tccctgggcc aatttatgaa  1080
agctggaagc atcaacgtgt ggaacatctg tcctctgttt aaaggtctgg gttatgcgtc  1140
aatggtgatt gtgttttatt gtaacaccta ctatatcatg gtattggcgt ggggatttta  1200
ctatctggtg aagagtttca caacaaccct cccctgggcc acatgcggcc atacatggaa  1260
cacaccagat tgtgtcgaaa tctttcggca tgaagactgt gcgaacgctt ctctggccaa  1320
tctgacttgc gaccagttgg ccgatagaag gagtcctgtc atcgaatttt gggaaaacaa  1380
ggtgttgcgg ctgtctggcg gactggaggt tccgggggca ctgaactggg aggttacgtt  1440
gtgcctgctg gcctgctggg tcttggtata cttctgtgtg tggaagggag tgaaatctac  1500
cgggaagatt gtttatttta ctgcgacctt tccttacgtc gtgctcgtgg tgctgctggt  1560
tagaggagtg ttgctccccg gggcactgga tggcatcatc tattatctta agcccgattg  1620
gagcaagctc ggctcacctc aggtttggat tgatgctggc acacagattt tctttagtta  1680
tgcaatcgga ttgggcgcat tgaccgccct cggcagttac aaccgcttca acaacaactg  1740
ttacaaagat gccataatac tcgctctgat aaatagtggt acttcctttt ttgcgggttt  1800
tgttgttttt tcaatcctgg ggtttatggc agcagagcag ggtgtccaca tttccaaagt  1860
ggcggagagc ggtcccggac ttgcctttat cgcgtaccca agagccgtca cactgatgcc  1920
cgtcgcccct ctctgggctg ccctgttttt ttttatgttg ttgcttctgg gactcgattc  1980
tcagtttgtc ggagtggagg gctttataac cggactcctt gacttgctcc ccgcgtctta  2040
ctacttcaga ttccagcgcg agatttctgt cgccctgtgc tgcgctctgt gttttgtgat  2100
cgacctctca atggttaccg acggcgggat gtatgtcttt cagctcttcg attactactc  2160
tgcctcagga acaactttgc tctggcaggc tttctgggaa tgcgttgtag ttgcttgggt  2220
ttatggcgct gatagattta tggatgacat cgcgtgtatg ataggctatc gcccctgccc  2280
ctggatgaaa tggtgttggt cattttttcac accccttggta tgtatgggta tcttcatttt  2340
taacgttgta tactacgaac cactcgtcta caataacacc tacgtctacc catggtgggg  2400
agaagcgatg ggatgggcct ttgccctgtc ttctatgttg tgtgtgccac tccacctgtt  2460
gggttgtctc cttagggcta aaggaaccat ggccgagcgc tggcagcatc tgactcagcc  2520
tatatggggc ttgcatcatc tggaatatag agcgcaggat gccgacgtcc gcggcctcac  2580
tactctcaca cctgtttctg agtcctccaa agtagttgtg gttgaatcag taatgtaaac  2640
cggtggtacc acgcgtggat ccaacgcgta ggtaccggcg gccgcttcga gcagacatga  2700
taagatacat tgatgagttt ggacaaacca caactagaat gcagtgaaaa aaatgcttta  2760
tttgtgaaat ttgtgatgct attgctttat ttgtaaccat tataagctgc aataaacaag  2820
ttaacaacaa caattgcatt cattttatgt ttcaggttca gggggagatg tgggaggttt  2880
tttaaagcaa gtaaaacctc tacaaatgtg gtaaaatcga taaggatctt cctagagcat  2940
ggctacgtag ataagtagca tggcgggtta atcattaact acaaggaacc cctagtgatg  3000
gagttggcca ctccctctct gcgcgctcgc tcgctcactg aggccgggcg accaaaggtc  3060
gcccgacgcc cgggctttgc ccgggcggcc tcagtgagcg agcgagcgcg cagccttaat  3120
taacctaatt cactggccgt cgttttacaa cgtcgtgact gggaaaaccc tggcgttacc  3180
caacttaatc gccttgcagc acatccccct ttcgccagct ggcgtaatag cgaagaggcc  3240
cgcaccgatc gcccttccca acagttgcgc agcctgaatg gcgaatggga cgcgccctgt  3300
agcggcgcat taagcgcggc gggtgtggtg gttacgcgca gcgtgaccgc tacacttgcc  3360
agcgccctag cgcccgctcc tttcgctttc ttcccttcct ttctcgccac gttcgccggc  3420
tttccccgtc aagctctaaa tcgggggctc cctttagggt tccgatttag tgctttacgg  3480
cacctcgacc ccaaaaaact tgattagggt gatggttcac gtagtgggcc atcgccctga  3540
tagacggttt ttcgcccttt gacgttggag tccacgttct ttaatagtgg actcttgttc  3600
caaactggaa caacactcaa ccctatctcg gtctattctt ttgatttata agggattttg  3660
ccgatttcgg cctattggtt aaaaaatgag ctgatttaac aaaaatttaa cgcgaatttt  3720
aacaaaatca tgtgagcaaa aggccagcaa aaggccagga accgtaaaaa ggccgcgttg  3780
ctggcgtttt tccataggct ccgcccccct gacgagcatc acaaaaatcg acgctcaagt  3840
cagaggtggc gaaacccgac aggactataa agataccagg cgtttccccc tggaagctcc  3900
ctcgtgcgct ctcctgttcc gaccctgccg cttaccggat acctgtccgc ctttctccct  3960
tcgggaagcg tggcgctttc tcatagctca cgctgtaggt atctcagttc ggtgtaggtc  4020
gttcgctcca agctgggctg tgtgcacgaa ccccccgttc agcccgaccg ctgcgcctta  4080
tccggtaact atcgtcttga gtccaacccg gtaagacacg acttatcgcc actggcagca  4140
gccactggta acaggattag cagagcgagg tatgtaggcg gtgctacaga gttcttgaag  4200
tggtggccta actacggcta cactagaaga acagtatttg gtatctgcgc tctgctgaag  4260
```

```
ccagttacct tcggaaaaag agttggtagc tcttgatccg gcaaacaaac caccgctggt  4320
agcggtggtt tttttgtttg caagcagcag attacgcgca gaaaaaaagg atctcaagaa  4380
gatcctttga tcttttctac ggggtctgac gctcagtgga acgaaaactc acgttaaggg  4440
attttggtca tgagattatc aaaaaggatc ttcacctaga tccttttgat cctccggcgt  4500
tcagcctgtg ccacagccga caggatggtg accaccattt gccccatatc accgtcggta  4560
ctgatcccgt cgtcaataaa ccgaaccgct acaccctgag catcaaactc ttttatcagt  4620
tggatcatgt cggcggtgtc gcggccaaga cggtcgagct tcttcaccag aatgacatca  4680
ccttcctcca ccttcatcct cagcaaatcc agcccttccc gatctgttga actgccggat  4740
gccttgtcgg taaagatgcg gttagctttt acccctgcat ctttgagcgc tgaggtctgc  4800
ctcgtgaaga aggtgttgct gactcatacc aggcctgaat cgccccatca tccagccaga  4860
aagtgaggga gccacggttg atgagagctt tgttgtaggt ggaccagttg gtgattttga  4920
acttttgctt tgccacggaa cggtctgcgt tgtcgggaag atgcgtgatc tgatccttca  4980
actcagcaaa agttcgattt attcaacaaa gccgccgtcc cgtcaagtca gcgtaatgct  5040
ctgccagtgt tacaaccaat taaccaattc tgattagaaa aactcatcga gcatcaaatg  5100
aaactgcaat ttattcatat caggattatc aataccatat ttttgaaaaa gccgtttctg  5160
taatgaagga gaaaactcac cgaggcagtt ccataggatg gcaagatcct ggtatcggtc  5220
tgcgattccg actcgtccaa catcaataca acctattaat ttcccctcgt caaaaataag  5280
gttatcaagt gagaaatcac catgagtgac gactgaatcc ggtgagaatg gcaaaagctt  5340
atgcatttct ttccagactt gttcaacagg ccagccatta cgctcgtcat caaaatcact  5400
cgcatcaacc aaaccgttat tcattcgtga ttgcgcctga gcgagacgaa atacgcgatc  5460
gctgttaaaa ggacaattac aaacaggaat cgaatgcaac cggcgcagga acactgccag  5520
cgcatcaaca atattttcac ctgaatcagg atattcttct aatacctgga atgctgtttt  5580
cccggggatc gcagtggtga gtaaccatgc atcatcagga gtacggataa aatgcttgat  5640
ggtcggaaga ggcataaatt ccgtcagcca gtttagtctg accatctcat ctgtaacatc  5700
attggcaacg ctacctttgc catgtttcag aaacaactct ggcgcatcgg gcttcccata  5760
caatcgatag attgtcgcac ctgattgccc gacattatcg cgagcccatt tatacccata  5820
taaatcagca tccatgttgg aatttaatcg cggcctcgag caagacgttt cccgttgaat  5880
atggctcata acaccccttg tattactgtt tatgtaagca gacagtttta ttgttcatga  5940
tgatatattt ttatcttgtg caatgtaaca tcagagattt tgagacacca tgttctttcc  6000
tgcgttatcc cctgattctg tggataaccg tattaccgcc tttgagtgag ctgataccgc  6060
tcgccgcagc cgaacgaccg agcgcagcga gtcagtgagc gaggaagcgg aagagcgccc  6120
aatacgcaaa ccgcctctcc ccgcgcgttg gccgattcat taatgcagct ggcacgacag  6180
gtttcccgac tggaaagcgg gcagtgagcg caacgcaatt aatgtgagtt agctcactca  6240
ttaggcaccc caggctttac actttatgct tccggctcgt atgttgtgtg gaattgtgag  6300
cggataacaa tttcacacag gaaacagcta tgaccatgat tacgccagat ttaattaagg  6360
ccttaattag g                                                       6371

SEQ ID NO: 10          moltype = DNA  length = 4656
FEATURE                Location/Qualifiers
source                 1..4656
                       mol_type = other DNA
                       organism = synthetic construct
SEQUENCE: 10
aaagcttccc ggggggatct gggccactcc ctctctgcgc gctcgctcgc tcactgaggc  60
cgggcgacca aaggtcgccc gacgcccggg ctttgcccgg gcggcctcag tgagcgagcg  120
agcgcgcaga gagggagtgg ccaactccat cactaggggt tcctggaggg gtggagtcgt  180
gagaattcga gctcggcatt gattattgac tagttattaa tagtaatcaa ttacggggtc  240
attagttcat agcccatata tggagttccg cgttacataa cttacggtaa atggcccgcc  300
tggctgaccg cccaacgacc cccgcccatt gacgtcaata atgacgtatg ttcccatagt  360
aacgccaata gggactttcc attgacgtca atgggtggag tatttacggt aaactgccca  420
cttggcagta catcaagtgt atcatatgcc aagtccgccc cctattgacg tcaatgacgg  480
taaatggccc gcctggcatt atgcccagta catgacctta cgggactttc ctacttggca  540
gtacatctac gtattagtca tcgctattac catggagctc tcgaggtgag ccccacgttc  600
tgcttcactc tccccatctc ccccccctcc ccacccccaa ttttgtattt atttattttt  660
taattatttt gtgcagcgat gggggcgggg gggggggggg ggcgcgcgcc aggcggggcg  720
gggcggggcg aggggcgggg cggggcgagg cggagaggtg cggcggcagc caatcagagc  780
ggcgcgctcc gaaagtttcc ttttatggcg aggcggcggc ggcggcggcc ctataaaaag  840
cgaagcgcgc ggcgggcggt aagtatcaag gttacaagac aggtttaagg agaccaatag  900
aaactgggct tgtcgagaca gagaagactc ttgcgtttct gataggcacc tattggtctt  960
actgacatcc actttgcctt tctctccaca gggatccgcc gccaccatga gtgctccaag  1020
tgccacaccc atttttgcac caggagagaa ttgttcacct gcttggggag ctgcacctgc  1080
agcctatgat gctgctgata cacacctgag aatcttgggc aagcctgtga tggaaaggtg  1140
ggaaacaccc tacatgcatg ctctggctgc tgctgcaagc agcaaagggg gcagagtcct  1200
ggaggtggga tttggcatgg ccattgctgc ttcaaaggtg caggaggcac ctattgatga  1260
acattggata attgagtgta atgatggagt gtttcagagg ctcagagact gggcccccag  1320
acagactcat aaggtcatcc ccctgaaagg tctgtgggaa gatgtggcac ctaccctccc  1380
agatggccat tttgatggga ttctttatga tacataccct ttgtcagaag aaacatggca  1440
cacacatcag tttaacttca tcaagaacca tgcatttaga ctgcttaaac ctgggggggt  1500
gcttacttat tgcaacctga catcttgggg ggagctgatg aagagcaagt attcagacat  1560
taccatcatg tttgaagaga ctcaggttcc tgcactgctg gaagctgggt tcagaaggga  1620
gaacatcaga actgaggtga tggccctggt gccccctgct gactgtagat actatgcctt  1680
ccctcagatg atcacccctc tggtgaccaa aggctaagga tccgaattct gctttatttg  1740
tgaaatttgt gatgctattg ctttatttgt aaccattata agctgcaata aacaagttaa  1800
caacaacaat tgcattcatt ttatgtttca ggttcagggg gaggtgtggg aggtttttta  1860
aactagtcca ctccctctct gcgcgctcgc tcgctcactg aggccgggcg accaaaggtc  1920
gcccgacgcc cgggctttgc ccgggcggcc tcagtgagcg agcgagcgcg cagagaggga  1980
cagatccggg cccgcatgcg tcgacaattc actggccgtc gttttacaac gtcgtgactg  2040
ggaaaaccct ggcgttaccc aacttaatcg ccttgcagca catccccctt tcgccagctg  2100
gcgtaatagc gaagaggccc gcaccgatcg cccttcccaa cagttgcgca gcctgaatgg  2160
```

```
cgaatggcgc ctgatgcggt attttctcct tacgcatctg tgcggtattt cacaccgcat  2220
atggtgcact ctcagtacaa tctgctctga tgccgcatag ttaagccagc cccgacaccc  2280
gccaacaccc gctgacgcgc cctgacgggc ttgtctgctc ccggcatccg cttacagaca  2340
agctgtgacc gtctccggga gctgcatgtg tcagaggttt tcaccgtcat caccgaaacg  2400
cgcgagacga aagggcctcg tgatacgcct atttttatag gttaatgtca tgataataat  2460
ggtttcttag acgtcaggtg gcacttttcg gggaaatgtg cgcggaaccc ctatttgttt  2520
atttttctaa atacattcaa atatgtatcc gctcatgaga caataaccct gataaatgct  2580
tcaataatat tgaaaaagga agagtatgag tattcaacat ttccgtgtcg cccttattcc  2640
cttttttgcg gcattttgcc ttcctgtttt tgctcaccca gaaacgctgg tgaaagtaaa  2700
agatgctgaa gatcagttgg gtgcacgagt gggttacatc gaactggatc tcaacagcgg  2760
taagatcctt gagagttttc gccccgaaga acgttttcca atgatgagca cttttaaagt  2820
tctgctatgt ggcgcggtat tatcccgtat tgacgccggg caagagcaac tcggtcgccg  2880
catacactat tctcagaatg acttggttga gtactcacca gtcacagaaa agcatcttac  2940
ggatggcatg acagtaagag aattatgcag tgctgccata accatgagtg ataacactgc  3000
ggccaactta cttctgacaa cgatcggagg accgaaggag ctaaccgctt ttttgcacaa  3060
catgggggat catgtaactc gccttgatcg ttgggaaccg gagctgaatg aagccatacc  3120
aaacgacgag cgtgacacca cgatgcctgt agcaatggca acaacgttgc gcaaactatt  3180
aactggcgaa ctacttactc tagcttcccg gcaacaatta atagactgga tggaggcgga  3240
taaagttgca ggaccacttc tgcgctcggc ccttccggct ggctggttta ttgctgataa  3300
atctggagcc ggtgagcgtg ggtctcgcgg tatcattgca gcactggggc cagatggtaa  3360
gccctcccgt atcgtagtta tctacacgac ggggagtcag gcaactatgg atgaacgaaa  3420
tagacagatc gctgagatag gtgcctcact gattaagcat tggtaactgt cagaccaagt  3480
ttactcatat atactttaga ttgatttaaa acttcatttt taatttaaaa ggatctaggt  3540
gaagatcctt tttgataatc tcatgaccaa aatcccttaa cgtgagtttt cgttccactg  3600
agcgtcagac cccgtagaaa agatcaaagg atcttcttga gatccttttt ttctgcgcgt  3660
aatctgctgc ttgcaaacaa aaaaaccacc gctaccagcg gtggtttgtt tgccggatca  3720
agagctacca actctttttc cgaaggtaac tggcttcagc agagcgcaga taccaaatac  3780
tgttcttcta gtgtagccgt agttaggcca ccacttcaag aactctgtag caccgcctac  3840
atacctcgct ctgctaatcc tgttaccagt ggctgctgcc agtggcgata agtcgtgtct  3900
taccgggttg gactcaagac gatagttacc ggataaggcg cagcggtcgg gctgaacggg  3960
gggttcgtgc acacagccca gcttggagcg aacgacctac accgaactga gatacctaca  4020
gcgtgagcta tgagaaagcg ccacgcttcc cgaagggaga aaggcggaca ggtatccggt  4080
aagcggcagg gtcggaacag gagagcgcac gagggagctt ccagggggaa acgcctggta  4140
tctttatagt cctgtcgggt ttcgccacct ctgacttgag cgtcgatttt tgtgatgctc  4200
gtcagggggg cggagcctat ggaaaaacgc cagcaacgcg gcctttttac ggttcctggc  4260
cttttgctgg ccttttgctc acatgttctt tcctgcgtta tcccctgatt ctgtggataa  4320
ccgtattacc gcctttgagt gagctgatac cgctcgccgc agccgaacga ccgagcgcag  4380
cgagtcagtg agcgaggaag cggaagagcg cccaatacgc aaaccgcctc tccccgcgcg  4440
ttggccgatt cattaatgca gctggcacga caggtttccc gactggaaag cgggcagtga  4500
gcgcaacgca attaatgtga gttagctcac tcattaggca ccccaggctt tacactttat  4560
gcttccggct cgtatgttgt gtggaattgt gagcggataa caatttcaca caggaaacag  4620
ctatgaccat gattacgcca agctctcgag atctag                          4656

SEQ ID NO: 11          moltype = DNA  length = 1547
FEATURE                Location/Qualifiers
source                 1..1547
                       mol_type = other DNA
                       organism = synthetic construct
SEQUENCE: 11
gaattcgagc tcggcattga ttattgacta gttattaata gtaatcaatt acggggtcat  60
tagttcatag cccatatatg gagttccgcg ttacataact tacggtaaat ggcccgcctg  120
gctgaccgcc caacgacccc cgcccattga cgtcaataat gacgtatgtt cccatagtaa  180
cgccaatagg gactttccat tgacgtcaat gggtggagta tttacggtaa actgcccact  240
tggcagtaca tcaagtgtat catatgccaa gtccgccccc tattgacgtc aatgacggta  300
aatggcccgc ctggcattat gcccagtaca tgaccttacg ggactttcct acttggcagt  360
acatctacgt attagtcatc gctattacca tggagctctc gaggtgagcc ccacgttctg  420
cttcactctc cccatctccc ccccctcccc acccccaatt ttgtatttat ttatttttta  480
attattttgt gcagcgatgg gggcgggggg gggggggggg cgcgcgccag gcggggcggg  540
gcggggcgag gggcggggcg gggcgaggcg gagaggtgcg gcggcagcca atcagagcgg  600
cgcgctccga aagtttcctt ttatggcgag gcggcggcgg cggcggccct ataaaaagcg  660
aagcgcgcgg cgggcggtaa gtatcaaggt tacaagacag gtttaaggag accaatagaa  720
actgggcttg tcgagacaga gaagactctt gcgtttctga taggcaccta ttggtcttac  780
tgacatccac tttgcctttc tctccacagg gatccgccgc caccatgagt gctccaagtg  840
ccacacccat ttttgcacca ggagagaatt gttcacctgc ttggggagct gcacctgcag  900
cctatgatgc tgctgataca cacctgagaa tcttgggcaa gcctgtgatg gaaaggtggg  960
aaacacccta catgcatgct ctggctgctg ctgcaagcag caaagggggc agagtcctgg  1020
aggtgggatt tggcatggcc attgctgctt caaaggtgca ggaggcacct attgatgaac  1080
attggataat tgagtgtaat gatggagtgt ttcagaggct cagagactgg gcccccagac  1140
agactcataa ggtcatcccc ctgaaaggtc tgtgggaaga tgtggcacct accctcccag  1200
atggccattt tgatgggatt ctttatgata catacccttt gtcagaagaa acatggcaca  1260
cacatcagtt taacttcatc aagaaccatg catttagact gcttaaacct gggggggtgc  1320
ttacttattg caacctgaca tcttgggggg agctgatgaa gagcaagtat tcagacatta  1380
ccatcatgtt tgaagagact caggttcctg cactgctgga agctgggttc agaagggaga  1440
acatcagaac tgaggtgatg gccctggtgc cccctgctga ctgtagatac tatgccttcc  1500
ctcagatgat cacccctctg gtgaccaaag gctaaggatc cgaattc               1547

SEQ ID NO: 12          moltype = DNA  length = 5212
FEATURE                Location/Qualifiers
source                 1..5212
```

mol_type = other DNA
organism = synthetic construct
SEQUENCE: 12
gctgcgcgct cgctcgctca ctgaggccgc ccgggcaaag cccgggcgtc gggcgacctt 60
tggtcgcccg gcctcagtga gcgagcgagc gcgcagagag ggagtggcca actccatcac 120
taggggttcc ttgtagttaa tgattaaccc gccatgctac ttatctacca gggtaatggg 180
gatcctctag aactatagct agaattcgcc cttaagctag caggttaatt tttaaaaagc 240
agtcaaaagt ccaagtggcc cttggcagca tttactctct ctgtttgctc tggttaataa 300
tctcaggagc acaaacattc cagatccagg ttaatttta aaaagcagtc aaaagtccaa 360
gtggcccttg gcagcattta ctctctctgt ttgctctggt taataatctc aggagcacaa 420
acattccaga tccggcgcgc cagggctgga agctaccttt gacatcattt cctctgcgaa 480
tgcatgtata atttctacag aacctattag aaaggatcac ccagcctctg cttttgtaca 540
actttccctt aaaaaactgc caattccact gctgtttggc ccaatagtga gaactttttc 600
ctgctgcctc ttggtgcttt tgcctatggc ccctattctg cctgctgaag acactcttgc 660
cagcatggac ttaaacccct ccagctctga caatcctctt tctcttttgt tttacatgaa 720
gggtctggca gccaaagcaa tcactcaaag ttcaaacctt atcatttttt gctttgttcc 780
tcttggcctt ggttttgtac atcagctttg aaaataccat cccagggtta atgctggggt 840
taatttataa ctaagagtgc tctagttttg caatacagga catgctataa aaatggaaag 900
atgttgcttt ctgagagaca gctttattgc ggtagtttat cacagttaaa ttgctaacgc 960
agtcagtgct tctgacacaa cagtctcgaa cttaagctgc agaagttggt cgtgaggcac 1020
tgggcaggta agtatcaagg ttacaagaca ggtttaagga gaccaataga aactgggctt 1080
gtcgagacag agaagactct tgcgtttctg ataggcacct attggtctta ctgacatcca 1140
ctttgccttt ctctccacag gtgtccactc ccagttcaat tacagctctt aaggctagag 1200
tacttaatac gactcactat aggctagcct cgagaattca cgcgtcatat gttaattaag 1260
ccgccaccat gtccgcccct tcagccaccc ccatcttcgc cccggggaa aactgtagtc 1320
cagcatgggg cgccgcacca gccgcctacg atgccgccga cacacacctt aggattctgg 1380
gtaaacctgt aatggaacga tgggagaccc cctatatgca cgcactcgca gccgccgcct 1440
cttccaaagg agggcgcgtt cttgaagtcg gctttggaat ggcgatcgca gcttcaaagg 1500
ttcaggaggc ccctattgat gagcattgga taattgaatg taatgatggt gtgtttcaga 1560
gattgcggga ttgggcccca agacaaacac acaaggttat acctcttaaa ggactgtggg 1620
aagacgtcgc gccaactctc cctgatggac actttgacgg cattttgtat gacacctacc 1680
ccctctccga agaaacatgg cacacgcatc agttcaactt tattaaaaat cacgcttttc 1740
gactcctcaa accgggtgga gtcctcacat actgcaactt gacatcttgg ggtgaactta 1800
tgaaatctaa atattccgat atcaccataa tgttcgagga gacccaagtg ccagcgctcc 1860
ttgaggccgg ttttagacgc gaaaacatca gaactgaagt catggcgctt gtgccccccg 1920
ccgattgccg ctattatgcc tttcctcaaa tgattacccc acttgtgaca aaaggttagg 1980
cggccgcggt acctctagag tcgacccggg cggcctcgag gacggggtga actacgcctg 2040
aggatccgat ctttttccct ctgccaaaaa ttatggggac atcatgaagc cccttgagca 2100
tctgacttct ggctaataaa ggaaatttat tttcattgca atagtgtgtt ggaatttttt 2160
gtgtctctca ctcggaagca attcgttgat ctgaatttcg accacccata atacccatta 2220
ccctggtaga taagtagcat ggcgggttaa tcattaacta caaggaaccc ctagtgatgg 2280
agttggccac tccctctctg cgcgctcgct cgctcactga ggccgggcga ccaaaggtcg 2340
cccgacgccc gggctttgcc cgggcggcct cagtgagcga gcgagcgcgc agccttaatt 2400
aacctaattc actggccgtc gttttacaac gtcgtgactg ggaaaaccct ggcgttaccc 2460
aacttaatcg ccttgcagca catccccctt tcgccagctg gcgtaatagc gaagaggccc 2520
gcaccgatcg cccttcccaa cagttgcgca gcctgaatgg cgaatgggac gcgccctgta 2580
gcggcgcatt aagcgcggcg ggtgtggtgg ttacgcgcag cgtgaccgct acacttgcca 2640
gcgccctagc gcccgctcct ttcgctttct tcccttcctt tctcgccacg ttcgccggct 2700
ttccccgtca agctctaaat cgggggctcc ctttagggtt ccgatttagt gctttacggc 2760
acctcgaccc caaaaaactt gattagggtg atggttcacg tagtgggcca tcgccctgat 2820
agacggtttt tcgccctttg acgttggagt ccacgttctt taatagtgga ctcttgttcc 2880
aaactggaac aacactcaac cctatctcgg tctattcttt tgatttataa gggattttgc 2940
cgatttcggc ctattggtta aaaaatgagc tgatttaaca aaaatttaac gcgaatttta 3000
acaaaatatt aacgcttaca atttaggtgg cacttttcgg ggaaatgtgc gcggaacccc 3060
tatttgttta tttttctaaa tacattcaaa tatgtatccg ctcatgagac aataaccctg 3120
ataaatgctt caataatatt gaaaaaggaa gagtatgagt attcaacatt tccgtgtcgc 3180
ccttattccc ttttttgcgg cattttgcct tcctgttttt gctcacccag aaacgctggt 3240
gaaagtaaaa gatgctgaag atcagttggg tgcacgagtg ggttacatcg aactggatct 3300
caacagcggt aagatccttg agagttttcg ccccgaagaa cgttttccaa tgatgagcac 3360
ttttaaagtt ctgctatgtg gcgcggtatt atcccgtatt gacgccgggc aagagcaact 3420
cggtcgccgc atacactatt ctcagaatga cttggttgag tactcaccag tcacagaaaa 3480
gcatcttacg gatggcatga cagtaagaga attatgcagt gctgccataa ccatgagtga 3540
taacactgcg gccaacttac ttctgacaac gatcggagga ccgaaggagc taaccgcttt 3600
tttgcacaac atgggggatc atgtaactcg ccttgatcgt tgggaaccgg agctgaatga 3660
agccatacca aacgacgagc gtgacaccac gatgcctgta gcaatggcaa caacgttgcg 3720
caaactatta actggcgaac tacttactct agcttcccgg caacaattaa tagactggat 3780
ggaggcggat aaagttgcag gaccacttct gcgctcggcc cttccggctg gctggtttat 3840
tgctgataaa tctggagccg gtgagcgtgg gtctcgcggt atcattgcag cactggggcc 3900
agatggtaag ccctcccgta tcgtagttat ctacacgacg gggagtcagg caactatgga 3960
tgaacgaaat agacagatcg ctgagatagg tgcctcactg attaagcatt ggtaactgtc 4020
agaccaagtt tactcatata tactttagat tgatttaaaa cttcattttt aatttaaaag 4080
gatctaggtg aagatccttt ttgataatct catgaccaaa atcccttaac gtgagttttc 4140
gttccactga gcgtcagacc ccgtagaaaa gatcaaagga tcttcttgag atcctttttt 4200
tctgcgcgta atctgctgct tgcaaacaaa aaaaccaccg ctaccagcgg tggtttgttt 4260
gccggatcaa gagctaccaa ctctttttcc gaaggtaact ggcttcagca gagcgcagat 4320
accaaatact gttcttctag tgtagccgta gttaggccac cacttcaaga actctgtagc 4380
accgcctaca tacctcgctc tgctaatcct gttaccagtg gctgctgcca gtggcgataa 4440
gtcgtgtctt accgggttgg actcaagacg atagttaccg gataaggcgc agcggtcggg 4500
ctgaacgggg ggttcgtgca cacagcccag cttggagcga acgacctaca ccgaactgag 4560

-continued

```
atacctacag cgtgagctat gagaaagcgc cacgcttccc gaagggagaa aggcggacag  4620
gtatccggta agcggcaggg tcggaacagg agagcgcacg agggagcttc caggggggaaa  4680
cgcctggtat ctttatagtc ctgtcgggtt tcgccacctc tgacttgagc gtcgattttt  4740
gtgatgctcg tcaggggggc ggagcctatg gaaaaacgcc agcaacgcgg cctttttacg  4800
gttcctggcc ttttgctggc cttttgctca catgttcttt cctgcgttat cccctgattc  4860
tgtggataac cgtattaccg cctttgagtg agctgatacc gctcgccgca gccgaacgac  4920
cgagcgcagc gagtcagtga gcgaggaagc ggaagagcgc ccaatacgca aaccgcctct  4980
ccccgcgcgt tggccgattc attaatgcag ctggcacgac aggtttcccg actggaaagc  5040
gggcagtgag cgcaacgcaa ttaatgtgag ttagctcact cattaggcac cccaggcttt  5100
acactttatg cttccggctc gtatgttgtg tggaattgtg agcggataac aatttcacac  5160
aggaaacagc tatgaccatg attacgccag atttaattaa ggccttaatt ag          5212

SEQ ID NO: 13          moltype = AA  length = 303
FEATURE                Location/Qualifiers
source                 1..303
                       mol_type = protein
                       organism = synthetic construct
SEQUENCE: 13
MSAPSATPIF APGENCSPAW GAAPAAYDAA DTHLRILGKP VMERWETPYM HALAAAASSK  60
GGRVLEVGFG MAIAASKVQE APIDEHWIIE CNDGVFQRLR DWAPRQTHKV IPLKGLWEDV  120
APTLPDGHFD GILYDTNIRT EVMALVPPAD CRYYAFPQMI TPLVTKGMSA PSATPIFAPG  180
ENCSPAWGAA PAAYDAADTH LRILGKPVME RWETPYMHAL AAAASSKGGR VLEVYPLSEE  240
TWHTHQFNFI KNHAFRLLKP GGVLTYCNLT SWGELMKSKY SDITIMFEET QVPALLEAGF  300
RRE                                                                303
```

The invention claimed is:

1. A method of making a pharmaceutical composition comprising combining together in an aqueous formulation:

a polynucleotide comprising the nucleotide sequence of SEQ ID NO: 1 or a polynucleotide comprising the nucleotide sequence of SEQ ID NO: 2; and a pharmaceutical excipient selected from the group consisting of:

a preservative, a tonicity adjusting agent, a detergent, a viscosity adjusting agent, a sugar and a pH adjusting agent.

2. The method of claim 1, wherein: the polynucleotide comprising the nucleotide sequence of SEQ ID NO: 1 or the polynucleotide comprising the nucleotide sequence of SEQ ID NO: 2 is in an adeno-associated viral vector.

3. The method of claim 2, wherein the adeno-associated viral vector comprises:

a polynucleotide comprising a terminal repeat sequence;

a polynucleotide comprising a promoter sequence; and a polynucleotide comprising a polyA tail sequence.

4. The method of claim 3, wherein the adeno-associated viral vector comprises a polynucleotide comprising the nucleotide sequence of SEQ ID NO: 1.

5. A composition of matter comprising:

a polynucleotide comprising the nucleotide sequence of SEQ ID NO: 1; or a polynucleotide comprising the nucleotide sequence of SEQ ID NO: 2.

6. The composition of claim 5, wherein the composition comprises:

an adeno-associated viral vector comprising:

a polynucleotide sequence comprising a terminal repeat sequence;

a polynucleotide sequence comprising a liver specific promoter;

the polynucleotide comprising the nucleotide sequence of SEQ ID NO: 1 or the polynucleotide comprising the nucleotide sequence of SEQ ID NO: 2; and a polynucleotide sequence comprising a polyA tail signal; and a pharmaceutical excipient selected from the group consisting of:

a preservative, a tonicity adjusting agent, a detergent, a viscosity adjusting agent, a sugar and a pH adjusting agent.

7. The composition of claim 6, wherein the composition comprises an adeno-associated viral vector encoding the polynucleotide comprising the nucleotide sequence of SEQ ID NO: 1 which, when transduced into a human liver cell expresses a GAMT protein.

8. The composition of claim 6, wherein the composition comprises an adeno-associated viral vector encoding the polynucleotide comprising the nucleotide sequence of SEQ ID NO: 2 which, when transduced into a human cell expresses a SLC6A8 protein.

9. A method of delivering a polynucleotide encoding a GAMT protein polypeptide or a polynucleotide encoding a SLC6A8 protein polypeptide into human cells, the method comprising:

contacting a plurality of the adeno-associated viral vector of the composition of claim 6 with the human cells so that the adeno-associated viral vectors infect the human cells, thereby delivering the polynucleotides into the human cells.

10. The method of claim 9, wherein the human cells are in vivo liver cells.

11. The method of claim 10, wherein the in vivo cells are present in an individual diagnosed with a creatine deficiency.

12. The method of claim 11, wherein the composition comprises an adeno-associated viral vector encoding the polynucleotide comprising the nucleotide sequence of SEQ ID NO: 1 which, when transduced into a human liver cell expresses a GAMT protein.

13. The method of claim 11, wherein the composition comprises an adeno-associated viral vector encoding the polynucleotide comprising the nucleotide sequence of SEQ ID NO: 2 which, when transduced into a human cell expresses a SLC6A8protein.

14. The method of claim 11, wherein the adeno-associated viral vectors are delivered intravenously to a human.

* * * * *